US007282564B2

(12) United States Patent
Mello et al.

(10) Patent No.: US 7,282,564 B2
(45) Date of Patent: Oct. 16, 2007

(54) RNA INTERFERENCE PATHWAY GENES AS TOOLS FOR TARGETED GENETIC INTERFERENCE

(75) Inventors: Craig C. Mello, Shrewsbury, MA (US); Andrew Fire, Baltimore, MD (US); Hiroaki Tabara, Worcester, MA (US); Alla Grishok, Shrewsbury, MA (US)

(73) Assignees: University of Massachusetts, Boston, MA (US); Carnegie Institute of Washington, Washington, DC (US)

( * ) Notice: Subject to any disclaimer, the term of this patent is extended or adjusted under 35 U.S.C. 154(b) by 446 days.

(21) Appl. No.: 10/645,746

(22) Filed: Aug. 20, 2003

(65) Prior Publication Data

US 2004/0265839 A1 Dec. 30, 2004

Related U.S. Application Data

(62) Division of application No. 09/689,992, filed on Oct. 13, 2000, now abandoned.

(60) Provisional application No. 60/159,776, filed on Oct. 15, 1999, provisional application No. 60/193,218, filed on Mar. 30, 2000.

(51) Int. Cl.
*C12P 21/06* (2006.01)
*C12N 15/00* (2006.01)
*C12N 1/20* (2006.01)
*C07K 1/00* (2006.01)

(52) U.S. Cl. .................. 530/350; 435/69.1; 435/252.3; 435/320.1

(58) Field of Classification Search ................. 530/350; 435/69.1, 252.3, 320.1
See application file for complete search history.

(56) References Cited

U.S. PATENT DOCUMENTS

| | | | |
|---|---|---|---|
| 4,469,863 A | 9/1984 | Ts'o et al. |
| 4,511,713 A | 4/1985 | Miller et al. |
| 5,034,323 A | 7/1991 | Jorgensen et al. |
| 5,107,065 A | 4/1992 | Shewmaker |
| 5,190,931 A | 3/1993 | Inouye |
| 5,208,149 A | 5/1993 | Inouye |
| 5,258,369 A | 11/1993 | Carter |
| 5,272,065 A | 12/1993 | Inouye |
| 5,365,015 A | 11/1994 | Grierson et al. |
| 5,453,566 A | 9/1995 | Shewmaker |
| 5,738,985 A | 4/1998 | Miles |
| 5,795,715 A | 8/1998 | Livache |
| 5,874,555 A | 2/1999 | Dervan |
| 5,976,567 A | 11/1999 | Wheeler et al. |
| 6,010,908 A | 1/2000 | Gruenert et al. |
| 6,136,601 A | 10/2000 | Meyer, Jr. et al. |

FOREIGN PATENT DOCUMENTS

| WO | WO 98/04717 | 2/1998 |
|---|---|---|
| WO | WO 98/54315 | 12/1998 |
| WO | WO 99/32619 | 7/1999 |
| WO | WO 99/53050 | 10/1999 |
| WO | WO 99/61631 | 12/1999 |
| WO | WO 00/01846 | 1/2000 |
| WO | WO 00/63364 | 10/2000 |

OTHER PUBLICATIONS

Baker et al. RNAi of the receptor tyrosine phosphatase HmLAR2 in a single cell of an intact leech embryo leads to growth-cone collapse. Curr Biol. Sep. 7, 2000;10(17):1071-4.
Bass. Double-stranded RNA as a template for gene silencing, Cell. Apr. 28, 2000;101(3):235-8.
Bastin et al. Flagellum ontogeny in trypanosomes studied via an inherited and regulated RNA interference system. J Cell Sci. Sep. 2000;113 ( Pt 18):3321-8.
Baulcombe et al. Molecular biology. Unwinding RNA silencing. Science. Nov. 10, 2000;290(5494):1108-9.
Baulcombe. Gene silencing: RNA makes RNA makes no protein. Curr Biol. Aug. 26, 1999;9(16):R599-601.
Baum et al. Inhibition of protein synthesis in reticulocyte lysates by a double-stranded RNA component in HeLa mRNA. Biochem Biophys Res Commun. Jul. 18, 1983;114(1):41-9.
Bhat et al. Discs Lost, a novel multi-PDZ domain protein, establishes and maintains epithelial polarity. Cell. Mar. 19, 1999;96(6):833-45.
Billy et al. Specific interference with a gene expression induced by long, double-stranded RNA in mouse embryonal teratocarcinoma cell lines. Proc Natl Acad Sci U S A Dec. 4, 2001;98(25):14428-33.
*C. elegans* Sequencing Consortium, The. Genome Sequence of the Nematode *C. elegans*: A Platform for Investing Biology Science. Dec. 11, 1998 282:2012-2018.
Caplen et al. dsRNA-mediated gene silencing in cultured in cultured Drosophila cells: a tissue culture model for the analysis of RNA interference. Gene. Jul. 11, 2000;252(1-2):95-105.
Caplen. A new approach to the inhibition of gene expression. Trends Biotechnol. Feb. 2002;20(2):49-51.
Catalanotto et al. Gene silencing in worms and fungi. Nature Mar. 16, 2000;404(6775):245.
Chuang et al. Specific and heritable genetic interference by double-stranded RNA in *Arabidopsis thaliana*. Proc Natl Acad Sci U S A. Apr. 25, 2000;97(9):4985-90.
Colussi et al. Debci, a proapoptotic Bcl-2 homologue, is a component of the *Drosophila melanogaster* cell death machinery. J Cell Biol. Feb. 21, 2000;148(4):703-14.
Denef et al. Hedgehog induces opposite changes in turnover and subcellular localization of patched and smoothened. Cell. Aug. 18, 2000;102(4):521-31.
Doi et al. Short-Interfering-RNA-Mediated Gene Silencing in Mammalian Cells Requires Dicer and elF2C Translation Initiation Factors. Current Biology Jan. 8, 2003 13:41-46.

(Continued)

*Primary Examiner*—Maryam Monshipouri
(74) *Attorney, Agent, or Firm*—Lahive & Cockfield, LLP; Debra J. Milasincic, Esq.

(57) ABSTRACT

Genes involved in double-stranded RNA interference (RNAi pathway genes) are identified and used to investigate the RNAi pathway. The genes and their products are also useful for modulating RNAi pathway activity.

7 Claims, 21 Drawing Sheets

OTHER PUBLICATIONS

Dolnick. Naturally occurring antisense RNA. Pharmacol Ther. Sep. 1997;75(3):179-84.

Domeier et al. A link between RNA interference and nonsense-mediated decay in *Caenorhabditis elegans*. Science. Sep. 15, 2000;289(5486):1928-31.

Driver et al. Oligonucleotide-based inhibition of embryonic gene expression. Nat Biotechnol. Dec. 1999;17(12):1184-7.

Fagard et al. AGO1, QDE-2, and RDE-1 are related proteins required for post-transcriptional gene silencing in plants, quelling in fungi, and RNA interference in animals. Proc Natl Acad Sci U S A Oct. 10, 2000;97(21):11650-4.

Fraser et al. Functional genomic analysis of *C. elegans* chromosome I by systematic RNA interference. Nature. Nov. 16, 2000;408(6810):325-30.

Fire et al. RNA-triggered gene silencing. Trends Genet. Sep. 1999;15(9):358-63.

Fire et al. Production of antisense RNA leads to effective and specific inhibition of gene expression in *C. elegans* muscle. Development. Oct. 1991;113(2):503-14.

Fire et al. Potent and specific genetic interference by double-stranded RNA in *Caenorhabditis elegans*. Nature. Feb. 19, 1998;391(6669):806-11.

Fire et al. On the Generality of RNA-Mediated Interference. Worm Breeder's Gazette. 1998;15(3):8.

Fortier et al. Temperature-dependent gene silencing by an expressed inverted repeat in Drosophila. Genesis. Apr. 2000;26(4):240-4.

Grieson et al. Trends in Biotechnology 1991;9: 122-3.

Grishok et al. Genetic requirements for inheritance of RNAi in *C. elegans*. Science. Mar. 31, 2000;287(5462):2494-7.

Guo et al. par-1, a gene required for establishing polarity in *C. elegans* embryos, encodes a putative Ser/Thr kinase that is asymmetrically distributed. Cell. May 19, 1995;81(4):611-20.

Hammond et al. An RNA-directed nuclease mediates post-transcriptional gene silencing in Drosophila cells. Nature. Mar. 16, 2000;404(6775):293-6.

Harbinder et al. Genetically targeted cell disruption in *Caenorhabditis elegans*. Proc Natl Acad Sci U S A. Nov. 25, 1997;94(24):13128-33.

Harcourt et al. Ebola virus inhibits induction of genes by double-stranded RNA in endothelial cells. Virology. Dec. 5, 1998;252(1):179-88.

Harfe et al. Analysis of a *Caenorhabditis elegans* Twist homolog identifies conserved and divergent aspects of mesodermal patterning. Genes Dev. Aug. 15, 1998;12(16):2623-35.

Heaphy, S. et al. Viruses, double stranded RNA and RNA interference. Recent Res. Devel. Virol. 2001;3:91-104.

Hill et al. dpy-18 encodes an alpha-subunit of prolyl-4 hydroxylase in *Caenorhabditis elegans*. Genetics. Jul. 2000;155(3):1139-48.

Hsieh et al. The RING finger/B-box factor TAM-1 and a retinoblastoma-like protein LIN-35 modulate context-dependent gene silencing in *Caenorhabditis elegans*. Genes Dev. Nov. 15, 1999;13(22):2958-70.

Huang et al. The proneural gene amos promotes multiple dendritic neuron formation in the Drosophila peripheral nervous system. Neuron. Jan. 2000;25(1):57-67.

Hughes et al. RNAi analysis of Deformed, proboscipedia and Sex combs reduced in the milkweed bug *Oncopeltus fasciatus*: novel roles for Hox genes in the hemipteran head. Development. Sep. 2000;127(17):3683-94.

Hunter. Genetics: a touch of elegance with RNAi. Curr Biol. Jun. 17, 1999;9(12):R440-2.

Hunter. Gene Silencing: Shrinking the Black Box of RNAi. Current Biology, 2000, 10:R137-R140.

Izant. Inhibition of Thymidine Kinase Gene Expression by Anti-Sense RNA: A Molecular Approach to Genetic Analysis. Cell. Apr. 1984, 36:1007-1015.

Jacobs et al. When two strands are better than one: the mediators and modulators of the cellular responses to double-stranded RNA. Virology. May 15, 1996;219(2):339-49.

Jorgensen et al. An RNA-based information superhighway in plants. Science. Mar. 6, 1998;279(5356):1486-7.

Jorgensen et al. Do unintended antisense transcripts contribute to sense cosuppression in plants? Trends Genet. Jan. 1999;15(1):11-2.

Judware et al. Inhibition of the dsRNA-Dependent Protein Kinase by a Peptide Derived from the Human Immunodeficiency Virus Type 1 Tat Protein. Journal of Interferon Research 1993 13:153-160.

Kelly et al. Chromatin silencing and the maintenance of a functional germine in *Caenorhabditis elegans*. Development. Jul. 1998;125(13):2451-6.

Kennerdell et al. Heritable gene silencing in Drosophila using double-stranded RNA. Nat Biotechnol. Aug. 2000;18(8):896-8.

Kennerdell et al. Use of dsRNA-mediated genetic interference to demonstrate that frizzled and frizzled 2 act in the wingless pathway. Cell. Dec. 23, 1998;95(7):1017-26.

Ketting et al. Mut-7 of *C. elegans*, required for transposon silencing and RNA interference, is a homolog of Werner syndrome helicase and RNaseD. Cell. Oct. 15, 1999;99(2):133-41.

Ketting et al. A genetic link between co-suppression and RNA interference in *C. elegans*. Nature. Mar. 16, 2000;404(6775):296-8.

Kim et al. Positioning of longitudinal nerves in *C. elegans* by nidogen. Science. Apr. 7, 2000;288(5463):150-4.

Klaff et al. RNA structure and the regulation of gene expression. Plant Mol Biol. Oct. 1996;32(1-2):89-106.

Kostich et al. Identification and molecular-genetic characterization of a LAMP/CD68-like protein from *Caenorhabditis elegans*. J Cell Sci. Jul. 2000;113 ( Pt 14):2595-606.

Kumar et al. Antisense RNA: function and fate of duplex RNA in cells of higher eukaryotes. Microbiol Mol Biol Rev. Dec. 1998;62(4):1415-34.

Lam et al. Inducible expression of double-stranded RNA directs specific genetic interference in Drosophila. Curr Biol. Aug. 24, 2000;10(16):957-63.

Lewis et al. Distinct roles of the homeotic genes Ubx and abd-A in beetle embryonic abdominal appendage development. Proc Natl Acad Sci U S A. Apr. 25, 2000;97(9):4504-9.

Li et al. Double-stranded RNA injection produces null phenotypes in zebrafish. Dev Biol. Jan. 15, 2000;217(2):394-405.

Liu et al. Overlapping roles of two Hox genes and the exd ortholog ceh-20 in diversification of the *C. elegans* postembryonic mesoderm. Development. Dec. 2000;127(23):5179-90.

Liu et al. Essential roles for *Caenorhabditis elegans* lamin gene in nuclear organization, cell cycle progression, and spatial organization of nuclear pore complexes. Mol Biol Cell. Nov. 2000;11(11):3937-47.

Lohmann et al. Silencing of developmental genes in Hydra. Dev Biol. Oct. 1, 1999;214(1):211-4.

Maine. A conserved mechanism for post-trascriptional gene siliencing? Genome Biol. 2000;1(3):REVIEWS1018.

Maitra. Catalytic cleavage of an RNA target by 2-5A antisense and RNase L. J Biol Chem Jun. 23, 1995;270(25):15071-5.

Marx. Interfering with gene expression. Science. May 26, 2000;288(5470):1370-2.

Matzke et al. How and Why Do Plants Inactivate Homologous (Trans)genes? Plant Physiol. Mar. 1995;107(3):679-685.

Mello et al. Efficient gene transfer in *C. elegans*: extrachromosomal maintenance and integration of transforming sequences. EMBO J. Dec. 1991;10(12):3959-70.

Mello et al. DNA transformation. Methods Cell Biol. 1995;48:451-82.

Metzlaff et al. RNA-mediated RNA degradation and chalcone synthase A silencing in petunia. Cell. Mar. 21, 1997;88(6):845-54.

Mette et al. Transcriptional silencing and promoter methylation triggered by double-stranded RNA. EMBO J. Oct. 2, 2000;19(19):5194-201.

Melendez et al. *Caenorhabditis elegans* lin-13, a member of the LIN-35 Rb class of genes involved in vulval development, encodes a protein with zinc fingers and an LXCXE motif. Genetics. Jul. 2000;155(3):1127-37.

Misquitta et al. Targeted disruption of gene function in Drosophila by RNA interference (RNA-i): a role for nautilus in embryonic somatic muscle information. Proc Natl Acad Sci U S A. Feb. 16, 1999;96(4):1451-6.

Montgomery et al. Double-stranded RNA as a mediator in sequence-specific genetic silencing and co-suppression. Trends Genet. Jul. 1998;14(7):255-8.

Montgomery et al. RNA as target of double-stranded RNA-mediated genetic interference in *Caenorhabditis elegans*. Proc Natl Acad Sci U S A. Dec. 22, 1998;95(26):15502-7.

Nakano et al. RNA interference for the organizer-specific gene Xlim-1 in Xenopus embryos, Biochem Biophys Res Commun. Aug. 2, 2000;274(2):434-9.

Nekhai. et al. Peptides Derived from the Interferon-Induced PKR Prevent Activation by HIV-1 TAR RNA. Virology 1996 222:193-200.

Nellen et al. What makes an mRNA anti-sense-itive? Trends Biochem Sci. Nov. 1993;18(11):419-23.

Ngo et al. Double-stranded RNA induced mRNA degradation in *Trypanosoma brucei*. Proc Natl Acad Sci U S A. Dec. 8, 1998;95(25):14687-92.

Oates et al. Too much interference: injection of double-stranded RNA has nonspecific effects in the zebrafish embryo. Dev Biol. Aug. 1, 2000;224(1):20-8.

Oelgeschlager et al. The evolutionarily conserved BMP-binding protein Twisted gastrulation promoted BMP signalling. Nature. Jun. 15, 2000;405(6788):757-63.

Paddison, P.J. et al. RNA interference: the new somatic cell genetics? Cancer Cell. Jul. 2002;2(1):17-23.

Pal-Bhadra et al. RNAi related mechanisms affect both transcriptional and posttranscriptional transgene silencing in Drosophila. Mol Cell Feb. 2002;9(2):315-27.

Parrish et al. Functional anatomy of a dsRNA trigger: differential requirement for the two trigger strands in RNA interference. Mol Cell. Nov. 2000;6(5):1077-87.

Pichler et al. OOC-3, a novel putative transmembrane protein required for establishment of cortical domains and spindle orientation in the P(1) blastomere of *C. elegans* embryos. Development. May 2000;127(10):2063-73.

Pineda et al. Searching for the prototypic eye genetic network: Sine oculis is essential for eye regeneration in planarians. Proc Natl Acad Sci U S A. Apr. 25, 2000;97(9):4525-9.

Plasterk et al. The silence of the genes. Curr Opin Genet Dev. Oct. 2000;10(5):562-7.

Pratt et al. Regulation of in vitro translation by double-stranded RNA in mammalian cell mRNA preparations. Nucleic Acids Res. Apr. 25, 1988;16(8):3497-510.

Proud. PKR: a new name and new roles. Trends Biochem Sci. Jun. 1995;20(6):241-6.

Ratcliff et al. A Similarity Between Viral Defense and Gene Silencing in Plants. Science. 1997;276:1558-60.

Rocheleau. Wnt signaling and an APC-related gene specify endoderm in early *C. elegans* embryos. Cell. Aug. 22, 1997;90(4):707-16.

Sanchez-Alvarado et al. Double-stranded RNA specifically disrupts gene expression during planarian regeneration. Proc Natl Acad Sci U S A. Apr. 27, 1999;96(9):5049-54.

Sawa et al. Components of the SWI/SNF complex are required for asymmetric cell division in *C. elegans*. Mol Cell. Sep. 2000;6(3):617-24.

Seydoux et al. Repression of gene expression in the embryonic germ lineage of *C. elegans*. Nature. Aug. 22, 1996;382(6593):713-6.

Sharp. RNAi and double-strand RNA. Genes Dev. Jan. 15, 1999;13(2):139-41.

Sharp et al. Molecular biology. RNA interference. Science. Mar. 31, 2000;287(5462):2431-3.

Shi et al. Genetic interference in *Trypanosoma brucei* by heritable and inducible double-stranded RNA. RNA. Jul. 2000;6(7):1069-76.

Shippy et al. Analysis of maxillopedia expression pattern and larval cuticular phenotype in wild-type and mutant tribolium. Genetics. Jun. 2000;155(2):721-31.

Stam et al. Annals of Botany. 1997;79:3-12.

Stauber et al. Function of bicoid and hunchback homologs in the basal cyclorrhaphan fly Megaselia (Phoridae). Proc Natl Acad Sci U S A. Sep. 26, 2000;97(20):10844-9.

Suzuki et al. Activation of target-tissue immnue-reception molecules by double-stranded polynucleotides. Proc Natl Acad Sci U S A. Mar. 2, 1999;96(5):2285-90.

Svoboda et al. Selective reduction of dormant maternal mRNAs in mouse oocytes by RNA interference. Development Oct. 2000;127(19):4147-56.

Tabara et al. RNAi in *C. elegans*: soaking in the genome sequence. Science. Oct. 16, 1998;282(5388):430-1.

Tabara et al. The rde-1 gene, RNA interference, and transposon silencing in *C. elegans*. Cell. Oct. 15, 1999;99(2):123-32.

Tabara et al. pos-1 encodes a cytoplasmic zinc-finger protein essential for germline specification in *C. elegans*. Development. Jan. 1999;126(1):1-11.

Tavernarakis et al. Heritable and inducible genetic interference by double-stranded RNA encoded by transgenes. Nat Genet. Feb. 2000;24(2):180-3.

Thompson. Shortcuts from gene sequence to function. Nat Biotechnol. Dec. 1999;17(12):1158-9.

Timmons et al. Specific interference by ingested dsRNA. Nature. Oct. 29, 1998;395(6705):854.

Tuschl et al. Targeted mRNA degradation by double-stranded RNA in vitro. Genes Dev. Dec. 15, 1999;13(24):3191-7.

Ui-Tei et al. Sensitive assay of RNA interference in Drosophila and Chinese hamster cultured cells using firefly luciferase gene as target. FEBS Lett. Aug. 18, 2000;479(3):79-82.

Wagner et al. Double-stranded RNA poses puzzle. Nature. Feb. 19. 1998;391(6669):744-5.

Wargelius et al. Double-stranded RNA induces specific developmental defects in zebrafish embryos. Biochem Biophys Res Commun. Sep. 16, 1999;263(1):156-61.

Waterhouse et al. Virus resistance and gene silencing in plants can be induced by simultaneous expression of sense and antisense RNA. Proc Natl Acad Sci U S A. 1998 10;95(23):13959-64.

Waterston et al. A Survey of expressed genes in *Caenorhabditis elegans*. Nat Genet. May 1992;1(2):114-23.

Wianny et al. Specific interference with gene function by double-stranded RNA in early mouse development. Nat Cell Biol Feb. 2000;2(2):70-5.

Willert et al. A Drosophila Axin homolog, Daxin, inhibits Wnt signaling. Development. Sep. 1999;126(18):4165-73.

Williams et al. ARGONAUTE1 is required for efficient RNA interference in Drosophila embryos. Proc Natl Acad Sci U S A May 14, 2002;99(10):6889-94.

Wilson et al. 2.2 Mb of contiguous nucleotide sequence from chromosome III of *C. elegans*. Nature. Mar. 3, 1994;368(6466):32-8.

Wu-Scharf et al. Transgene and transposon silencing in *Chlamydomonas reinhardtii* by a DEAH-box RNA helicase. Science. Nov. 10, 2000;290(5494):1159-62.

Yang et al. Evidence that processed small dsRNAs may mediate sequence-specific mRNA degradation during RNAi in Drosophila embryos. Curr Biol. Oct. 5, 2000;10(19):1191-200.

Zamore et al. RNAi: double-stranded RNA directs the ATP-dependent cleavage of mRNA at 21 to 23 nucleotide intervals. Cell. Mar. 31, 2000;101(1):25-33.

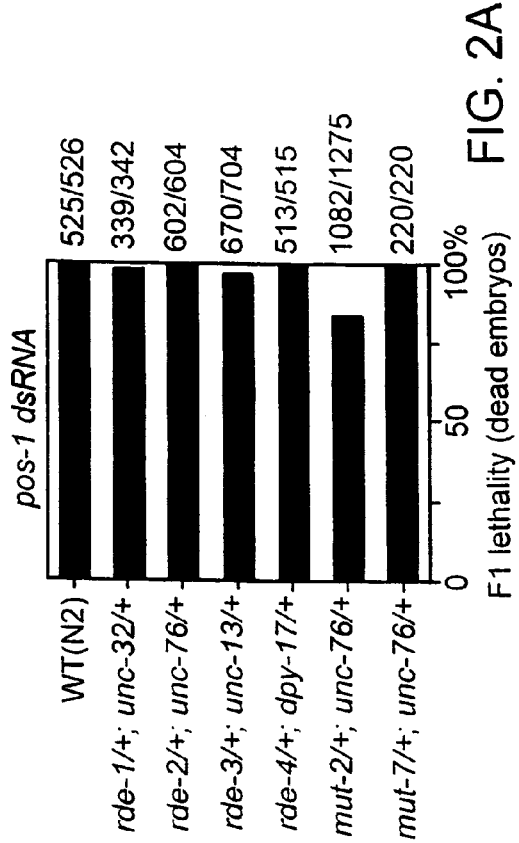
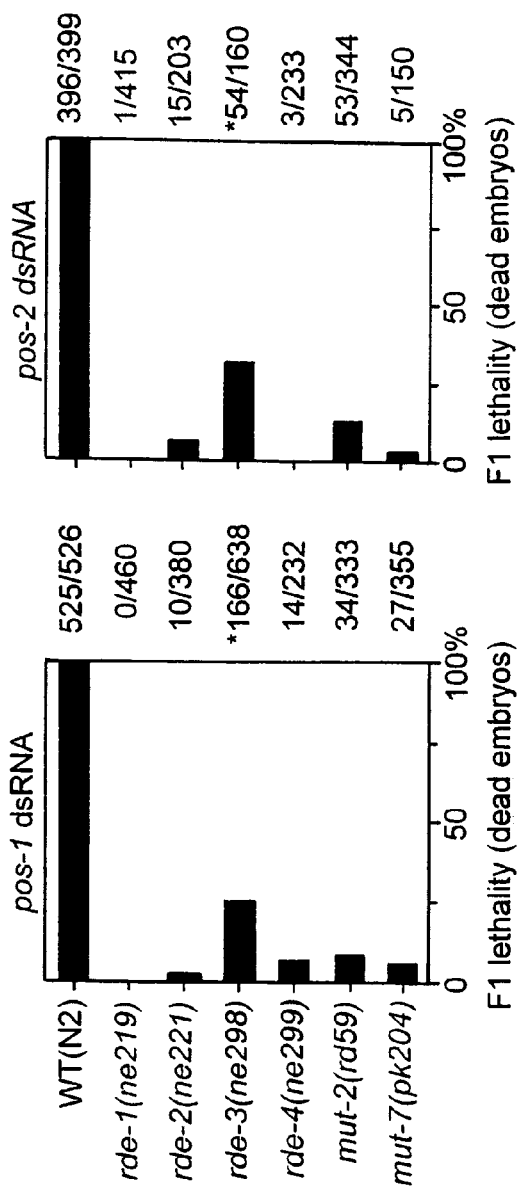
FIG. 2A
FIG. 2B

FIG. 4B-1

```
RDE-1    514  QLNVVPEKELCCAVEVVNETAGNPCLEENDVVKFYTELIGGKFRGIRTGANENRGAQSIMYDATKNEVAFYKNCTLNTGIGRFEIAATE
F48F7.1  581  RGKQFHTGFDVRVWAYACEAQ-QQHYKENDHRMFTNQLQRISNDAGMETVSNPCFCKNAVGVEQTEPMEKYTKQNTSG--------
eIF2C    392  RNKQTHTGIETKVWAIACFAP-QRQCTEVHLIKSFTEQLRKISRDAGMPIQGQPCFCKYAQGADSVGRMBRHLKNTDAG--------
ZWILLE   542  MNKTMINGMTVSRWACVNFS---RSVQENVARGECNELGQMCEVSGVEFNPEEVIPLLSARPDQVEKALKMVYHTSMNKTK-----
Sting    482  RTCSMFKNVHDNRWYVITPG---------RNLR--ETQEFVQMCIRTASSMRKVNICNPIVEEIPDDRNGTYSQAIDNAAAN----

RDE-1    604  AKNMFERLPDKEQKVLMFILISKRQLNAYGFVKHYCDHTIGVANQHITSETVTKALASLRHEKGSKRIFYQIALKINAKLGGINQELDWS
F48F7.1  658  ---------TQDYVYIRG-KFPYAEIVRKGPTYLGIAHQCVQAKNAIRTTP-----QTLSNLCLKVNKIGGVNSILPN
eIF2C    469  ---------LQDYVYIRG-KTPJYAEVVRKVGDLVLGMATQCVQMAIQNVQRTTP-----QTLSNLCLKINVKIGGVNNILPQ
ZWILLE   620  ---------GKELELLAILPDNNGSLYGDLKKICETELGLISQCCLTKHVFKISK-------QYLADVSLKINVKGGRNTVLVDA
Sting    552  ---------DPQIVMVVMRSPNEEKYSCIKKRTCVDRPVPSQVVLKVIAPRQQ--------KPTGLMSIATKVVIQMNAKLMGAP RDE-1    694  EIAEISPEEKERRKTMPLTMYVGIDVTHPTSYGIDYSIAAVVASINPGGT-IYRNMIVTQEECRPGERAVAHGRE----RTDILEAKFVK
F48F7.1  725  V--------RPRIFNEPVIFGCDITHPPAGDSRKPSIAAVVGSMDAHPE-RYAATYRVQHRQEITSDITY--------MVRE
eIF2C    536  G--------RPPVEQQPVIFLGRDVTHPPAGDGKKPSIAAVVGSMDAHPN-RYCATYRVQHRQEIIQDLA--------MVRE
ZWILLE   691  IS-------CRIPLVSDIPTTIEGRDVTHPENGEESSPSIAAVVASQDWPEVTKVKVGLVCAQAHPQELIQDEYKTWQDPVRGTVSGGMIRD
Sting    621  W--------QVVTPLHGLMTVGFDVCHSP--KNKNKSYGAFVATMDQKESFRLFSTVNEHIKGQELSEQMSVN--------MAC
```

```
cagccacaaagtgatgaaacatgtcctcgaattttcccgaattggaaaaaggatttatcgtcattctcgatccggta
tgatcaattattagcagctataagatatataagtttgatattaatattataggagatgaaatggcttgcgaggcccactg
gtaaatgcgacggcaaattctatgagaagaaagtacttcttttggtaaattggttcaagttctccagcaaattacgat
cgggaatactacgagtatgaagtgaaaatgacaaaggaagtattgaatagaaaaccagaaaacctttcccaaaaaag
agaaattccaatgtaagtgcttgtaaattagtcaaaactaattttattttcagtcccgatcgtgcaaaactcttctggc
aacatctcggcatgagagaagcagacagatttattctcgaagactatgttttgatgaaaaggacactgtttatagt
gtttgtcgactgaacactgtcacatcaaaaatgctggtttcggagaaagtagtaaaaattcacctgaactttagtgagaaatg
aaaggatttgggagaaaaatctatacacaatgatactacctatcgtaaaaattccttatgaaaacacgcattataacaaacaa
atccggaaaaagacgaagaagcgaatcggagttacaaattcctgaaggtttatgaacgagaggagattaaagtgtgagttgcaata
ttagctttcagaatgttatgaccagaaagttcgctacgcgccttttgtgaacgagaggagattaaagtgtgagttgcaata
ataataataatcacctcaactcattatatatttaagacaattcgcgaaaaatttgtgtacgataataattcaat
``` tctgcgagttcctgaatcgtttcacgatccaaacagattcgaacaatcattagaagtagcaccaagaatcgaagcatggt ttggaatttacattggaatcaaagaattgttcgatggtgaacctgtgctcaattttgcaagtaagtttgagaaactgcga taaaaaatcatgtgattttgttgaagttgtcgataaactattctacaatgcaccgaaaatgtctcttctggattatctt ctcctaattgtcgaccccagtcgtgtaacgatgatgtacgaaaagatcttaaaacaaaactgatggcgggaaaaatgac aatcagacaagccgcgcggccaagaattcgacaattattggaaaatttgaagctgaaatgcgcagaagtttgggataac aaatgttagtttaaattattcaaacaattaatatacaaattgattttcaggtcgagattgacagaacgacatctgacatt tctagatttgtgcgaggaaaactctcttgtttataaagtcactggtaaatcggacagaggaagaaatgcaaaaaagtacg atactacattgttcaaaatctatgaggaaaacaaaaagttcattgagtttccccacctaccactagtcaaagttaaaagt ggagcaaaagaatacgctgtaccaatggaacatcttgaagttcatgagaagccacaaagatacaagaatcgaattgatc ggtgatgcaagacaagtttctaaagcgagctacacgaaaacctcacgactacaaagaaaatacctaaaaatgctgaaa aattggatttctcttctgaagagctaaattttgttgaaagatttggattatgctccaaacttcagatgatcgaatgtcca ggaaaggttttgaaagagccaatgcttgtgaatagtgtaaatgaacaaattaaaatgacaccagtgattcgtggatttca agaaaaacaattgaatgtggttcccgaaaaagaactttgctgtgctgtttttgtagtcaacgaaacagcgggaaatccat gcttagaagagaacgacgttgtgtaagtgttttctacgtagattattccgaaatattttcagtaagttctacaccgaact aattggtggttgcaagttccgtggaatacgaattggtgccaatgaaaacagaggagcgcaatctattatgtacgacgcga cgaaaaatgaatatgccgtaagtttcagaaaattgaaagttttaaatatcatatttacagttctacaaaaattgtacac taaataccggaatcggtagatttgaaatagccgcaacagaagcgaagaatatgtttgaacgtcttcccgataaagaaca aaagtcttaatgttcattatcatttccaaacgacaactgaatgcttacggttttgtgaaacattattgcgatcacaccat cggtgtagctaatcagcatattacttctgaaacagtcacaaaagctttggcatcactaaggcacgagaaaggatcaaaac gaattttctatcaaattgcattgaaaatcaacgcgaaattaggaggtattaaccaggagcttgactggtcagaaattgca gaaatatcaccagaagaaaaagaaagacggaaaacaatgccattaactatgtatgttggaattgatgtaactcatccaa ctcctacagtggaattgattattctatagcggctgtagtagcgagtatcaatccaggtggaactatctatcgaaatatga ttgtgactcaagaagaatgtcgtcccggtgagcgtgcagtggctcatggacgggaagaacagatattttggaagcaaa ttcgtgaaattgctcagagaattcgcagaagtgagttgtcttgagtatttaaaagatctctgggattttaatttttttg

FIG. 5B taaactttcagaacaacgacaatcgagcaccagccgcatatttgtagtctatcgagacggagttagcgattcggagatgcta cgtgttagtcatgatgagcttcgatctttaaaaagcgaagtaaacaattcatgtcggaacggatggagaagatccaga gccgaagtacacgttcattgtgattcagaaaagacacaatacacgattgcttcgaagaatgaaaaagataagccagtg tcaataagatcttactcctgctgaaacagtgtcgctgttaaacaatgggaggaggatatgaaagaaagc aagaaactggaacccatcatccggaacaactgtggatataactatcgtttcgaaatacaaattcgattttt cttggcatctcatcatggtgtccttggtacatctcgtccaggacattacactgttatgtgacgataaaggaatgagcc aagatgaagtctatgtaagcgtttgaatagcagtagcgattttagggattttgtaatccgcatatagttatatagaaa aatgtttcagaaaatgacctacggactgctttctctctgctagatgtcgaaaaacccatctcgttgccgttccggttc attatgctcatttatcatgtgaaaagcgaaagagcttatcgaacttacaaggaacattacatcggtgactatgcacag ccacggactcgacacgaaatggaacatttctccaaactaacgtgaagtaccctggaatgtcgttcgcataacatttgc aaaagtgtcgcccgtttcaatcaaattttcaattgtagatattgtactacttttttaaagcccggtttcaaaaatt cattccatgactaacgttttcataattacttgaaatt (SEQ ID NO:1)

FIG. 5C

CAGCCACAAAGTGATGAAAC- 5' UTR

1/1                                       31/11
ATG TCC TCG AAT TTT CCC GAA TTG GAA AAA GGA TTT TAT CGT CAT TCT CTC GAT CCG GAG
Met ser ser asn phe pro glu leu glu lys gly phe tyr arg his ser leu asp pro glu 61/21                                     91/31
ATG AAA TGG CTT GCG AGG CCC ACT GGT AAA TGC GAC GGC AAA TTC TAT GAG AAG AAA GTA
met lys trp leu ala arg pro thr gly lys cys asp gly lys phe tyr glu lys lys val 121/41                                    151/51
CTT CTT TTG GTA AAT TGG TTC AAG TTC TCC AGC AAA ATT TAC GAT CGG GAA TAC TAC GAG
leu leu leu val asn trp phe lys phe ser ser lys ile tyr asp arg glu tyr tyr glu 181/61                                    211/71
TAT GAA GTG AAA ATG ACA AAG GAA GTA TTG AAT AGA AAA CCA GGA AAA CCT TTC CCA AAA
tyr glu val lys met thr lys glu val leu asn arg lys pro gly lys pro phe pro lys 241/81                                    271/91
AAG ACA GAA ATT CCA ATT CCC GAT CGT GCA AAA CTC TTC TGG CAA CAT CTT CGG CAT GAG
lys thr glu ile pro ile pro asp arg ala lys leu phe trp gln his leu arg his glu 301/101                                   331/111
AAG AAG CAG ACA GAT TTT ATT CTC GAA GAC TAT GTT TTT GAT GAA AAG GAC ACT GTT TAT
lys lys gln thr asp phe ile leu glu asp tyr val phe asp glu lys asp thr val tyr 361/121                                   391/131
AGT GTT TGT CGA CTG AAC ACT GTC ACA TCA AAA ATG CTG GTT TCG GAG AAA GTA GTA AAA
ser val cys arg leu asn thr val thr ser lys met leu val ser glu lys val val lys 421/141                                   451/151
AAG GAT TCG GAG AAA AAA GAT GAA AAG GAT TTG GAG AAA AAA ATC TTA TAC ACA ATG ATA
lys asp ser glu lys lys asp glu lys asp leu glu lys lys ile leu tyr thr met ile 481/161                                   511/171
CTT ACC TAT CGT AAA AAA TTT CAC CTG AAC TTT AGT CGA GAA AAT CCG GAA AAA GAC GAA
leu thr tyr arg lys lys phe his leu asn phe ser arg glu asn pro glu lys asp glu 541/181                                   571/191
GAA GCG AAT CGG AGT TAC AAA TTC CTG AAG AAT GTT ATG ACC CAG AAA GTT CGC TAC GCG
glu ala asn arg ser tyr lys phe leu lys asn val met thr gln lys val arg tyr ala 601/201                                   631/211
CCT TTT GTG AAC GAG GAG ATT AAA GTA CAA TTC GCG AAA AAT TTT GTG TAC GAT AAT AAT
pro phe val asn glu glu ile lys val gln phe ala lys asn phe val tyr asp asn asn 661/221                                   691/231
TCA ATT CTG CGA GTT CCT GAA TCG TTT CAC GAT CCA AAC AGA TTC GAA CAA TCA TTA GAA
ser ile leu arg val pro glu ser phe his asp pro asn arg phe glu gln ser leu glu

```
GTA GCA CCA AGA ATC GAA GCA TGG TTT GGA ATT TAC ATT GGA ATC AAA GAA TTG TTC GAT
val ala pro arg ile glu ala trp phe gly ile tyr ile gly ile lys glu leu phe asp 781/261                                    811/271
GGT GAA CCT GTG CTC AAT TTT GCA ATT GTC GAT AAA CTA TTC TAC AAT GCA CCG AAA ATG
gly glu pro val leu asn phe ala ile val asp lys leu phe tyr asn ala pro lys met 841/281                                    871/291
TCT CTT CTG GAT TAT CTT CTC CTA ATT GTC GAC CCC CAG TCG TGT AAC GAT GAT GTA CGA
ser leu leu asp tyr leu leu leu ile val asp pro gln ser cys asn asp asp val arg 901/301                                    931/311
AAA GAT CTT AAA ACA AAA CTG ATG GCG GGA AAA ATG ACA ATC AGA CAA GCC GCG CGG CCA
lys asp leu lys thr lys leu met ala gly lys met thr ile arg gln ala ala arg pro 961/321                                    991/331
AGA ATT CGA CAA TTA TTG GAA AAT TTG AAG CTG AAA TGC GCA GAA GTT TGG GAT AAC GAA
arg ile arg gln leu leu glu asn leu lys leu lys cys ala glu val trp asp asn glu 1021/341                                   1051/351
ATG TCG AGA TTG ACA GAA CGA CAT CTG ACA TTT CTA GAT TTG TGC GAG GAA AAC TCT CTT
met ser arg leu thr glu arg his leu thr phe leu asp leu cys glu glu asn ser leu 1081/361                                   1111/371
GTT TAT AAA GTC ACT GGT AAA TCG GAC AGA GGA AGA AAT GCA AAA AAG TAC GAT ACT ACA
val tyr lys val thr gly lys ser asp arg gly arg asn ala lys lys tyr asp thr thr 1141/381                                   1171/391
TTG TTC AAA ATC TAT GAG GAA AAC AAA AAG TTC ATT GAG TTT CCC CAC CTA CCA CTA GTC
leu phe lys ile tyr glu glu asn lys lys phe ile glu phe pro his leu pro leu val 1201/401                                   1231/411
AAA GTT AAA AGT GGA GCA AAA GAA TAC GCT GTA CCA ATG GAA CAT CTT GAA GTT CAT GAG
lys val lys ser gly ala lys glu tyr ala val pro met glu his leu glu val his glu 1261/421                                   1291/431
AAG CCA CAA AGA TAC AAG AAT CGA ATT GAT CTG GTG ATG CAA GAC AAG TTT CTA AAG CGA
lys pro gln arg tyr lys asn arg ile asp leu val met gln asp lys phe leu lys arg 1321/441                                   1351/451
GCT ACA CGA AAA CCT CAC GAC TAC AAA GAA AAT ACC CTA AAA ATG CTG AAA GAA TTG GAT
ala thr arg lys pro his asp tyr lys glu asn thr leu lys met leu lys glu leu asp 1381/461                                   1411/471
TTC TCT TCT GAA GAG CTA AAT TTT GTT GAA AGA TTT GGA TTA TGC TCC AAA CTT CAG ATG
phe ser ser glu glu leu asn phe val glu arg phe gly leu cys ser lys leu gln met 1441/481                                   1471/491
ATC GAA TGT CCA GGA AAG GTT TTG AAA GAG CCA ATG CTT GTG AAT AGT GTA AAT GAA CAA
ile glu cys pro gly lys val leu lys glu pro met leu val asn ser val asn glu gln 1501/501                                   1531/511
ATT AAA ATG ACA CCA GTG ATT CGT GGA TTT CAA GAA AAA CAA TTG AAT GTG GTT CCC GAA
ile lys met thr pro val ile arg gly phe gln glu lys gln leu asn val val pro glu
```

FIG. 6B

```
1561/521                              1591/531
AAA GAA CTT TGC TGT GCT GTT TTT GTA GTC AAC GAA ACA GCG GGA AAT CCA TGC TTA GAA
lys glu leu cys cys ala val phe val val asn glu thr ala gly asn pro cys leu glu 1621/541                              1651/551
GAG AAC GAC GTT GTT AAG TTC TAC ACC GAA CTA ATT GGT GGT TGC AAG TTC CGT GGA ATA
glu asn asp val val lys phe tyr thr glu leu ile gly gly cys lys phe arg gly ile 1681/561                              1711/571
CGA ATT GGT GCC AAT GAA AAC AGA GGA GCG CAA TCT ATT ATG TAC GAC GCG ACG AAA AAT
arg ile gly ala asn glu asn arg gly ala gln ser ile met tyr asp ala thr lys asn 1741/581                              1771/591
GAA TAT GCC TTC TAC AAA AAT TGT ACA CTA AAT ACC GGA ATC GGT AGA TTT GAA ATA GCC
glu tyr ala phe tyr lys asn cys thr leu asn thr gly ile gly arg phe glu ile ala 1801/601                              1831/611
GCA ACA GAA GCG AAG AAT ATG TTT GAA CGT CTT CCC GAT AAA GAA CAA AAA GTC TTA ATG
ala thr glu ala lys asn met phe glu arg leu pro asp lys glu gln lys val leu met 1861/621                              1891/631
TTC ATT ATC ATT TCC AAA CGA CAA CTG AAT GCT TAC GGT TTT GTG AAA CAT TAT TGC GAT
phe ile ile ile ser lys arg gln leu asn ala tyr gly phe val lys his tyr cys asp 1921/641                              1951/651
CAC ACC ATC GGT GTA GCT AAT CAG CAT ATT ACT TCT GAA ACA GTC ACA AAA GCT TTG GCA
his thr ile gly val ala asn gln his ile thr ser glu thr val thr lys ala leu ala 1981/661                              2011/671
TCA CTA AGG CAC GAG AAA GGA TCA AAA CGA ATT TTC TAT CAA ATT GCA TTG AAA ATC AAC
ser leu arg his glu lys gly ser lys arg ile phe tyr gln ile ala leu lys ile asn 2041/681                              2071/691
GCG AAA TTA GGA GGT ATT AAC CAG GAG CTT GAC TGG TCA GAA ATT GCA GAA ATA TCA CCA
ala lys leu gly gly ile asn gln glu leu asp trp ser glu ile ala glu ile ser pro 2101/701                              2131/711
GAA GAA AAA GAA AGA CGG AAA ACA ATG CCA TTA ACT ATG TAT GTT GGA ATT GAT GTA ACT
glu glu lys glu arg arg lys thr met pro leu thr met tyr val gly ile asp val thr 2161/721                              2191/731
CAT CCA ACC TCC TAC AGT GGA ATT GAT TAT TCT ATA GCG GCT GTA GTA GCG AGT ATC AAT
his pro thr ser tyr ser gly ile asp tyr ser ile ala ala val val ala ser ile asn 2221/741                              2251/751
CCA GGT GGA ACT ATC TAT CGA AAT ATG ATT GTG ACT CAA GAA GAA TGT CGT CCC GGT GAG
pro gly gly thr ile tyr arg asn met ile val thr gln glu glu cys arg pro gly glu 2281/761                              2311/771
CGT GCA GTG GCT CAT GGA CGG GAA AGA ACA GAT ATT TTG GAA GCA AAG TTC GTG AAA TTG
arg ala val ala his gly arg glu arg thr asp ile leu glu ala lys phe val lys leu 2341/781                              2371/791
TTC AGA GAA TTC GCA GAA AAC AAC GAC AAT CGA GCA CCA GCG CAT ATT GTA GTC TAT CGA
leu arg glu phe ala glu asn asn asp asn arg ala pro ala his ile val val tyr arg
```

FIG. 6C

```
2401/801                                    2431/811
GAC GGA GTT AGC GAT TCG GAG ATG CTA CGT GTT AGT CAT GAT GAG CTT CGA TCT TTA AAA
asp gly val ser asp ser glu met leu arg val ser his asp glu leu arg ser leu lys 2461/821                                    2491/831
AGC GAA GTA AAA CAA TTC ATG TCG GAA CGG GAT GGA GAA GAT CCA GAG CCG AAG TAC ACG
ser glu val lys gln phe met ser glu arg asp gly glu asp pro glu pro lys tyr thr 2521/841                                    2551/851
TTC ATT GTG ATT CAG AAA AGA CAC AAT ACA CGA TTG CTT CGA AGA ATG GAA AAA GAT AAG
phe ile val ile gln lys arg his asn thr arg leu leu arg arg met glu lys asp lys 2581/861                                    2611/871
CCA GTG GTC AAT AAA GAT CTT ACT CCT GCT GAA ACA GAT GTC GCT GTT GCT GCT GTT AAA
pro val val asn lys asp leu thr pro ala glu thr asp val ala val ala ala val lys 2641/881                                    2671/891
CAA TGG GAG GAG GAT ATG AAA GAA AGC AAA GAA ACT GGA ATT GTG AAC CCA TCA TCC GGA
gln trp glu glu asp met lys glu ser lys glu thr gly ile val asn pro ser ser gly 2701/901                                    2731/911
ACA ACT GTG GAT AAA CTT ATC GTT TCG AAA TAC AAA TTC GAT TTT TTC TTG GCA TCT CAT
thr thr val asp lys leu ile val ser lys tyr lys phe asp phe phe leu ala ser his 2761/921                                    2791/931
CAT GGT GTC CTT GGT ACA TCT CGT CCA GGA CAT TAC ACT GTT ATG TAT GAC GAT AAA GGA
his gly val leu gly thr ser arg pro gly his tyr thr val met tyr asp asp lys gly 2821/941                                    2851/951
ATG AGC CAA GAT GAA GTC TAT AAA ATG ACC TAC GGA CTT GCT TTT CTC TCT GCT AGA TGT
met ser gln asp glu val tyr lys met thr tyr gly leu ala phe leu ser ala arg cys 2881/961                                    2911/971
CGA AAA CCC ATC TCG TTG CCT GTT CCG GTT CAT TAT GCT CAT TTA TCA TGT GAA AAA GCG
arg lys pro ile ser leu pro val pro val his tyr ala his leu ser cys glu lys ala 2941/981                                    2971/991
AAA GAG CTT TAT CGA ACT TAC AAG GAA CAT TAC ATC GGT GAC TAT GCA CAG CCA CGG ACT
lys glu leu tyr arg thr tyr lys glu his tyr ile gly asp tyr ala gln pro arg thr 3001/1001                                   3031/1011
CGA CAC GAA ATG GAA CAT TTT CTC CAA ACT AAC GTG AAG TAC CCT GGA ATG TCG TTC GCA
arg his glu met glu his phe leu gln thr asn val lys tyr pro gly met ser phe ala 3061/1021                                   3091/1031
TAA CAT TTT GCA AAA GTG TCG CCC GTT TCA ATC AAA TTT TTC AAT TGT AGA TAT TGT ACT
OCH (SEQ ID NO:3)

3121/1041                                   3151/1051
TAC TTT TTT TTA AAG CCC GGT TTC AAA AAT TCA TTC CAT GAC TAA CGT TTT CAT AAA TTA

3181/1061
CTT GAA ATT TAA AAA AAA AAA AAA AAA (SEQ ID NO:2)
```

FIG. 6D

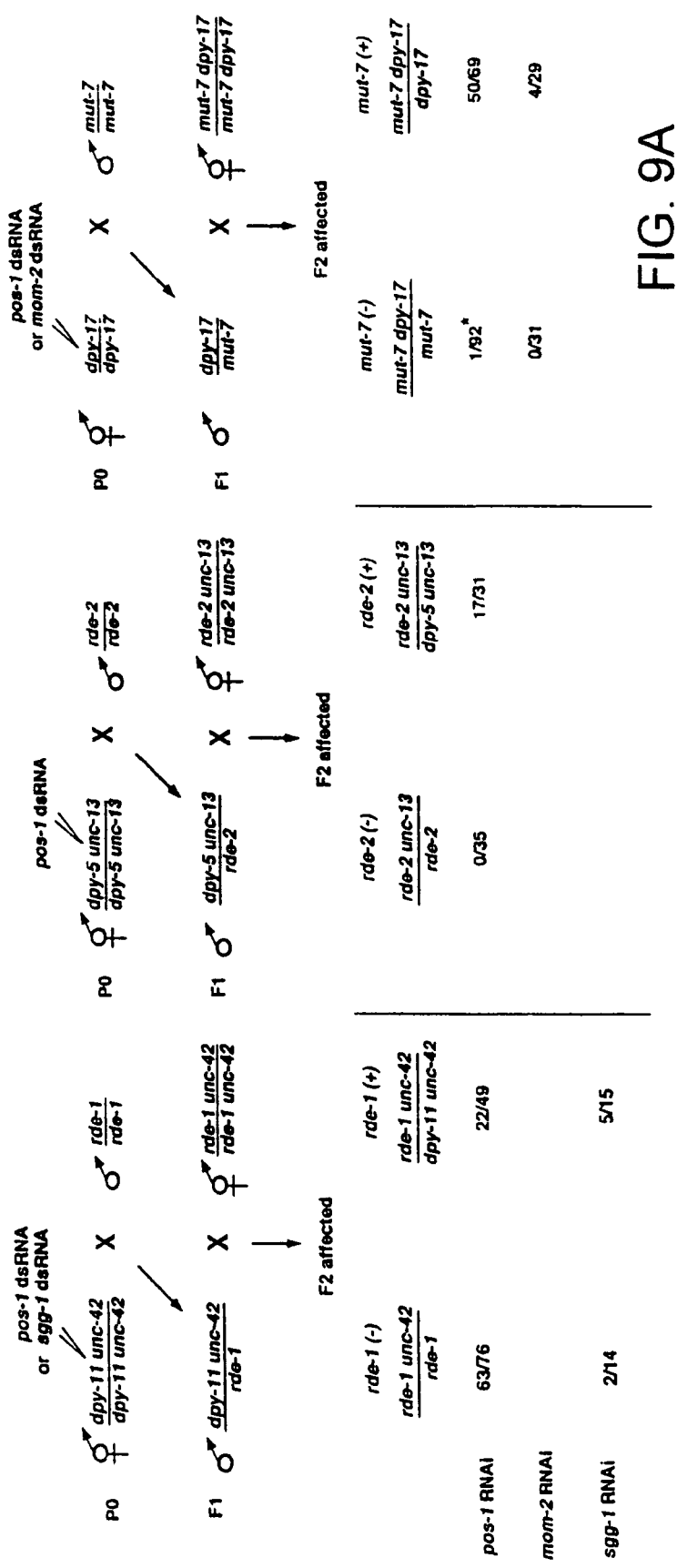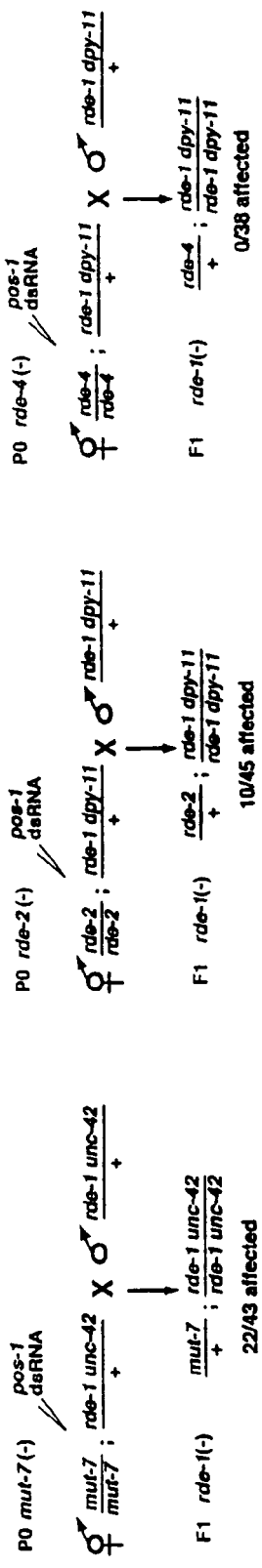
FIG. 9A
FIG. 9B

```
         10        20        30        40        50        60
ATGGATTTAACCAAACTAACGTTTGAAAGCGTTTTCGGTGGATCAGATGTTCCTATGAAG
 M  D  L  T  K  L  T  F  E  S  V  F  G  G  S  D  V  P  M  K 70        80        90       100       110       120
CCTTCCCGATCGGAGGATAACAAAACGCCAAGAAACAGAACAGATTTGGAGATGTTTCTG
 P  S  R  S  E  D  N  K  T  P  R  N  R  T  D  L  E  M  F  L 130       140       150       160       170       180
AAGAAAACTCCCCTCATGGTACTAGAAGAGGCTGCTAAGGCTGTCTATCAAAAGACGCCA
 K  K  T  P  L  M  V  L  E  E  A  A  K  A  V  Y  Q  K  T  P 190       200       210       220       230       240
ACTTGGGGCACTGTCGAACTTCCTGAAGGCTTCGAGATGACGTTGATTCTGAATGAAATT
 T  W  G  T  V  E  L  P  E  G  F  E  M  T  L  I  L  N  E  I 250       260       270       280       290       300
ACTGTAAAAGGCCAGGCAACAAGCAAGAAAGCTGCGAGACAAAAGGCTGCTGTTGAATAT
 T  V  K  G  Q  A  T  S  K  K  A  A  R  Q  K  A  A  V  E  Y 310       320       330       340       350       360
TTACGCAAGGTTGTGGAGAAAGGAAAGCACGAAATCTTTTTCATTCCTGGAACAACCAAA
 L  R  K  V  V  E  K  G  K  H  E  I  F  F  I  P  G  T  T  K 370       380       390       400       410       420
GAAGAAGCTCTTTCGAATATTGATCAAATATCGGATAAGGCTGAGGAATTGAAACGATCA
 E  E  A  L  S  N  I  D  Q  I  S  D  K  A  E  E  L  K  R  S 430       440       450       460       470       480
ACTTCAGATGCTGTTCAGGATAACGATAACGATGATTCGATTCCTACAAGTGCTGAATTT
 T  S  D  A  V  Q  D  N  D  N  D  D  S  I  P  T  S  A  E  F 490       500       510       520       530       540
CCACCTGGTATTTCGCCAACCGAGAATTGGGTCGGAAAGTTGCAGGAAAAATCTCAAAAA
 P  P  G  I  S  P  T  E  N  W  V  G  K  L  Q  E  K  S  Q  K 550       560       570       580       590       600
AGCAAGCTGCAAGCCCCAATCTATGAAGATTCCAAGAATGAGAGAACCGAGCGTTTCTTG
 S  K  L  Q  A  P  I  Y  E  D  S  K  N  E  R  T  E  R  F  L 610       620       630       640       650       660
GTTATATGCACGATGTGCAATCAAAAAACCAGAGGAATCAGAAGTAAGAAGAAGGACGCA
 V  I  C  T  M  C  N  Q  K  T  R  G  I  R  S  K  K  K  D  A 670       680       690       700       710       720
AAGAATCTTGCAGCATGGTTGATGTGGAAAGCGTTGGAAGACGGTATCGAATCTCTGGAA
 K  N  L  A  A  W  L  M  W  K  A  L  E  D  G  I  E  S  L  E 730       740       750       760       770       780
TCATATGATATGGTTGATGTGATTGAAAATTTGGAAGAAGCTGAACATTTACTCGAAATT
 S  Y  D  M  V  D  V  I  E  N  L  E  E  A  E  H  L  L  E  I
```

FIG. 10A

```
       790        800        810        820        830        840
CAGGATCAAGCATCCAAGATTAAAGACAAGCATTCCGCACTGATTGATATACTCTCGGAC
 Q  D  Q  A  S  K  I  K  D  K  H  S  A  L  I  D  I  L  S  D 850        860        870        880        890        900
AAGAAAAGATTTTCAGACTACAGCATGGATTTCAACGTATTATCAGTGAGCACAATGGGA
 K  K  R  F  S  D  Y  S  M  D  F  N  V  L  S  V  S  T  M  G 910        920        930        940        950        960
ATACATCAGGTGCTATTGGAAATCTCGTTCCGGCGTCTAGTTTCTCCAGACCCCGACGAT
 I  H  Q  V  L  L  E  I  S  F  R  R  L  V  S  P  D  P  D  D 970        980        990       1000       1010       1020
TTGGAAATGGGAGCAGAACACACCCAGACTGAAGAAATTATGAAGGCTACTGCCGAGAAG
 L  E  M  G  A  E  H  T  Q  T  E  E  I  M  K  A  T  A  E  K 1030       1040       1050       1060       1070       1080
GAAAAGCTACGGAAGAAGAATATGCCAGATTCCGGGCCGCTAGTGTTTGCTGGACATGGT
 E  K  L  R  K  K  N  M  P  D  S  G  P  L  V  F  A  G  H  G 1090       1100       1110       1120       1130       1140
TCATCGGCGGAAGAGGCTAAACAGTGTGCTTGTAAATCGGCGATTATCCATTTCAACACC
 S  S  A  E  E  A  K  Q  C  A  C  K  S  A  I  I  H  F  N  T 1150       1160       1170       1180       1190       1200
TATGATTTCACGGATTGAAAATATTATTGCGTATTCCTGAAAAATGAAGCGTCTGAATGA
 Y  D  F  T  D  *  K  Y  Y  C  V  F  L  K  N  E  A  S  E  *

1210       1220       1230
TTATAAAAAAAAAAAAAAAAAAA            (SEQ ID NO:4)
 L  *  K  K  K  K  K               (SEQ ID NO:5)
```

FIG. 10B

SEQUENCE LISTING

<160> NUMBER OF SEQ ID NOS: 14

<210> SEQ ID NO 1
<211> LENGTH: 3719

<212> TYPE: DNA
<213> ORGANISM: Caenorhabditis elegans

<400> SEQUENCE: 1

| | | | | | |
|---|---|---|---|---|---:|
| cagccacaaa | gtgatgaaac | atgtcctcga | attttcccga | attggaaaaa | ggattttatc | 60 |
| gtcattctct | cgatccggta | tgatcaatta | ttagcagcta | aagatatat | aagtttgata | 120 |
| ttaatattat | aggagatgaa | atggcttgcg | aggcccactg | gtaaatgcga | cggcaaattc | 180 |
| tatgagaaga | aagtacttct | tttggtaaat | tggttcaagt | tctccagcaa | aatttacgat | 240 |
| cgggaatact | acgagtatga | agtgaaaatg | acaaaggaag | tattgaatag | aaaaccagga | 300 |
| aaacctttcc | caaaaaagac | agaaattcca | atgtaagtgc | ttgtaaatta | gtcaaaacta | 360 |
| atttttatttt | tcagtcccga | tcgtgcaaaa | ctcttctggc | aacatcttcg | gcatgagaag | 420 |
| aagcagacag | atttattct | cgaagactat | gtttttgatg | aaaaggacac | tgtttatagt | 480 |
| gtttgtcgac | tgaacactgt | cacatcaaaa | atgctggttt | cggagaaagt | agtaaaaaag | 540 |
| gattcggaga | aaaagatga | aaaggattg | gagaaaaaaa | tcttatacac | aatgatactt | 600 |
| acctatcgta | aaaatttca | cctgaacttt | agtcgagaaa | atccggaaaa | agacgaagaa | 660 |
| gcgaatcgga | gttacaaatt | cctgaaggtt | tatgaaaaac | acgcattata | caaacaaaa | 720 |
| ttagctttca | gaatgttatg | acccagaaag | ttcgctacgc | gccttttgtg | aacgaggaga | 780 |
| ttaaagtgtg | agttgcaata | ataataataa | taatcacctc | aactcattta | tatattttaa | 840 |
| gacaattcgc | gaaaaatttt | gtgtacgata | ataattcaat | tctgcgagtt | cctgaatcgt | 900 |
| ttcacgatcc | aaacagattc | gaacaatcat | tagaagtagc | accaagaatc | gaagcatggt | 960 |
| ttggaattta | cattggaatc | aaagaattgt | tcgatggtga | acctgtgctc | aattttgcaa | 1020 |
| gtaagtttga | gaaactgcga | taaaaaatca | tgtgattttt | gttgaagttg | tcgataaact | 1080 |
| attctacaat | gcaccgaaaa | tgtctcttct | ggattatctt | ctcctaattg | tcgaccccca | 1140 |
| gtcgtgtaac | gatgatgtac | gaaaagatct | taaaacaaaa | ctgatggcgg | gaaaaatgac | 1200 |
| aatcagacaa | gccgcgcggc | caagaattcg | acaattattg | gaaaatttga | agctgaaatg | 1260 |
| cgcagaagtt | tgggataacg | aaatgttagt | ttaaattatt | caaacaatta | atatacaaat | 1320 |
| tgattttcag | gtcgagattg | acagaacgac | atctgacatt | tctagatttg | tgcgaggaaa | 1380 |
| actctcttgt | ttataaagtc | actggtaaat | cggacagagg | aagaaatgca | aaaaagtacg | 1440 |
| atactacatt | gttcaaaatc | tatgaggaaa | acaaaaagtt | cattgagttt | ccccacctac | 1500 |
| cactagtcaa | agttaaaagt | ggagcaaaag | aatacgctgt | accaatggaa | catcttgaag | 1560 |
| ttcatgagaa | gccacaaaga | tacaagaatc | gaattgatct | ggtgatgcaa | gacaagtttc | 1620 |
| taaagcgagc | tacacgaaaa | cctcacgact | acaaagaaaa | taccctaaaa | atgctgaaag | 1680 |
| aattggattt | ctcttctgaa | gagctaaatt | ttgttgaaag | atttggatta | tgctccaaac | 1740 |
| ttcagatgat | cgaatgtcca | ggaaaggttt | tgaaagagcc | aatgcttgtg | aatagtgtaa | 1800 |
| atgaacaaat | taaatgaca | ccagtgattc | gtggatttca | agaaaaacaa | ttgaatgtgg | 1860 |
| ttcccgaaaa | agaactttgc | tgtgctgttt | ttgtagtcaa | cgaaacagcg | ggaaatccat | 1920 |
| gcttagaaga | gaacgacgtt | gtgtaagtgt | tttctacgta | gattattccg | aaatattttc | 1980 |
| agtaagttct | acaccgaact | aattggtggt | tgcaagttcc | gtggaatacg | aattggtgcc | 2040 |
| aatgaaaaca | gaggagcgca | atctattatg | tacgacgcga | cgaaaatga | atatgccgta | 2100 |
| agtttcagaa | aattgaaagt | ttttaaatat | catatttaca | gttctacaaa | aattgtacac | 2160 |
| taaataccgg | aatcggtaga | tttgaaatag | ccgcaacaga | agcgaagaat | atgtttgaac | 2220 |

```
gtcttcccga taaagaacaa aaagtcttaa tgttcattat catttccaaa cgacaactga   2280
atgcttacgg ttttgtgaaa cattattgcg atcacaccat cggtgtagct aatcagcata   2340
ttacttctga acagtcaca aaagctttgg catcactaag gcacgagaaa ggatcaaaac    2400
gaattttcta tcaaattgca ttgaaaatca acgcgaaatt aggaggtatt aaccaggagc   2460
ttgactggtc agaaattgca gaaatatcac cagaagaaaa agaaagacgg aaacaatgc    2520 cattaactat gtatgttgga attgatgtaa ctcatccaac ctcctacagt ggaattgatt   2580
attctatagc ggctgtagta gcgagtatca atccaggtgg aactatctat cgaaatatga   2640
ttgtgactca agaagaatgt cgtcccggtg agcgtgcagt ggctcatgga cgggaaagaa   2700
cagatatttt ggaagcaaag ttcgtgaaat tgctcagaga attcgcagaa gtgagttgtc   2760
ttgagtattt aaaagatctc tgggattttt aattttttg taaactttca gaacaacgac    2820
aatcgagcac cagcgcatat tgtagtctat cgagacggag ttagcgattc ggagatgcta   2880
cgtgttagtc atgatgagct tcgatcttta aaaagcgaag taaacaatt catgtcggaa    2940 cgggatggag aagatccaga gccgaagtac acgttcattg tgattcagaa agacacaat    3000 acacgattgc ttcgaagaat ggaaaaagat aagccagtgg tcaataaaga tcttactcct   3060
gctgaaacag atgtcgctgt tgctgctgtt aaacaatggg aggaggatat gaaagaaagc   3120
aaagaaactg gaattgtgaa cccatcatcc ggaacaactg tggataaact tatcgtttcg   3180
aaatacaaat tcgattttt cttggcatct catcatggtg tccttggtac atctcgtcca    3240
ggacattaca ctgttatgta tgacgataaa ggaatgagcc aagatgaagt ctatgtaagc   3300
gttttgaata gcagttagcg attttaggat tttgtaatcc gcatatagtt attataaaaa    3360
aatgtttcag aaaatgacct acggacttgc ttttctctct gctagatgtc gaaaacccat   3420
ctcgttgcct gttccggttc attatgctca tttatcatgt gaaaaagcga aagagcttta   3480
tcgaacttac aaggaacatt acatcggtga ctatgcacag ccacggactc gacacgaaat   3540
ggaacatttt ctccaaacta acgtgaagta ccctggaatg tcgttcgcat aacattttgc   3600
aaaagtgtcg cccgtttcaa tcaaattttt caattgtaga tattgtactt actttttttt   3660
aaagcccggt ttcaaaaatt cattccatga ctaacgtttt cataaattac ttgaaatttt   3719

<210> SEQ ID NO 2
<211> LENGTH: 3227
<212> TYPE: DNA
<213> ORGANISM: Caenorhabditis elegans
<220> FEATURE:
<221> NAME/KEY: CDS
<222> LOCATION: (21)...(3080)

<400> SEQUENCE: 2
cagccacaaa gtgatgaaac atg tcc tcg aat ttt ccc gaa ttg gaa aaa gga   53
                      Met Ser Ser Asn Phe Pro Glu Leu Glu Lys Gly
                       1               5                       10 ttt tat cgt cat tct ctc gat ccg gag atg aaa tgg ctt gcg agg ccc   101
Phe Tyr Arg His Ser Leu Asp Pro Glu Met Lys Trp Leu Ala Arg Pro
            15                  20                  25 act ggt aaa tgc gac ggc aaa ttc tat gag aag aaa gta ctt ctt ttg   149
Thr Gly Lys Cys Asp Gly Lys Phe Tyr Glu Lys Lys Val Leu Leu Leu
        30                  35                  40 gta aat tgg ttc aag ttc tcc agc aaa att tac gat cgg gaa tac tac   197
Val Asn Trp Phe Lys Phe Ser Ser Lys Ile Tyr Asp Arg Glu Tyr Tyr
     45                  50                  55 gag tat gaa gtg aaa atg aca aag gaa gta ttg aat aga aaa cca gga   245
Glu Tyr Glu Val Lys Met Thr Lys Glu Val Leu Asn Arg Lys Pro Gly
```

-continued

```
                60                   65                   70                  75
aaa cct ttc cca aaa aag aca gaa att cca att ccc gat cgt gca aaa       293
Lys Pro Phe Pro Lys Lys Thr Glu Ile Pro Ile Pro Asp Arg Ala Lys
                    80                  85                  90 ctc ttc tgg caa cat ctt cgg cat gag aag aag cag aca gat ttt att       341
Leu Phe Trp Gln His Leu Arg His Glu Lys Lys Gln Thr Asp Phe Ile
                95                  100                 105 ctc gaa gac tat gtt ttt gat gaa aag gac act gtt tat agt gtt tgt       389
Leu Glu Asp Tyr Val Phe Asp Glu Lys Asp Thr Val Tyr Ser Val Cys
            110                 115                 120 cga ctg aac act gtc aca tca aaa atg ctg gtt tcg gag aaa gta gta       437
Arg Leu Asn Thr Val Thr Ser Lys Met Leu Val Ser Glu Lys Val Val
        125                 130                 135 aaa aag gat tcg gag aaa aaa gat gaa aag gat ttg gag aaa aaa atc       485
Lys Lys Asp Ser Glu Lys Lys Asp Glu Lys Asp Leu Glu Lys Lys Ile
140                 145                 150                 155 tta tac aca atg ata ctt acc tat cgt aaa aaa ttt cac ctg aac ttt       533
Leu Tyr Thr Met Ile Leu Thr Tyr Arg Lys Lys Phe His Leu Asn Phe
                160                 165                 170 agt cga gaa aat ccg gaa aaa gac gaa gaa gcg aat cgg agt tac aaa       581
Ser Arg Glu Asn Pro Glu Lys Asp Glu Glu Ala Asn Arg Ser Tyr Lys
            175                 180                 185 ttc ctg aag aat gtt atg acc cag aaa gtt cgc tac gcg cct ttt gtg       629
Phe Leu Lys Asn Val Met Thr Gln Lys Val Arg Tyr Ala Pro Phe Val
        190                 195                 200 aac gag gag att aaa gta caa ttc gcg aaa aat ttt gtg tac gat aat       677
Asn Glu Glu Ile Lys Val Gln Phe Ala Lys Asn Phe Val Tyr Asp Asn
    205                 210                 215 aat tca att ctg cga gtt cct gaa tcg ttt cac gat cca aac aga ttc       725
Asn Ser Ile Leu Arg Val Pro Glu Ser Phe His Asp Pro Asn Arg Phe
220                 225                 230                 235 gaa caa tca tta gaa gta gca cca aga atc gaa gca tgg ttt gga att       773
Glu Gln Ser Leu Glu Val Ala Pro Arg Ile Glu Ala Trp Phe Gly Ile
                240                 245                 250 tac att gga atc aaa gaa ttg ttc gat ggt gaa cct gtg ctc aat ttt       821
Tyr Ile Gly Ile Lys Glu Leu Phe Asp Gly Glu Pro Val Leu Asn Phe
            255                 260                 265 gca att gtc gat aaa cta ttc tac aat gca ccg aaa atg tct ctt ctg       869
Ala Ile Val Asp Lys Leu Phe Tyr Asn Ala Pro Lys Met Ser Leu Leu
        270                 275                 280 gat tat ctt ctc cta att gtc gac ccc cag tcg tgt aac gat gat gta       917
Asp Tyr Leu Leu Leu Ile Val Asp Pro Gln Ser Cys Asn Asp Asp Val
    285                 290                 295 cga aaa gat ctt aaa aca aaa ctg atg gcg gga aaa atg aca atc aga       965
Arg Lys Asp Leu Lys Thr Lys Leu Met Ala Gly Lys Met Thr Ile Arg
300                 305                 310                 315 caa gcc gcg cgg cca aga att cga caa tta ttg gaa aat ttg aag ctg      1013
Gln Ala Ala Arg Pro Arg Ile Arg Gln Leu Leu Glu Asn Leu Lys Leu
                320                 325                 330 aaa tgc gca gaa gtt tgg gat aac gaa atg tcg aga ttg aca gaa cga      1061
Lys Cys Ala Glu Val Trp Asp Asn Glu Met Ser Arg Leu Thr Glu Arg
            335                 340                 345 cat ctg aca ttt cta gat ttg tgc gag gaa aac tct ctt gtt tat aaa      1109
His Leu Thr Phe Leu Asp Leu Cys Glu Glu Asn Ser Leu Val Tyr Lys
        350                 355                 360 gtc act ggt aaa tcg gac aga gga aga aat gca aaa aag tac gat act      1157
Val Thr Gly Lys Ser Asp Arg Gly Arg Asn Ala Lys Lys Tyr Asp Thr
    365                 370                 375 aca ttg ttc aaa atc tat gag gaa aac aaa aag ttc att gag ttt ccc      1205
```

```
                                      -continued

Thr Leu Phe Lys Ile Tyr Glu Glu Asn Lys Lys Phe Ile Glu Phe Pro
380             385             390             395 cac cta cca cta gtc aaa gtt aaa agt gga gca aaa gaa tac gct gta     1253
His Leu Pro Leu Val Lys Val Lys Ser Gly Ala Lys Glu Tyr Ala Val
                400             405             410 cca atg gaa cat ctt gaa gtt cat gag aag cca caa aga tac aag aat     1301
Pro Met Glu His Leu Glu Val His Glu Lys Pro Gln Arg Tyr Lys Asn
            415             420             425 cga att gat ctg gtg atg caa gac aag ttt cta aag cga gct aca cga     1349
Arg Ile Asp Leu Val Met Gln Asp Lys Phe Leu Lys Arg Ala Thr Arg
        430             435             440 aaa cct cac gac tac aaa gaa aat acc cta aaa atg ctg aaa gaa ttg     1397
Lys Pro His Asp Tyr Lys Glu Asn Thr Leu Lys Met Leu Lys Glu Leu
    445             450             455 gat ttc tct tct gaa gag cta aat ttt gtt gaa aga ttt gga tta tgc     1445
Asp Phe Ser Ser Glu Glu Leu Asn Phe Val Glu Arg Phe Gly Leu Cys
460             465             470             475 tcc aaa ctt cag atg atc gaa tgt cca gga aag gtt ttg aaa gag cca     1493
Ser Lys Leu Gln Met Ile Glu Cys Pro Gly Lys Val Leu Lys Glu Pro
                480             485             490 atg ctt gtg aat agt gta aat gaa caa att aaa atg aca cca gtg att     1541
Met Leu Val Asn Ser Val Asn Glu Gln Ile Lys Met Thr Pro Val Ile
            495             500             505 cgt gga ttt caa gaa aaa caa ttg aat gtg gtt ccc gaa aaa gaa ctt     1589
Arg Gly Phe Gln Glu Lys Gln Leu Asn Val Val Pro Glu Lys Glu Leu
        510             515             520 tgc tgt gct gtt ttt gta gtc aac gaa aca gcg gga aat cca tgc tta     1637
Cys Cys Ala Val Phe Val Val Asn Glu Thr Ala Gly Asn Pro Cys Leu
    525             530             535 gaa gag aac gac gtt gtt aag ttc tac acc gaa cta att ggt ggt tgc     1685
Glu Glu Asn Asp Val Val Lys Phe Tyr Thr Glu Leu Ile Gly Gly Cys
540             545             550             555 aag ttc cgt gga ata cga att ggt gcc aat gaa aac aga gga gcg caa     1733
Lys Phe Arg Gly Ile Arg Ile Gly Ala Asn Glu Asn Arg Gly Ala Gln
                560             565             570 tct att atg tac gac gcg acg aaa aat gaa tat gcc ttc tac aaa aat     1781
Ser Ile Met Tyr Asp Ala Thr Lys Asn Glu Tyr Ala Phe Tyr Lys Asn
            575             580             585 tgt aca cta aat acc gga atc ggt aga ttt gaa ata gcc gca aca gaa     1829
Cys Thr Leu Asn Thr Gly Ile Gly Arg Phe Glu Ile Ala Ala Thr Glu
        590             595             600 gcg aag aat atg ttt gaa cgt ctt ccc gat aaa gaa caa aaa gtc tta     1877
Ala Lys Asn Met Phe Glu Arg Leu Pro Asp Lys Glu Gln Lys Val Leu
    605             610             615 atg ttc att atc att tcc aaa cga caa ctg aat gct tac ggt ttt gtg     1925
Met Phe Ile Ile Ile Ser Lys Arg Gln Leu Asn Ala Tyr Gly Phe Val
620             625             630             635 aaa cat tat tgc gat cac acc atc ggt gta gct aat cag cat att act     1973
Lys His Tyr Cys Asp His Thr Ile Gly Val Ala Asn Gln His Ile Thr
                640             645             650 tct gaa aca gtc aca aaa gct ttg gca tca cta agg cac gag aaa gga     2021
Ser Glu Thr Val Thr Lys Ala Leu Ala Ser Leu Arg His Glu Lys Gly
            655             660             665 tca aaa cga att ttc tat caa att gca ttg aaa atc aac gcg aaa tta     2069
Ser Lys Arg Ile Phe Tyr Gln Ile Ala Leu Lys Ile Asn Ala Lys Leu
        670             675             680 gga ggt att aac cag gag ctt gac tgg tca gaa att gca gaa ata tca     2117
Gly Gly Ile Asn Gln Glu Leu Asp Trp Ser Glu Ile Ala Glu Ile Ser
    685             690             695
```

```
                                                          -continued cca gaa gaa aaa gaa aga cgg aaa aca atg cca tta act atg tat gtt     2165
Pro Glu Glu Lys Glu Arg Arg Lys Thr Met Pro Leu Thr Met Tyr Val
700             705                 710                 715 gga att gat gta act cat cca acc tcc tac agt gga att gat tat tct     2213
Gly Ile Asp Val Thr His Pro Thr Ser Tyr Ser Gly Ile Asp Tyr Ser
                720                 725                 730 ata gcg gct gta gta gcg agt atc aat cca ggt gga act atc tat cga     2261
Ile Ala Ala Val Val Ala Ser Ile Asn Pro Gly Gly Thr Ile Tyr Arg
            735                 740                 745 aat atg att gtg act caa gaa gaa tgt cgt ccc ggt gag cgt gca gtg     2309
Asn Met Ile Val Thr Gln Glu Glu Cys Arg Pro Gly Glu Arg Ala Val
        750                 755                 760 gct cat gga cgg gaa aga aca gat att ttg gaa gca aag ttc gtg aaa     2357
Ala His Gly Arg Glu Arg Thr Asp Ile Leu Glu Ala Lys Phe Val Lys
765                 770                 775 ttg ctc aga gaa ttc gca gaa aac aac gac aat cga gca cca gcg cat     2405
Leu Leu Arg Glu Phe Ala Glu Asn Asn Asp Asn Arg Ala Pro Ala His
780             785                 790                 795 att gta gtc tat cga gac gga gtt agc gat tcg gag atg cta cgt gtt     2453
Ile Val Val Tyr Arg Asp Gly Val Ser Asp Ser Glu Met Leu Arg Val
                800                 805                 810 agt cat gat gag ctt cga tct tta aaa agc gaa gta aaa caa ttc atg     2501
Ser His Asp Glu Leu Arg Ser Leu Lys Ser Glu Val Lys Gln Phe Met
            815                 820                 825 tcg gaa cgg gat gga gaa gat cca gag ccg aag tac acg ttc att gtg     2549
Ser Glu Arg Asp Gly Glu Asp Pro Glu Pro Lys Tyr Thr Phe Ile Val
        830                 835                 840 att cag aaa aga cac aat aca cga ttg ctt cga aga atg gaa aaa gat     2597
Ile Gln Lys Arg His Asn Thr Arg Leu Leu Arg Arg Met Glu Lys Asp
845                 850                 855 aag cca gtg gtc aat aaa gat ctt act cct gct gaa aca gat gtc gct     2645
Lys Pro Val Val Asn Lys Asp Leu Thr Pro Ala Glu Thr Asp Val Ala
860             865                 870                 875 gtt gct gct gtt aaa caa tgg gag gag gat atg aaa gaa agc aaa gaa     2693
Val Ala Ala Val Lys Gln Trp Glu Glu Asp Met Lys Glu Ser Lys Glu
                880                 885                 890 act gga att gtg aac cca tca tcc gga aca act gtg gat aaa ctt atc     2741
Thr Gly Ile Val Asn Pro Ser Ser Gly Thr Thr Val Asp Lys Leu Ile
            895                 900                 905 gtt tcg aaa tac aaa ttc gat ttt ttc ttg gca tct cat cat ggt gtc     2789
Val Ser Lys Tyr Lys Phe Asp Phe Phe Leu Ala Ser His His Gly Val
        910                 915                 920 ctt ggt aca tct cgt cca gga cat tac act gtt atg tat gac gat aaa     2837
Leu Gly Thr Ser Arg Pro Gly His Tyr Thr Val Met Tyr Asp Asp Lys
925                 930                 935 gga atg agc caa gat gaa gtc tat aaa atg acc tac gga ctt gct ttt     2885
Gly Met Ser Gln Asp Glu Val Tyr Lys Met Thr Tyr Gly Leu Ala Phe
940             945                 950                 955 ctc tct gct aga tgt cga aaa ccc atc tcg ttg cct gtt ccg gtt cat     2933
Leu Ser Ala Arg Cys Arg Lys Pro Ile Ser Leu Pro Val Pro Val His
                960                 965                 970 tat gct cat tta tca tgt gaa aaa gcg aaa gag ctt tat cga act tac     2981
Tyr Ala His Leu Ser Cys Glu Lys Ala Lys Glu Leu Tyr Arg Thr Tyr
            975                 980                 985 aag gaa cat tac atc ggt gac tat gca cag cca cgg act cga cac gaa     3029
Lys Glu His Tyr Ile Gly Asp Tyr Ala Gln Pro Arg Thr Arg His Glu
        990                 995                 1000 atg gaa cat ttt ctc caa act aac gtg aag tac cct gga atg tcg ttc     3077
Met Glu His Phe Leu Gln Thr Asn Val Lys Tyr Pro Gly Met Ser Phe
1005                1010                1015
```

-continued

```
gca taacattttg caaaagtgtc gcccgtttca atcaaatttt tcaattgtag        3130
Ala
1020 atattgtact tactttttt taaagcccgg tttcaaaaat tcattccatg actaacgttt  3190 tcataaatta cttgaaattt aaaaaaaaaa aaaaaaa                          3227
```

<210> SEQ ID NO 3
<211> LENGTH: 1020
<212> TYPE: PRT
<213> ORGANISM: Caenorhabditis elegans

<400> SEQUENCE: 3

```
Met Ser Ser Asn Phe Pro Glu Leu Glu Lys Gly Phe Tyr Arg His Ser
 1               5                  10                  15

Leu Asp Pro Glu Met Lys Trp Leu Ala Arg Pro Thr Gly Lys Cys Asp
            20                  25                  30

Gly Lys Phe Tyr Glu Lys Lys Val Leu Leu Val Asn Trp Phe Lys
        35                  40                  45

Phe Ser Ser Lys Ile Tyr Asp Arg Glu Tyr Tyr Glu Tyr Glu Val Lys
    50                  55                  60

Met Thr Lys Glu Val Leu Asn Arg Lys Pro Gly Lys Pro Phe Pro Lys
65                  70                  75                  80

Lys Thr Glu Ile Pro Ile Pro Asp Arg Ala Lys Leu Phe Trp Gln His
                85                  90                  95

Leu Arg His Glu Lys Lys Gln Thr Asp Phe Ile Leu Glu Asp Tyr Val
            100                 105                 110

Phe Asp Glu Lys Asp Thr Val Tyr Ser Val Cys Arg Leu Asn Thr Val
        115                 120                 125

Thr Ser Lys Met Leu Val Ser Glu Lys Val Val Lys Lys Asp Ser Glu
130                 135                 140

Lys Lys Asp Glu Lys Asp Leu Glu Lys Lys Ile Leu Tyr Thr Met Ile
145                 150                 155                 160

Leu Thr Tyr Arg Lys Lys Phe His Leu Asn Phe Ser Arg Glu Asn Pro
                165                 170                 175

Glu Lys Asp Glu Glu Ala Asn Arg Ser Tyr Lys Phe Leu Lys Asn Val
            180                 185                 190

Met Thr Gln Lys Val Arg Tyr Ala Pro Phe Val Asn Glu Glu Ile Lys
        195                 200                 205

Val Gln Phe Ala Lys Asn Phe Val Tyr Asp Asn Asn Ser Ile Leu Arg
    210                 215                 220

Val Pro Glu Ser Phe His Asp Pro Asn Arg Phe Glu Gln Ser Leu Glu
225                 230                 235                 240

Val Ala Pro Arg Ile Glu Ala Trp Phe Gly Ile Tyr Ile Gly Ile Lys
                245                 250                 255

Glu Leu Phe Asp Gly Glu Pro Val Leu Asn Phe Ala Ile Val Asp Lys
            260                 265                 270

Leu Phe Tyr Asn Ala Pro Lys Met Ser Leu Leu Asp Tyr Leu Leu Leu
        275                 280                 285

Ile Val Asp Pro Gln Ser Cys Asn Asp Asp Val Arg Lys Asp Leu Lys
    290                 295                 300

Thr Lys Leu Met Ala Gly Lys Met Thr Ile Arg Gln Ala Ala Arg Pro
305                 310                 315                 320

Arg Ile Arg Gln Leu Leu Glu Asn Leu Lys Leu Lys Cys Ala Glu Val
                325                 330                 335
```

```
Trp Asp Asn Glu Met Ser Arg Leu Thr Glu Arg His Leu Thr Phe Leu
        340                 345                 350

Asp Leu Cys Glu Glu Asn Ser Leu Val Tyr Lys Val Thr Gly Lys Ser
        355                 360                 365

Asp Arg Gly Arg Asn Ala Lys Lys Tyr Asp Thr Thr Leu Phe Lys Ile
        370                 375                 380

Tyr Glu Glu Asn Lys Lys Phe Ile Glu Phe Pro His Leu Pro Leu Val
385                 390                 395                 400

Lys Val Lys Ser Gly Ala Lys Glu Tyr Ala Val Pro Met Glu His Leu
                405                 410                 415

Glu Val His Glu Lys Pro Gln Arg Tyr Lys Asn Arg Ile Asp Leu Val
        420                 425                 430

Met Gln Asp Lys Phe Leu Lys Arg Ala Thr Arg Lys Pro His Asp Tyr
        435                 440                 445

Lys Glu Asn Thr Leu Lys Met Leu Lys Glu Leu Asp Phe Ser Ser Glu
450                 455                 460

Glu Leu Asn Phe Val Glu Arg Phe Gly Leu Cys Ser Lys Leu Gln Met
465                 470                 475                 480

Ile Glu Cys Pro Gly Lys Val Leu Lys Glu Pro Met Leu Val Asn Ser
                485                 490                 495

Val Asn Glu Gln Ile Lys Met Thr Pro Val Ile Arg Gly Phe Gln Glu
                500                 505                 510

Lys Gln Leu Asn Val Val Pro Glu Lys Glu Leu Cys Cys Ala Val Phe
        515                 520                 525

Val Val Asn Glu Thr Ala Gly Asn Pro Cys Leu Glu Glu Asn Asp Val
        530                 535                 540

Val Lys Phe Tyr Thr Glu Leu Ile Gly Gly Cys Lys Phe Arg Gly Ile
545                 550                 555                 560

Arg Ile Gly Ala Asn Glu Asn Arg Gly Ala Gln Ser Ile Met Tyr Asp
                565                 570                 575

Ala Thr Lys Asn Glu Tyr Ala Phe Tyr Lys Asn Cys Thr Leu Asn Thr
                580                 585                 590

Gly Ile Gly Arg Phe Glu Ile Ala Ala Thr Glu Ala Lys Asn Met Phe
                595                 600                 605

Glu Arg Leu Pro Asp Lys Glu Gln Lys Val Leu Met Phe Ile Ile Ile
        610                 615                 620

Ser Lys Arg Gln Leu Asn Ala Tyr Gly Phe Val Lys His Tyr Cys Asp
625                 630                 635                 640

His Thr Ile Gly Val Ala Asn Gln His Ile Thr Ser Glu Thr Val Thr
                645                 650                 655

Lys Ala Leu Ala Ser Leu Arg His Glu Lys Gly Ser Lys Arg Ile Phe
                660                 665                 670

Tyr Gln Ile Ala Leu Lys Ile Asn Ala Lys Leu Gly Gly Ile Asn Gln
                675                 680                 685

Glu Leu Asp Trp Ser Glu Ile Ala Glu Ile Ser Pro Glu Glu Lys Glu
        690                 695                 700

Arg Arg Lys Thr Met Pro Leu Thr Met Tyr Val Gly Ile Asp Val Thr
705                 710                 715                 720

His Pro Thr Ser Tyr Ser Gly Ile Asp Tyr Ser Ile Ala Ala Val Val
                725                 730                 735

Ala Ser Ile Asn Pro Gly Gly Thr Ile Tyr Arg Asn Met Ile Val Thr
                740                 745                 750
```

```
Gln Glu Glu Cys Arg Pro Gly Glu Arg Ala Val Ala His Gly Arg Glu
            755                 760                 765

Arg Thr Asp Ile Leu Glu Ala Lys Phe Val Lys Leu Leu Arg Glu Phe
        770                 775                 780

Ala Glu Asn Asn Asp Asn Arg Ala Pro Ala His Ile Val Val Tyr Arg
785                 790                 795                 800

Asp Gly Val Ser Asp Ser Glu Met Leu Arg Val Ser His Asp Glu Leu
                805                 810                 815

Arg Ser Leu Lys Ser Glu Val Lys Gln Phe Met Ser Glu Arg Asp Gly
            820                 825                 830

Glu Asp Pro Glu Pro Lys Tyr Thr Phe Ile Val Ile Gln Lys Arg His
        835                 840                 845

Asn Thr Arg Leu Leu Arg Arg Met Glu Lys Asp Lys Pro Val Val Asn
850                 855                 860

Lys Asp Leu Thr Pro Ala Glu Thr Asp Val Ala Val Ala Ala Val Lys
865                 870                 875                 880

Gln Trp Glu Glu Asp Met Lys Glu Ser Lys Glu Thr Gly Ile Val Asn
                885                 890                 895

Pro Ser Ser Gly Thr Thr Val Asp Lys Leu Ile Val Ser Lys Tyr Lys
            900                 905                 910

Phe Asp Phe Phe Leu Ala Ser His His Gly Val Leu Gly Thr Ser Arg
        915                 920                 925

Pro Gly His Tyr Thr Val Met Tyr Asp Asp Lys Gly Met Ser Gln Asp
        930                 935                 940

Glu Val Tyr Lys Met Thr Tyr Gly Leu Ala Phe Leu Ser Ala Arg Cys
945                 950                 955                 960

Arg Lys Pro Ile Ser Leu Pro Val Pro Val His Tyr Ala His Leu Ser
                965                 970                 975

Cys Glu Lys Ala Lys Glu Leu Tyr Arg Thr Tyr Lys Glu His Tyr Ile
            980                 985                 990

Gly Asp Tyr Ala Gln Pro Arg Thr Arg His Glu Met Glu His Phe Leu
        995                 1000                1005

Gln Thr Asn Val Lys Tyr Pro Gly Met Ser Phe Ala
        1010                1015                1020

<210> SEQ ID NO 4
<211> LENGTH: 1222
<212> TYPE: DNA
<213> ORGANISM: Caenorhabditis elegans

<400> SEQUENCE: 4
atggatttaa ccaaactaac gtttgaaagc gttttcggtg gatcagatgt tcctatgaag      60
ccttcccgat cggaggataa caaaacgcca agaaacagaa cagatttgga gatgtttctg     120
aagaaaactc ccctcatggt actagaagag gctgctaagg ctgtctatca aaagacgcca     180
acttggggca ctgtcgaact tcctgaaggc ttcgagatga cgttgattct gaatgaaatt     240
actgtaaaag gccaggcaac aagcaagaaa gctgcgagac aaaaggctgc tgttgaatat     300
ttacgcaagg ttgtggagaa aggaaagcac gaaatctttt tcattcctgg aacaaccaaa     360
gaagaagctc tttcgaatat tgatcaaata tcggataagg ctgaggaatt gaaacgatca     420
acttcagatg ctgttcagga taacgataac gatgattcga ttcctacaag tgctgaattt     480
ccacctggta tttcgccaac cgagaattgg gtcggaaagt tgcaggaaaa atctcaaaaa     540
agcaagctgc aagccccaat ctatgaagat tccaagaatg agagaaccga gcgtttcttg     600
```

-continued

```
gttatatgca cgatgtgcaa tcaaaaaacc agaggaatca gaagtaagaa gaaggacgca      660
aagaatcttg cagcatggtt gatgtggaaa gcgttggaag acggtatcga atctctggaa      720
tcatatgata tggttgatgt gattgaaaat ttggaagaag ctgaacattt actcgaaatt      780
caggatcaag catccaagat taaagacaag cattccgcac tgattgatat actctcggac      840
aagaaaagat tttcagacta cagcatggat ttcaacgtat tatcagtgag cacaatggga      900
atacatcagg tgctattgga aatctcgttc cggcgtctag tttctccaga ccccgacgat      960
ttggaaatgg gagcagaaca cacccagact gaagaaatta tgaaggctac tgccgagaag     1020
gaaaagctac ggaagaagaa tatgccagat tccgggccgc tagtgtttgc tggacatggt     1080
tcatcggcgg aagaggctaa acagtgtgct tgtaaatcgg cgattatcca tttcaacacc     1140
tatgatttca cggattgaaa atattattgc gtattcctga aaaatgaagc gtctgaatga     1200
ttataaaaaa aaaaaaaaaa aa                                              1222
```

<210> SEQ ID NO 5
<211> LENGTH: 407
<212> TYPE: PRT
<213> ORGANISM: Caenorhabditis elegans
<220> FEATURE:
<221> NAME/KEY: VARIANT
<222> LOCATION: (1)...(407)
<223> OTHER INFORMATION: Xaa = Any Amino Acid

<400> SEQUENCE: 5

```
Met Asp Leu Thr Lys Leu Thr Phe Glu Ser Val Phe Gly Gly Ser Asp
 1               5                  10                  15

Val Pro Met Lys Pro Ser Arg Ser Glu Asp Asn Lys Thr Pro Arg Asn
            20                  25                  30

Arg Thr Asp Leu Glu Met Phe Leu Lys Lys Thr Pro Leu Met Val Leu
        35                  40                  45

Glu Glu Ala Ala Lys Ala Val Tyr Gln Lys Thr Pro Thr Trp Gly Thr
    50                  55                  60

Val Glu Leu Pro Glu Gly Phe Glu Met Thr Leu Ile Leu Asn Glu Ile
65                  70                  75                  80

Thr Val Lys Gly Gln Ala Thr Ser Lys Ala Ala Arg Gln Lys Ala
                85                  90                  95

Ala Val Glu Tyr Leu Arg Lys Val Val Glu Lys Gly Lys His Glu Ile
            100                 105                 110

Phe Phe Ile Pro Gly Thr Thr Lys Glu Glu Ala Leu Ser Asn Ile Asp
        115                 120                 125

Gln Ile Ser Asp Lys Ala Glu Glu Leu Lys Arg Ser Thr Ser Asp Ala
    130                 135                 140

Val Gln Asp Asn Asp Asn Asp Ser Ile Pro Thr Ser Ala Glu Phe
145                 150                 155                 160

Pro Pro Gly Ile Ser Pro Thr Glu Asn Trp Val Gly Lys Leu Gln Glu
                165                 170                 175

Lys Ser Gln Lys Ser Lys Leu Gln Ala Pro Ile Tyr Glu Asp Ser Lys
            180                 185                 190

Asn Glu Arg Thr Glu Arg Phe Leu Val Ile Cys Thr Met Cys Asn Gln
        195                 200                 205

Lys Thr Arg Gly Ile Arg Ser Lys Lys Lys Asp Ala Lys Asn Leu Ala
    210                 215                 220

Ala Trp Leu Met Trp Lys Ala Leu Glu Asp Gly Ile Glu Ser Leu Glu
225                 230                 235                 240
```

-continued

```
Ser Tyr Asp Met Val Asp Val Ile Glu Asn Leu Glu Ala Glu His
            245                 250                 255

Leu Leu Glu Ile Gln Asp Gln Ala Ser Lys Ile Lys Asp Lys His Ser
        260                 265                 270

Ala Leu Ile Asp Ile Leu Ser Asp Lys Lys Arg Phe Ser Asp Tyr Ser
            275                 280                 285

Met Asp Phe Asn Val Leu Ser Val Ser Thr Met Gly Ile His Gln Val
290                 295                 300

Leu Leu Glu Ile Ser Phe Arg Arg Leu Val Ser Pro Asp Pro Asp Asp
305                 310                 315                 320

Leu Glu Met Gly Ala Glu His Thr Gln Thr Glu Glu Ile Met Lys Ala
                325                 330                 335

Thr Ala Glu Lys Glu Lys Leu Arg Lys Lys Asn Met Pro Asp Ser Gly
            340                 345                 350

Pro Leu Val Phe Ala Gly His Gly Ser Ser Ala Glu Glu Ala Lys Gln
        355                 360                 365

Cys Ala Cys Lys Ser Ala Ile Ile His Phe Asn Thr Tyr Asp Phe Thr
370                 375                 380

Asp Xaa Lys Tyr Tyr Cys Val Phe Leu Lys Asn Glu Ala Ser Glu Xaa
385                 390                 395                 400

Leu Xaa Lys Lys Lys Lys Lys
            405
```

<210> SEQ ID NO 6
<211> LENGTH: 763
<212> TYPE: PRT
<213> ORGANISM: Arabidopsis thaliana

<400> SEQUENCE: 6

```
Gly Ile Ile Asn Gly Pro Lys Arg Glu Arg Ser Tyr Lys Val Ala Ile
1               5                   10                  15

Lys Phe Val Ala Arg Ala Asn Met His His Leu Gly Glu Phe Leu Ala
            20                  25                  30

Gly Lys Arg Ala Asp Cys Pro Gln Glu Ala Val Gln Ile Leu Asp Ile
        35                  40                  45

Val Leu Arg Glu Leu Ser Val Lys Arg Phe Cys Pro Val Gly Arg Ser
    50                  55                  60

Phe Phe Ser Pro Asp Ile Lys Thr Pro Gln Arg Leu Gly Glu Gly Leu
65                  70                  75                  80

Glu Ser Trp Cys Gly Phe Tyr Gln Ser Ile Arg Pro Thr Gln Met Gly
                85                  90                  95

Leu Ser Leu Asn Ile Asp Met Ala Ser Ala Phe Ile Glu Pro Leu
            100                 105                 110

Pro Val Ile Glu Phe Val Ala Gln Leu Leu Gly Lys Asp Val Leu Ser
        115                 120                 125

Lys Pro Leu Ser Asp Ser Asp Arg Val Lys Ile Lys Lys Gly Leu Arg
    130                 135                 140

Gly Val Lys Val Glu Val Thr His Arg Ala Asn Val Arg Arg Lys Tyr
145                 150                 155                 160

Arg Val Ala Gly Leu Thr Thr Gln Pro Thr Arg Glu Leu Met Phe Pro
                165                 170                 175

Val Asp Glu Asn Cys Thr Met Lys Ser Val Ile Glu Tyr Phe Gln Glu
            180                 185                 190

Met Tyr Gly Phe Thr Ile Gln His Thr His Leu Pro Cys Leu Gln Val
        195                 200                 205
```

-continued

```
Gly Asn Gln Lys Lys Ala Ser Tyr Leu Pro Met Glu Ala Cys Lys Ile
            210                 215                 220

Val Glu Gly Gln Arg Tyr Thr Lys Arg Leu Asn Glu Lys Gln Ile Thr
225                 230                 235                 240

Ala Leu Leu Lys Val Thr Cys Gln Arg Ala Glu Gly Gln Arg Asn Asp
                245                 250                 255

Ile Leu Arg Thr Val Gln His Asn Ala Tyr Asp Gln Asp Pro Tyr Ala
            260                 265                 270

Lys Glu Phe Gly Met Asn Ile Ser Glu Lys Leu Ala Ser Val Glu Ala
        275                 280                 285

Arg Ile Leu Pro Ala Pro Trp Leu Lys Tyr His Glu Asn Gly Lys Glu
    290                 295                 300

Lys Asp Cys Leu Pro Gln Val Gly Gln Trp Asn Met Met Asn Lys Lys
305                 310                 315                 320

Met Ile Asn Gly Met Thr Val Ser Arg Trp Ala Cys Val Asn Phe Ser
                325                 330                 335

Arg Ser Val Gln Glu Asn Val Ala Arg Gly Phe Cys Asn Glu Leu Gly
            340                 345                 350

Gln Met Cys Glu Val Ser Gly Met Glu Phe Asn Pro Glu Pro Val Ile
        355                 360                 365

Pro Ile Tyr Ser Ala Arg Pro Asp Gln Val Glu Lys Ala Leu Lys His
    370                 375                 380

Val Tyr His Thr Ser Met Asn Lys Thr Lys Gly Lys Glu Leu Glu Leu
385                 390                 395                 400

Leu Leu Ala Ile Leu Pro Asp Asn Asn Gly Ser Leu Tyr Gly Asp Leu
                405                 410                 415

Lys Arg Ile Cys Glu Thr Glu Leu Gly Leu Ile Ser Gln Cys Cys Leu
            420                 425                 430

Thr Lys His Val Phe Lys Ile Ser Lys Gln Tyr Leu Ala Asp Val Ser
        435                 440                 445

Leu Lys Ile Asn Val Lys Met Gly Gly Arg Asn Thr Val Leu Val Asp
    450                 455                 460

Ala Ile Ser Cys Arg Ile Pro Leu Val Ser Asp Ile Pro Thr Ile Ile
465                 470                 475                 480

Phe Gly Ala Asp Val Thr His Pro Glu Asn Gly Glu Glu Ser Ser Pro
                485                 490                 495

Ser Ile Ala Ala Val Val Ala Ser Gln Asp Trp Pro Glu Val Thr Lys
            500                 505                 510

Tyr Ala Gly Leu Val Cys Ala Gln Ala His Arg Gln Glu Leu Ile Gln
        515                 520                 525

Asp Leu Tyr Lys Thr Trp Gln Asp Pro Val Arg Gly Thr Val Ser Gly
    530                 535                 540

Gly Met Ile Arg Asp Leu Leu Ile Ser Phe Arg Lys Ala Thr Gly Gln
545                 550                 555                 560

Lys Pro Leu Arg Ile Ile Phe Tyr Arg Asp Gly Val Ser Glu Gly Gln
                565                 570                 575

Phe Tyr Gln Val Leu Leu Tyr Glu Leu Asp Ala Ile Arg Lys Ala Cys
            580                 585                 590

Ala Ser Leu Glu Pro Asn Tyr Gln Pro Pro Val Thr Phe Ile Val Val
        595                 600                 605

Gln Lys Arg His His Thr Arg Leu Phe Ala Asn Asn His Arg Asp Lys
    610                 615                 620
```

```
Asn Ser Thr Asp Arg Ser Gly Asn Ile Leu Pro Gly Thr Val Val Asp
625                 630                 635                 640

Thr Lys Ile Cys His Pro Thr Glu Phe Asp Phe Tyr Leu Cys Ser His
            645                 650                 655

Ala Gly Ile Gln Gly Thr Ser Arg Pro Ala His Tyr His Val Leu Trp
            660                 665                 670

Asp Glu Asn Asn Phe Thr Ala Asp Gly Ile Gln Ser Leu Thr Asn Asn
            675                 680                 685

Leu Cys Tyr Thr Tyr Ala Arg Cys Thr Arg Ser Val Ser Ile Val Pro
            690                 695                 700

Pro Ala Tyr Tyr Ala His Leu Ala Ala Phe Arg Ala Arg Phe Tyr Leu
705                 710                 715                 720

Glu Pro Glu Ile Met Gln Asp Asn Gly Ser Pro Gly Lys Lys Asn Thr
            725                 730                 735

Lys Thr Thr Thr Val Gly Asp Val Gly Val Lys Pro Leu Pro Ala Leu
            740                 745                 750

Lys Glu Asn Val Lys Arg Val Met Phe Tyr Cys
            755                 760

<210> SEQ ID NO 7
<211> LENGTH: 678
<212> TYPE: PRT
<213> ORGANISM: Drosophila melanogaster

<400> SEQUENCE: 7

Arg Ala Gly Glu Asn Ile Glu Ile Lys Ile Lys Ala Val Gly Ser Val
1               5                   10                  15

Gln Ser Thr Asp Ala Glu Gln Phe Gln Val Leu Asn Leu Ile Leu Arg
            20                  25                  30

Arg Ala Met Glu Gly Leu Asp Leu Lys Leu Val Ser Arg Tyr Tyr Tyr
        35                  40                  45

Asp Pro Gln Ala Lys Ile Asn Leu Glu Asn Phe Arg Met Gln Leu Trp
    50                  55                  60

Pro Gly Tyr Gln Thr Ser Ile Arg Gln His Glu Asn Asp Ile Leu Leu
65                  70                  75                  80

Cys Ser Glu Ile Cys His Lys Val Met Arg Thr Glu Thr Leu Tyr Asn
                85                  90                  95

Ile Leu Ser Asp Ala Ile Arg Asp Ser Asp Tyr Gln Ser Thr Phe
            100                 105                 110

Lys Arg Ala Val Met Gly Met Val Ile Leu Thr Asp Tyr Asn Asn Lys
        115                 120                 125

Thr Tyr Arg Ile Asp Asp Val Asp Phe Gln Ser Thr Pro Leu Cys Lys
    130                 135                 140

Phe Lys Thr Asn Asp Gly Glu Ile Ser Tyr Val Asp Tyr Tyr Lys Lys
145                 150                 155                 160

Arg Tyr Asn Ile Ile Ile Arg Asp Leu Lys Gln Pro Leu Val Met Ser
                165                 170                 175

Arg Pro Thr Asp Lys Asn Ile Arg Gly Gly Asn Asp Gln Ala Ile Met
            180                 185                 190

Ile Ile Pro Glu Leu Ala Arg Ala Thr Gly Met Thr Asp Ala Met Arg
        195                 200                 205

Ala Asp Phe Arg Thr Leu Arg Ala Met Ser Glu His Thr Arg Leu Asn
    210                 215                 220

Pro Asp Arg Arg Ile Glu Arg Leu Arg Met Phe Asn Lys Arg Leu Lys
225                 230                 235                 240
```

-continued

Ser Cys Lys Gln Ser Val Glu Thr Leu Lys Ser Trp Asn Ile Glu Leu
                245                 250                 255

Asp Ser Ala Leu Val Glu Ile Pro Ala Arg Val Leu Pro Pro Glu Lys
            260                 265                 270

Ile Leu Phe Gly Asn Gln Lys Ile Phe Val Cys Asp Ala Arg Ala Asp
        275                 280                 285

Trp Thr Asn Glu Phe Arg Thr Cys Ser Met Phe Lys Asn Val His Ile
    290                 295                 300

Asn Arg Trp Tyr Val Ile Thr Pro Ser Arg Asn Leu Arg Glu Thr Gln
305                 310                 315                 320

Glu Phe Val Gln Met Cys Ile Arg Thr Ala Ser Ser Met Lys Met Asn
                325                 330                 335

Ile Cys Asn Pro Ile Tyr Glu Glu Ile Pro Asp Asp Arg Asn Gly Thr
            340                 345                 350

Tyr Ser Gln Ala Ile Asp Asn Ala Ala Ala Asn Asp Pro Gln Ile Val
        355                 360                 365

Met Val Val Met Arg Ser Pro Asn Glu Glu Lys Tyr Ser Cys Ile Lys
    370                 375                 380

Lys Arg Thr Cys Val Asp Arg Pro Val Pro Ser Gln Val Val Thr Leu
385                 390                 395                 400

Lys Val Ile Ala Pro Arg Gln Gln Lys Pro Thr Gly Leu Met Ser Ile
                405                 410                 415

Ala Thr Lys Val Val Ile Gln Met Asn Ala Lys Leu Met Gly Ala Pro
            420                 425                 430

Trp Gln Val Val Ile Pro Leu His Gly Leu Met Thr Val Gly Phe Asp
        435                 440                 445

Val Cys His Ser Pro Lys Asn Lys Asn Lys Ser Tyr Gly Ala Phe Val
    450                 455                 460

Ala Thr Met Asp Gln Lys Glu Ser Phe Arg Tyr Phe Ser Thr Val Asn
465                 470                 475                 480

Glu His Ile Lys Gly Gln Glu Leu Ser Glu Gln Met Ser Val Asn Met
                485                 490                 495

Ala Cys Ala Leu Arg Ser Tyr Gln Glu Gln His Arg Ser Leu Pro Glu
            500                 505                 510

Arg Ile Leu Phe Phe Arg Asp Gly Val Gly Asp Gly Gln Leu Tyr Gln
        515                 520                 525

Val Val Asn Ser Glu Val Asn Thr Leu Lys Asp Arg Leu Asp Glu Ile
    530                 535                 540

Tyr Lys Ser Ala Gly Lys Gln Glu Gly Cys Arg Met Thr Phe Ile Ile
545                 550                 555                 560

Val Ser Lys Arg Ile Asn Ser Arg Tyr Phe Thr Gly His Arg Asn Pro
                565                 570                 575

Val Pro Gly Thr Val Val Asp Asp Val Ile Thr Leu Pro Glu Arg Tyr
            580                 585                 590

Asp Phe Phe Leu Val Ser Gln Ala Val Arg Ile Gly Thr Val Ser Pro
        595                 600                 605

Thr Ser Tyr Asn Val Ile Ser Asp Asn Met Gly Leu Asn Ala Asp Lys
    610                 615                 620

Leu Gln Met Leu Ser Tyr Lys Met Thr His Met Tyr Tyr Asn Tyr Ser
625                 630                 635                 640

Gly Thr Ile Arg Val Pro Ala Val Cys His Tyr Ala His Lys Leu Ala
                645                 650                 655

```
Phe Leu Val Ala Glu Ser Ile Asn Arg Ala Pro Ser Ala Gly Leu Gln
                660                 665                 670

Asn Gln Leu Tyr Phe Leu
        675

<210> SEQ ID NO 8
<211> LENGTH: 69
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION:
<222> 2, 3, 4, 6, 8, 9, 12, 13, 14, 15, 16, 17, 18, 19,
      21, 22, 23, 24, 26, 29, 31, 32, 33, 35, 36, 37, 39, 40, 41, 44,
      45, 46, 47, 49, 51, 55, 56, 59, 60, 63, 64, 67, 68
<223> OTHER INFORMATION: Xaa = Any Amino Acid
<220> FEATURE:
<221> NAME/KEY: VARIANT
<222> LOCATION: 10, 25, 43
<223> OTHER INFORMATION: Xaa = Any amino Acid if present

<400> SEQUENCE: 8

Pro Xaa Xaa Xaa Leu Xaa Glu Xaa Xaa Xaa Gln Xaa Xaa Xaa Xaa Xaa
  1               5                  10                  15

Xaa Xaa Xaa Tyr Xaa Xaa Xaa Xaa Xaa Gly Pro Xaa His Xaa Xaa
             20                  25                  30

Xaa Phe Xaa Xaa Xaa Val Xaa Xaa Xaa Gly Xaa Xaa Xaa Xaa Xaa Gly
         35                  40                  45

Xaa Gly Xaa Ser Lys Lys Xaa Xaa Ala Lys Xaa Xaa Ala Ala Xaa Xaa
     50                  55                  60

Ala Leu Xaa Xaa Leu
 65

<210> SEQ ID NO 9
<211> LENGTH: 766
<212> TYPE: PRT
<213> ORGANISM: Caenorhabditis elegans

<400> SEQUENCE: 9

Ser Ala Val Glu Arg Gln Phe Ser Val Ser Leu Lys Trp Val Gly Gln
  1               5                  10                  15

Val Ser Leu Ser Thr Leu Glu Asp Ala Met Glu Gly Arg Val Arg Gln
             20                  25                  30

Val Pro Phe Glu Ala Val Gln Ala Met Asp Val Ile Leu Arg His Leu
         35                  40                  45

Pro Ser Leu Lys Tyr Thr Pro Val Gly Arg Ser Phe Ser Pro Pro
     50                  55                  60

Val Pro Asn Ala Ser Gly Val Met Ala Gly Ser Cys Pro Pro Gln Ala
 65                  70                  75                  80

Ser Gly Ala Val Ala Gly Gly Ala His Ser Ala Gly Gln Tyr His Ala
                 85                  90                  95

Glu Ser Lys Leu Gly Gly Gly Arg Glu Val Trp Phe Gly Phe His Gln
                100                 105                 110

Ser Val Arg Pro Ser Gln Trp Lys Met Met Leu Asn Ile Asp Val Ser
            115                 120                 125

Ala Thr Ala Phe Tyr Arg Ser Met Pro Val Ile Glu Phe Ile Ala Glu
        130                 135                 140

Val Leu Glu Leu Pro Val Gln Ala Leu Ala Glu Arg Arg Ala Leu Ser
145                 150                 155                 160
```

```
Asp Ala Gln Arg Val Lys Phe Thr Lys Glu Ile Arg Gly Leu Lys Ile
                165                 170                 175
Glu Ile Thr His Cys Gly Gln Met Arg Arg Lys Tyr Arg Val Cys Asn
            180                 185                 190
Val Thr Arg Arg Pro Ala Gln Thr Gln Thr Phe Pro Leu Gln Leu Glu
        195                 200                 205
Thr Gly Gln Thr Ile Glu Cys Thr Val Ala Lys Tyr Phe Tyr Asp Lys
    210                 215                 220
Tyr Arg Ile Gln Leu Lys Tyr Pro His Leu Pro Cys Leu Gln Val Gly
225                 230                 235                 240
Gln Glu Gln Lys His Thr Tyr Leu Pro Pro Glu Val Cys Asn Ile Val
                245                 250                 255
Pro Gly Gln Arg Cys Ile Lys Lys Leu Thr Asp Val Gln Thr Ser Thr
            260                 265                 270
Met Ile Lys Ala Thr Ala Arg Ser Ala Pro Glu Arg Glu Arg Glu Ile
        275                 280                 285
Ser Asn Leu Val Arg Lys Ala Glu Phe Ser Ala Asp Pro Phe Ala His
    290                 295                 300
Glu Phe Gly Ile Thr Ile Asn Pro Ala Met Thr Glu Val Lys Gly Arg
305                 310                 315                 320
Val Leu Ser Ala Pro Lys Leu Leu Tyr Gly Gly Arg Thr Arg Ala Thr
                325                 330                 335
Ala Leu Pro Asn Gln Gly Val Trp Asp Met Arg Gly Lys Gln Phe His
            340                 345                 350
Thr Gly Ile Asp Val Arg Val Trp Ala Ile Ala Cys Phe Ala Gln Gln
        355                 360                 365
Gln His Val Lys Glu Asn Asp Leu Arg Met Phe Thr Asn Gln Leu Gln
    370                 375                 380
Arg Ile Ser Asn Asp Ala Gly Met Pro Ile Val Gly Asn Pro Cys Phe
385                 390                 395                 400
Cys Lys Tyr Ala Val Gly Val Glu Gln Val Glu Pro Met Phe Lys Tyr
                405                 410                 415
Leu Lys Gln Asn Tyr Ser Gly Ile Gln Leu Val Val Val Leu Pro
            420                 425                 430
Gly Lys Thr Pro Val Tyr Ala Glu Val Lys Arg Val Gly Asp Thr Val
        435                 440                 445
Leu Gly Ile Ala Thr Gln Cys Val Gln Ala Lys Asn Ala Ile Arg Thr
    450                 455                 460
Thr Pro Gln Thr Leu Ser Asn Leu Cys Leu Lys Met Asn Val Lys Leu
465                 470                 475                 480
Gly Gly Val Asn Ser Ile Leu Leu Pro Asn Val Arg Pro Arg Ile Phe
                485                 490                 495
Asn Glu Pro Val Ile Phe Phe Gly Cys Asp Ile Thr His Pro Pro Ala
            500                 505                 510
Gly Asp Ser Arg Lys Pro Ser Ile Ala Ala Val Val Gly Ser Met Asp
        515                 520                 525
Ala His Pro Ser Arg Tyr Ala Ala Thr Val Arg Val Gln Gln His Arg
    530                 535                 540
Gln Glu Ile Ile Ser Asp Leu Thr Tyr Met Val Arg Glu Leu Leu Val
545                 550                 555                 560
Gln Phe Tyr Arg Asn Thr Arg Phe Lys Pro Ala Arg Ile Val Val Tyr
                565                 570                 575
Arg Asp Gly Val Ser Glu Gly Gln Phe Phe Asn Val Leu Gln Tyr Glu
```

-continued

```
                580                 585                 590
Leu Arg Ala Ile Arg Glu Ala Cys Met Met Leu Glu Arg Gly Tyr Gln
            595                 600                 605

Pro Gly Ile Thr Phe Ile Ala Val Gln Lys Arg His His Thr Arg Leu
        610                 615                 620

Phe Ala Val Asp Lys Lys Asp Gln Val Gly Lys Ala Tyr Asn Ile Pro
625                 630                 635                 640

Pro Gly Thr Thr Val Asp Val Gly Ile Thr His Pro Thr Glu Phe Asp
                645                 650                 655

Phe Tyr Leu Cys Ser His Ala Gly Ile Gln Gly Thr Ser Arg Pro Ser
            660                 665                 670

His Tyr His Val Leu Trp Asp Asp Asn Asn Leu Thr Ala Asp Glu Leu
        675                 680                 685

Gln Gln Leu Thr Tyr Gln Met Cys His Thr Tyr Val Arg Cys Thr Arg
            690                 695                 700

Ser Val Ser Ile Pro Ala Pro Ala Tyr Tyr Ala His Leu Val Ala Phe
705                 710                 715                 720

Arg Ala Arg Tyr His Leu Val Asp Arg Glu His Asp Ser Gly Glu Gly
                725                 730                 735

Ser Gln Pro Ser Gly Thr Ser Glu Asp Thr Thr Leu Ser Asn Met Ala
            740                 745                 750

Arg Ala Val Gln Val Ile Leu Ala Phe Asn Leu Val Ser Ile
            755                 760                 765

<210> SEQ ID NO 10
<211> LENGTH: 737
<212> TYPE: PRT
<213> ORGANISM: Oryctolagus cuniculus

<400> SEQUENCE: 10

Gly Lys Asp Arg Ile Phe Lys Val Ser Ile Lys Trp Val Ser Cys Val
1               5                   10                  15

Ser Leu Gln Ala Leu His Asp Ala Leu Ser Gly Arg Leu Pro Ser Val
            20                  25                  30

Pro Phe Glu Thr Ile Gln Ala Leu Asp Val Val Met Arg His Leu Pro
        35                  40                  45

Ser Met Arg Tyr Thr Pro Val Gly Arg Ser Phe Thr Ala Ser Glu
    50                  55                  60

Gly Cys Ser Asn Pro Leu Gly Gly Gly Arg Glu Val Trp Phe Gly Phe
65                  70                  75                  80

His Gln Ser Val Arg Pro Ser Leu Trp Lys Met Met Leu Asn Ile Asp
            85                  90                  95

Val Ser Ala Thr Ala Phe Tyr Lys Ala Gln Pro Val Ile Glu Phe Val
            100                 105                 110

Cys Glu Val Leu Asp Phe Lys Ser Ile Glu Glu Gln Lys Pro Leu
            115                 120                 125

Thr Asp Ser Gln Arg Val Lys Phe Thr Lys Glu Ile Lys Gly Leu Lys
        130                 135                 140

Val Glu Ile Thr His Cys Gly Gln Met Lys Arg Lys Tyr Arg Val Cys
145                 150                 155                 160

Asn Val Thr Arg Arg Pro Ala Ser His Gln Thr Phe Pro Leu Gln Gln
                165                 170                 175

Glu Ser Gly Gln Thr Val Glu Cys Thr Val Ala Gln Tyr Phe Lys Asp
            180                 185                 190
```

-continued

```
Arg His Lys Leu Val Leu Arg Tyr Pro His Leu Pro Cys Leu Gln Val
        195                 200                 205

Gly Gln Glu Gln Lys His Thr Tyr Leu Pro Leu Glu Val Cys Asn Ile
        210                 215                 220

Val Ala Gly Gln Arg Cys Ile Lys Lys Leu Thr Asp Asn Gln Thr Ser
225                 230                 235                 240

Thr Met Ile Arg Ala Thr Ala Arg Ser Ala Pro Asp Arg Gln Glu Glu
                245                 250                 255

Ile Ser Lys Leu Met Arg Ser Ala Ser Phe Asn Thr Asp Pro Tyr Val
            260                 265                 270

Arg Glu Phe Gly Ile Met Val Lys Asp Glu Met Thr Asp Val Thr Gly
        275                 280                 285

Arg Val Leu Gln Pro Pro Ser Ile Leu Tyr Gly Gly Arg Asn Lys Ala
    290                 295                 300

Ile Ala Thr Pro Val Gln Gly Val Trp Asp Met Arg Asn Lys Gln Phe
305                 310                 315                 320

His Thr Gly Ile Glu Ile Lys Val Trp Ala Ile Ala Cys Phe Ala Pro
                325                 330                 335

Gln Arg Gln Cys Thr Glu Val His Leu Lys Ser Phe Thr Glu Gln Leu
            340                 345                 350

Arg Lys Ile Ser Arg Asp Ala Gly Met Pro Ile Gln Gly Gln Pro Cys
        355                 360                 365

Phe Cys Lys Tyr Ala Gln Gly Ala Asp Ser Val Gly Pro Met Phe Arg
    370                 375                 380

His Leu Lys Asn Thr Tyr Ala Gly Leu Gln Leu Val Val Ile Leu
385                 390                 395                 400

Pro Gly Lys Thr Pro Val Tyr Ala Glu Val Lys Arg Val Gly Asp Thr
                405                 410                 415

Val Leu Gly Met Ala Thr Gln Cys Val Gln Met Lys Asn Val Gln Arg
            420                 425                 430

Thr Thr Pro Gln Thr Leu Ser Asn Leu Cys Leu Lys Ile Asn Val Lys
        435                 440                 445

Leu Gly Gly Val Asn Asn Ile Leu Leu Pro Gln Gly Arg Pro Pro Val
    450                 455                 460

Phe Gln Gln Pro Val Ile Phe Leu Gly Ala Asp Val Thr His Pro Pro
465                 470                 475                 480

Ala Gly Asp Gly Lys Lys Pro Ser Ile Ala Ala Val Val Gly Ser Met
                485                 490                 495

Asp Ala His Pro Asn Arg Tyr Cys Ala Thr Val Arg Val Gln Gln His
            500                 505                 510

Arg Gln Glu Ile Ile Gln Asp Leu Ala Ala Met Val Arg Glu Leu Leu
        515                 520                 525

Ile Gln Phe Tyr Lys Ser Thr Arg Phe Lys Pro Thr Arg Ile Ile Phe
    530                 535                 540

Tyr Arg Asp Gly Val Ser Glu Gly Gln Phe Gln Gln Val Leu His His
545                 550                 555                 560

Glu Leu Leu Ala Ile Arg Glu Ala Cys Ile Lys Leu Glu Lys Asp Tyr
                565                 570                 575

Gln Pro Gly Ile Thr Phe Ile Val Val Gln Lys Arg His His Thr Arg
            580                 585                 590

Leu Phe Cys Thr Asp Lys Asn Glu Arg Val Gly Lys Ser Gly Asn Ile
        595                 600                 605

Pro Ala Gly Thr Thr Val Asp Thr Lys Ile Thr His Pro Thr Glu Phe
```

```
                610                 615                 620
Asp Phe Tyr Leu Cys Ser His Ala Gly Ile Gln Gly Thr Ser Arg Pro
625                 630                 635                 640

Ser His Tyr His Val Leu Trp Asp Asp Asn Arg Phe Ser Ser Asp Glu
                645                 650                 655

Leu Gln Ile Leu Thr Tyr Gln Leu Cys His Thr Tyr Val Arg Cys Thr
                660                 665                 670

Arg Ser Val Ser Ile Pro Ala Pro Ala Tyr Tyr Ala His Leu Val Ala
            675                 680                 685

Phe Arg Ala Arg Tyr His Leu Val Asp Lys Glu His Asp Ser Ala Glu
        690                 695                 700

Gly Ser His Thr Ser Gly Gln Ser Asn Gly Arg Asp His Gln Ala Leu
705                 710                 715                 720

Ala Lys Ala Val Gln Val His Gln Asp Thr Leu Arg Thr Met Tyr Phe
                725                 730                 735

Ala
```

<210> SEQ ID NO 11
<211> LENGTH: 66
<212> TYPE: PRT
<213> ORGANISM: Xenopus laevis

<400> SEQUENCE: 11

```
Pro Val Gly Ser Leu Gln Glu Leu Ala Val Gln Lys Gly Trp Arg Leu
1               5                   10                  15

Pro Glu Tyr Thr Val Ala Gln Glu Ser Gly Pro Pro His Lys Arg Glu
                20                  25                  30

Phe Thr Ile Thr Cys Arg Val Glu Thr Phe Val Glu Thr Gly Ser Gly
            35                  40                  45

Thr Ser Lys Gln Val Ala Lys Arg Val Ala Ala Glu Lys Leu Leu Thr
        50                  55                  60

Lys Phe
65
```

<210> SEQ ID NO 12
<211> LENGTH: 66
<212> TYPE: PRT
<213> ORGANISM: Homo sapiens

<400> SEQUENCE: 12

```
Phe Met Glu Glu Leu Asn Thr Tyr Arg Gln Lys Gln Gly Val Val Leu
1               5                   10                  15

Lys Tyr Gln Glu Leu Pro Asn Ser Gly Pro Pro His Asp Arg Arg Phe
                20                  25                  30

Thr Phe Gln Val Ile Ile Asp Gly Arg Glu Phe Pro Glu Gly Glu Gly
            35                  40                  45

Arg Ser Lys Lys Glu Ala Lys Asn Ala Ala Ala Lys Leu Ala Val Glu
        50                  55                  60

Ile Leu
65
```

<210> SEQ ID NO 13
<211> LENGTH: 818
<212> TYPE: PRT
<213> ORGANISM: Caenorhabditis elegans

<400> SEQUENCE: 13

-continued

```
Val Asn Glu Glu Ile Lys Val Gln Phe Ala Lys Asn Phe Val Tyr Asp
 1               5                  10                  15

Asn Asn Ser Ile Leu Arg Val Pro Glu Ser Phe His Asp Pro Asn Arg
             20                  25                  30

Phe Glu Gln Ser Leu Glu Val Ala Pro Arg Ile Glu Ala Trp Phe Gly
         35                  40                  45

Ile Tyr Ile Gly Ile Lys Glu Leu Phe Asp Gly Glu Pro Val Leu Asn
     50                  55                  60

Phe Ala Ile Val Asp Lys Leu Phe Tyr Asn Ala Pro Lys Met Ser Leu
 65                  70                  75                  80

Leu Asp Tyr Leu Leu Leu Ile Val Asp Pro Gln Ser Cys Asn Asp Asp
                 85                  90                  95

Val Arg Lys Asp Leu Lys Thr Lys Leu Met Ala Gly Lys Met Thr Ile
                100                 105                 110

Arg Gln Ala Ala Arg Pro Arg Ile Arg Gln Leu Leu Glu Asn Leu Lys
            115                 120                 125

Leu Lys Cys Ala Glu Val Trp Asp Asn Glu Met Ser Arg Leu Thr Glu
130                 135                 140

Arg His Leu Thr Phe Leu Asp Leu Cys Glu Glu Asn Ser Leu Val Tyr
145                 150                 155                 160

Lys Val Thr Gly Lys Ser Asp Arg Gly Arg Asn Ala Lys Lys Tyr Asp
                165                 170                 175

Thr Thr Leu Phe Lys Ile Tyr Glu Glu Asn Lys Lys Phe Ile Glu Phe
                180                 185                 190

Pro His Leu Pro Leu Val Lys Val Ser Gly Ala Lys Glu Tyr Ala
            195                 200                 205

Val Pro Met Glu His Leu Glu Val His Glu Lys Pro Gln Arg Tyr Lys
210                 215                 220

Asn Arg Ile Asp Leu Val Met Gln Asp Lys Phe Leu Lys Arg Ala Thr
225                 230                 235                 240

Arg Lys Pro His Asp Tyr Lys Glu Asn Thr Leu Lys Met Leu Lys Glu
                245                 250                 255

Leu Asp Phe Ser Ser Glu Glu Leu Asn Phe Val Glu Arg Phe Gly Leu
            260                 265                 270

Cys Ser Lys Leu Gln Met Ile Glu Cys Pro Gly Lys Val Leu Lys Glu
            275                 280                 285

Pro Met Leu Val Asn Ser Val Asn Glu Gln Ile Lys Met Thr Pro Val
    290                 295                 300

Ile Arg Gly Phe Gln Glu Lys Gln Leu Asn Val Val Pro Glu Lys Glu
305                 310                 315                 320

Leu Cys Cys Ala Val Phe Val Val Asn Glu Thr Ala Gly Asn Pro Cys
                325                 330                 335

Leu Glu Glu Asn Asp Val Val Lys Phe Tyr Thr Glu Leu Ile Gly Gly
            340                 345                 350

Cys Lys Phe Arg Gly Ile Arg Ile Gly Ala Asn Glu Asn Arg Gly Ala
            355                 360                 365

Gln Ser Ile Met Tyr Asp Ala Thr Lys Asn Glu Tyr Ala Phe Tyr Lys
    370                 375                 380

Asn Cys Thr Leu Asn Thr Gly Ile Gly Arg Phe Glu Ile Ala Ala Thr
385                 390                 395                 400

Glu Ala Lys Asn Met Phe Glu Arg Leu Pro Asp Lys Glu Gln Lys Val
                405                 410                 415

Leu Met Phe Ile Ile Ile Ser Lys Arg Gln Leu Asn Ala Tyr Gly Phe
```

```
                 420             425             430
Val Lys His Tyr Cys Asp His Thr Ile Gly Val Ala Asn Gln His Ile
        435                 440                 445
Thr Ser Glu Thr Val Thr Lys Ala Leu Ala Ser Leu Arg His Glu Lys
    450                 455                 460
Gly Ser Lys Arg Ile Phe Tyr Gln Ile Ala Leu Lys Ile Asn Ala Lys
465                 470                 475                 480
Leu Gly Gly Ile Asn Gln Glu Leu Asp Trp Ser Glu Ile Ala Glu Ile
                485                 490                 495
Ser Pro Glu Glu Lys Glu Arg Arg Lys Thr Met Pro Leu Thr Met Tyr
            500                 505                 510
Val Gly Ile Asp Val Thr His Pro Thr Ser Tyr Ser Gly Ile Asp Tyr
            515                 520                 525
Ser Ile Ala Ala Val Val Ala Ser Ile Asn Pro Gly Gly Thr Ile Tyr
            530                 535                 540
Arg Asn Met Ile Val Thr Gln Glu Glu Cys Arg Pro Gly Glu Arg Ala
545                 550                 555                 560
Val Ala His Gly Arg Glu Arg Thr Asp Ile Leu Glu Ala Lys Phe Val
                565                 570                 575
Lys Leu Leu Arg Glu Phe Ala Glu Asn Asn Asp Asn Arg Ala Pro Ala
            580                 585                 590
His Ile Val Val Tyr Arg Asp Gly Val Ser Asp Ser Glu Met Leu Arg
            595                 600                 605
Val Ser His Asp Glu Leu Arg Ser Leu Lys Ser Glu Val Lys Gln Phe
    610                 615                 620
Met Ser Glu Arg Asp Gly Glu Asp Pro Glu Pro Lys Tyr Thr Phe Ile
625                 630                 635                 640
Val Ile Gln Lys Arg His Asn Thr Arg Leu Leu Arg Arg Met Glu Lys
                645                 650                 655
Asp Lys Pro Val Val Asn Lys Asp Leu Thr Pro Ala Glu Thr Asp Val
            660                 665                 670
Ala Val Ala Val Lys Gln Trp Glu Glu Asp Met Lys Glu Ser Lys
            675                 680                 685
Glu Thr Gly Ile Val Asn Pro Ser Ser Gly Thr Thr Val Asp Lys Leu
    690                 695                 700
Ile Val Ser Lys Tyr Lys Phe Asp Phe Phe Leu Ala Ser His His Gly
705                 710                 715                 720
Val Leu Gly Thr Ser Arg Pro Gly His Tyr Thr Val Met Tyr Asp Asp
                725                 730                 735
Lys Gly Met Ser Gln Asp Glu Val Tyr Lys Met Thr Tyr Gly Leu Ala
            740                 745                 750
Phe Leu Ser Ala Arg Cys Arg Lys Pro Ile Ser Leu Pro Val Pro Val
            755                 760                 765
His Tyr Ala His Leu Ser Cys Glu Lys Ala Lys Glu Leu Tyr Arg Thr
    770                 775                 780
Tyr Lys Glu His Tyr Ile Gly Asp Tyr Ala Gln Pro Arg Thr Arg His
785                 790                 795                 800
Glu Met Glu His Phe Leu Gln Thr Asn Val Lys Tyr Pro Gly Met Ser
                805                 810                 815
Phe Ala

<210> SEQ ID NO 14
<211> LENGTH: 63
```

-continued

```
<212> TYPE: PRT
<213> ORGANISM: Caenorhabditis elegans

<400> SEQUENCE: 14

Trp Val Gly Lys Leu Gln Phe Lys Ser Gln Lys Ser Lys Leu Gln Ala
 1               5                  10                  15

Asp Ile Tyr Glu Asp Ser Lys Asn Glu Arg Thr Glu Phe Thr Leu Val
             20                  25                  30

Ile Cys Thr Met Cys Asn Gln Lys Thr Arg Gly Ile Thr Ser Lys Gln
         35                  40                  45

Lys Asp Ala Lys Asn Leu Ala Ala Trp Leu Met Trp Lys Ala Leu
 50                  55                  60
```

RNA INTERFERENCE PATHWAY GENES AS TOOLS FOR TARGETED GENETIC INTERFERENCE

RELATED APPLICATION INFORMATION

This application claims priority to U.S. application Ser. No. 09/689,992 filed Oct. 13, 2000, now abandoned, which claims priorty to provisional application Ser. No. 60/159,776, filed Oct. 15, 1999, and 60/193,218, filed Mar. 30, 2000.

STATEMENT AS TO FEDERALLY SPONSORED RESEARCH

Funding for the work described herein was provided by the federal government (GM58800 and GM37706), which has certain rights in the invention.

FIELD OF THE INVENTION

This invention relates to the discovery of genes whose expression products are involved in mediation of genetic interference.

BACKGROUND OF THE INVENTION

All eukaryotic organisms share similar mechanisms for information transfer from DNA to RNA to protein. RNA interference represents an efficient mechanism for inactivating this transfer process for a specific targeted gene. Targeting is mediated by the sequence of the RNA molecule introduced to the cell. Double-stranded (ds) RNA can induce sequence-specific inhibition of gene function (genetic interference) in several organisms including the nematode, *C. elegans* (Fire, et al., 1998, *Nature* 391:806-811), plants, *trypanosomes, Drosophila*, and *planaria* (Waterhouse et al., 1998, *Proc. Natl. Acad. Sci. USA* 94:13959-13964; Ngo et al., 1998, *Proc. Natl. Acad. Sci. USA* 95:14687-14692; Kennerdell and Carthew, 1998, *Cell* 95:1017-1026; Misquitta and Patterson, 1999, *Proc. Natl. Acad. Sci. USA* 96: 1451-1456; Sanchez-Alvorado and Newmark, 1999, *Proc. Natl. Acad. Sci. USA* 96:5049-5054). The discovery that dsRNA can induce genetic interference in organisms from several distinct phyla suggests a conserved mechanism and perhaps a conserved physiological role for the interference process. Although several models of RNAi have been proposed (Baulcombe, 1999, *Curr. Biol.* 9:R599-R601; Sharp, 1999, *Genes & Dev.* 13:139-141) the mechanisms of action of specific components of the pathway are not known.

Attempts to overexpress a gene (e.g., a transgene) often lead only to transient expression of the gene. Furthermore, the even more undesirable effect of "cosuppression" can occur in which a corresponding endogenous copy of the transgene becomes inactivated. In some cases, transgene silencing leads to problems with the commercial or therapeutic application of transgenic technology to alter the genetic makeup of a cell, organism, or human patient.

SUMMARY OF THE INVENTION

The present invention relates to the discovery of RNA interference (RNAi) pathway genes which are involved in mediating double-stranded RNA-dependent gene silencing (genetic interference). RNAi requires a set of conserved cellular factors to suppress gene expression. These factors are the components of the RNAi pathway. The RNAi pathway mutations and genes described herein (e.g., rde-1, rde-2, rde-3, rde-4, rde-5, mut-2, and mut-7), and their protein products (e.g., RDE-1 and RDE-4) are useful tools for investigating the mechanisms involved in RNAi and developing methods of modulating the RNAi pathway. The sequences and methods described herein are useful for modulating the RNAi pathway and may be used in conjunction with other methods involving the use of genetic inhibition by dsRNA (e.g., see U.S. Ser. No. 09/215,257, filed Dec. 18, 1998, incorporated herein by reference in its entirety).

RNAi pathway components (e.g., RDE-1, RDE-4) provide activities necessary for interference. These activities may be absent or not sufficiently activated in many cell types, including those of organisms such as humans in which genetic interference may have potential therapeutic value. Components of the RNAi pathway in *C. elegans* may be sufficient when provided through transgenesis or as direct RNA:protein complexes to activate or directly mediate genetic interference in heterologous cells that are deficient in RNAi.

Nucleic acid sequences encoding RNAi pathway components (e.g., RDE-1, RDE-4) are useful, e.g., for studying the regulation of the RNAi pathway. Such sequences can also be used to generate knockout strains of animals such as *C. elegans*.

The nucleic acids of the invention include nucleic acids that hybridize, e.g., under stringent hybridization conditions (as defined herein), to all or a portion of the nucleotide sequence of SEQ ID NO:1 (FIG. 5A-C) or its complement; SEQ ID NO:2 (FIG. 6A-D) or its complement, or SEQ ID NO:4 or its complement. The hybridizing portion of the hybridizing nucleic acids are preferably 20, 30, 50, or 70 bases long. Preferably, the hybridizing portion of the hybridizing nucleic acid is 80%, more preferably 95%, or even 98% or 100% identical to the sequence of a portion or all of a nucleic acid encoding an RDE-1 polypeptide or an RDE-4 polypeptide. Hybridizing nucleic acids of the type described above can be used as a cloning probe, a primer (e.g., a PCR primer), or a diagnostic probe. Preferred hybridizing nucleic acids encode a polypeptide having some or all of the biological activities possessed by a naturally-occurring RDE-1 polypeptide or an RDE-4 polypeptide e.g., as determined in the assays described below.

Hybridizing nucleic acids may encode a protein that is shorter or longer than the RDE-1 protein or RDE-4 protein described herein. Hybridizing nucleic acids may also encode proteins that are related to RDE-1 or RDE-4 (e.g., proteins encoded by genes that include a portion having a relatively high degree of identity to the rde-1 gene or rde-4 gene described herein).

The invention also features purified or isolated RDE-1 polypeptides and RDE-4 polypeptides. RDE-1 and RDE-4 polypeptides are useful for generating and testing antibodies that specifically bind to an RDE-1 or an RDE-4. Such antibodies can be used, e.g., for studying the RNAi pathway in *C. elegans* and other organisms. As used herein, both "protein" and "polypeptide" mean any chain of amino acids, regardless of length or post-translational modification (e.g., glycosylation or phosphorylation). Thus, the term "RNAi pathway polypeptide" includes a full-length, naturally occurring RNAi pathway polypeptide such as RDE-1 protein or RDE-4 protein, as well as recombinantly or synthetically produced polypeptides that correspond to a full-length, naturally occurring RDE-1 protein, RDE-4 protein, or to particular domains or portions of a naturally occurring RNAi pathway protein.

RNAi pathway mutations and strains harboring those mutations (e.g., rde-1, rde-2, rde-3, rde-4, rde-5) are useful for studying the RNAi pathway, including identification of modulators of the RNAi pathway.

RNAi pathway components (e.g., those associated with mut-7 and rde-2) can be used to desilence or prevent silencing of transgenes. To facilitate this function, such RNAi pathway components are inhibited using specific inhibitors of an RNAi pathway gene or its product.

In one embodiment, the invention includes an isolated nucleic acid molecule comprising a nucleotide sequence encoding an RDE-1 polypeptide. The nucleic acid molecule hybridizes under high stringency conditions to the nucleic acid sequence of Genbank Accession No. AF180730 (SEQ ID NO:2) or its complement, or the sequence of SEQ ID NO:1 or its complement. In one embodiment, the isolated nucleic acid can complement an rde-1 mutation. The invention also encompasses an isolated nucleic acid whose nucleotide sequence encodes the amino acid sequence of SEQ ID NO:3.

The invention also encompasses a substantially pure RDE-1 polypeptide encoded by the isolated nucleic acids described herein.

The invention features an antibody that specifically binds to an RDE-1 polypeptide.

The invention also includes a method of enhancing the expression of a transgene in a cell, the method comprising decreasing activity of the RNAi pathway. In one embodiment of this invention, rde-2 expression or activity is decreased.

The invention also features an isolated nucleic acid molecule comprising a nucleotide sequence encoding an RDE-4 polypeptide, wherein the nucleic acid molecule hybridizes under high stringency conditions to the nucleic acid sequence of SEQ ID NO:4 or its complement. The invention also encompasses an isolated nucleic acid encoding an RDE-4 polypeptide, wherein the nucleic acid can complement an rde-4 mutation. The invention also encompasses an isolated nucleic acid encoding an RDE-4 polypeptide, in which the nucleotide sequence encodes the amino acid sequence of SEQ ID NO:5.

The invention also features a substantially pure RDE-4 polypeptide encoded by the isolated nucleic acids described herein.

In another embodiment the invention features an antibody that specifically binds to an RDE-4 polypeptide.

The invention also features a method of preparing an RNAi agent, the method includes incubating a dsRNA in the presence of an RDE-1 protein and an RDE-4 protein.

The invention also features a method of inhibiting the activity of a gene by introducing an RNAi agent into a cell, such that the dsRNA component of the RNAi agent is targeted to the gene. In another embodiment of the invention, the cell contains an exogenous RNAi pathway sequence. The exogenous RNAi pathway sequence can be an RDE-1 polypeptide or an RDE-4 polypeptide. In still another embodiment, a dsRNA is introduced into a cell containing an exogenous RNAi pathway sequence such as nucleic acid sequence expressing an RDE-1 or RDE-4.

An RNAi pathway component is a protein or nucleic acid that is involved in promoting dsRNA-mediated genetic interference. A nucleic acid component can be an RNA or DNA molecule. A mutation in a gene encoding an RNAi pathway component may decrease or increase RNAi pathway activity.

An RNAi pathway protein is a protein that is involved in promoting dsRNA mediated genetic interference.

A "substantially pure DNA" is a DNA that is not immediately contiguous with (i.e., covalently linked to) both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by PCR (polymerase chain reaction) or restriction endonuclease digestion) independent of other sequences. It also includes a recombinant DNA which is part of a hybrid gene encoding additional polypeptide sequences.

By "inhibited RNAi pathway" is meant decreased inhibitory activity of a dsRNA which results in at least two-fold less inhibition by a dsRNA relative to its ability to cause inhibition in a wild type cell. Techniques for measuring RNAi pathway activity are described herein. The pathway can be inhibited by inhibiting a component of the pathway (e.g., RDE-1) or mutating the component so that its function is reduced.

A "substantially pure polypeptide" is a polypeptide, e.g., an RNAi pathway polypeptide or fragment thereof, that is at least 60%, by weight, free from the proteins and naturally-occurring organic molecules with which it is naturally associated. Preferably, the preparation is at least 75%, more preferably at least 90%, and most preferably at least 99%, by weight, RNAi pathway polypeptide or fragment. A substantially pure RNAi pathway polypeptide or fragment thereof is obtained, for example, by extraction from a natural source; by expression of a recombinant nucleic acid encoding an RNAi pathway polypeptide or fragment thereof; or by chemically synthesizing the polypeptide or fragment. Purity can be measured by any appropriate method, e.g., column chromatography, polyacrylamide gel electrophoresis, or HPLC analysis.

By "specifically binds" is meant a molecule that binds to a particular entity, e.g., an RNAi pathway polypeptide, but which does not substantially recognize or bind to other molecules in a sample, e.g., a biological sample, which includes the particular entity, e.g., RDE-1.

An RNAi agent is a dsRNA molecule that has been treated with those components of the RNAi pathway that are required to confer RNAi activity on the dsRNA. For example, treatment of a dsRNA under conditions that include RDE-1 and RDE-4 results in an RNAi agent. Injection of such an agent into an animal that is mutant for RDE-1 and RDE-4 will result in activation of the RNAi pathway with respect to a targeted gene. Typically, the dsRNA used to trigger the formation of the RNAi agent is selected to be an RNA corresponding to all or a portion of the nucleotide sequence of the targeted gene.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

BRIEF DESCRIPTION OF THE DRAWINGS

FIG. 2A is a graphical representation of experiments investigating the sensitivity of rde and mut strains to RNAi by microinjection. The RNA species indicated above each graph was injected at high concentration (pos-1: 7 mg/ml, par-2: 3 mg/ml, sqt-3: 7 mg/ml). The strains receiving injection are indicated at the left and the horizontal bar graphs reflect the percent of progeny that exhibited genetic interference. The Unc marker mutants used are also indicated. The percent embryonic lethality of F1 progeny is plotted as shaded bars and the fraction of affected progeny is indicated at the right of each graph.

FIG. 2B is a graphical representation of experiments demonstrating that animals homozygous for rde and mut alleles are resistant to RNAi targeting maternally expressed genes, pos-1 and par-2. The percent embryonic lethality of F1 progeny is plotted as shaded bars and the fraction of affected progeny is indicated at the right of each graph.

FIG. 4B (1-3) is an depiction of regions of homology between the predicted sequence of RDE-1 and four related proteins. The sequences are RDE-1 (*C. elegans*; Genbank Accession No. AF180730) (SEQ ID NO:13), F48F7.1 (*C. elegans*; Genbank Accession No. Z69661) (SEQ ID NO:9), eIF2C (rabbit; Genbank Accession No. AF005355) (SEQ ID NO:10), ZWILLE (*Arabidopsis*; Genbank Accession No. AJ223508) (SEQ ID NO:6), and Sting (*Drosophila*; Genbank Accession No. AF145680) (SEQ ID NO:7). Identities with RDE-1 are shaded in black, and identities among the homologs are shaded in gray.

FIGS. 5A-5C are an illustration of the genomic sequence from cosmid KO8H10 (Genbank accession Z83113.1; SEQ ID NO:1) corresponding to the rde-1 gene from the first nucleotide of 5' untranslated region to the polyadenylation site.

FIGS. 6A-6D are an illustration of the cDNA sequence of rde-1 (SEQ ID NO:2), including the first 20 nucleotides constituting the 5' untranslated sequence (5'UTR) and the predicted amino acid sequence encoded by rde-1 (RDE-1; SEQ ID NO:3). The nucleotide sequence is numbered starting with the first nucleotide of the translated region.

FIG. 9A depicts experiments of a the genetic scheme to determine if the wild-type activities of rde-1, rde-2, rde-4, and mut-7 are sufficient in the injected animal for interference among the F1 self progeny. The fraction shown represents the number of RNAi affected animals over the total number of cross progeny scored for each genotype class.

FIG. 9B depicts experiments designed to determine the requirements for rde-1, rde-2, rde-4, and mut-7 in F2 (FIG. 10A) and F1 (FIG. 10B) interference. The fraction shown represents the number of RNAi affected animals over the total number of cross progeny scored for each genotype class.

FIGS. 10A-10B are a depiction of the cDNA sequence of a wild type rde-4 nucleic acid sequence (SEQ ID NO:4) and the predicted RDE-4 amino acid sequence (SEQ ID NO:5) of *C. elegans*. "*" indicates ambiguous base assignment.

DETAILED DESCRIPTION

Figure 1A:
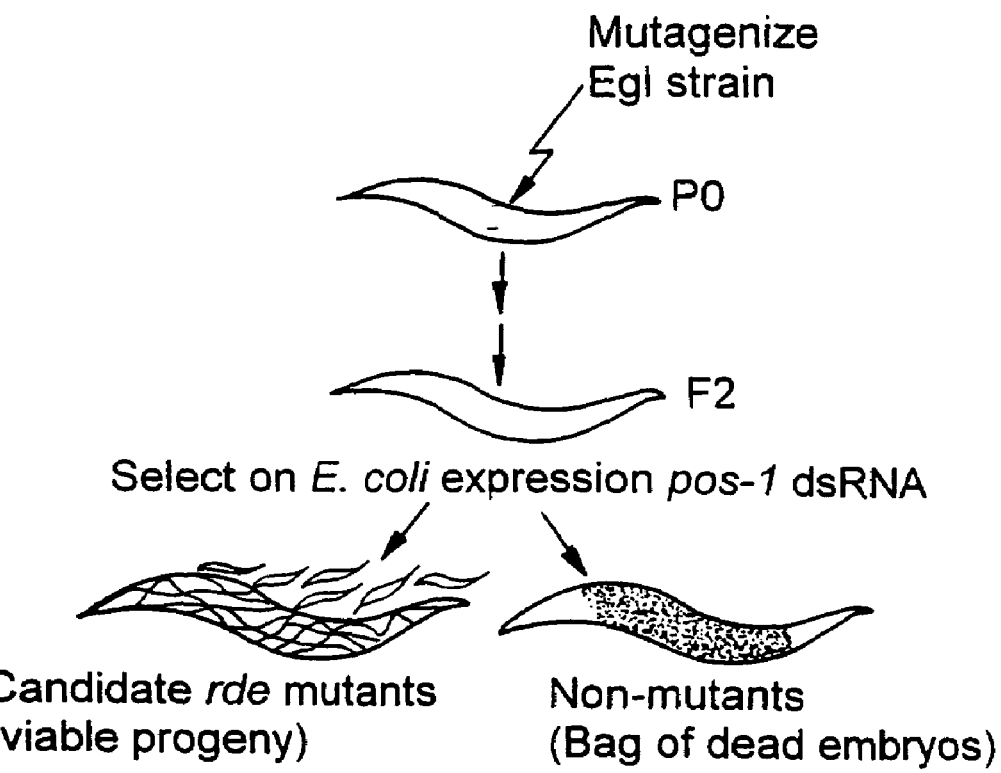
FIG. 1A illustrates the genetic scheme used to identify rde mutants.

Mutations have been discovered that identify genes involved in dsRNA-mediated genetic interference (RNAi). RNAi pathway genes encode products involved in genetic interference and are useful for mediating or enhancing genetic interference. These genes encode mediators of double-stranded RNA-mediated interference. The mediators can be nucleic acid or protein. RNAi pathway genes are also useful for mediating specific processes, e.g., a gene that mediates dsRNA uptake by cells may be useful for transporting other RNAs into cells or for facilitating entry of agents such as drugs into cells. The methods and examples described below illustrate the identification of RNAi pathway components, the uses of RNAi pathway components, mutants, genes and their products.

Identification of an RNAi-Deficient Mutants and an RNAi Pathway Gene, rde-1

RNAi pathway genes were identified using screens for *C. elegans* strains mutant for RNAi (Examples 2 and 3). The mutations were further characterized for germline and somatic effects, effects on transposon mobilization, X chromosome loss and transgene silencing, and target tissue activity (Examples 4 and 5).

The rde-1 gene was identified using YACs (yeast artificial chromosomes) and cosmids to rescue rde-1 mutants. Based on the identified sequence, a cDNA sequence was identified in a C. elegans cDNA library and the complete cDNA sequence determined (Example 6).

Identification of RNAi Pathway Genes Homologous to rde-1, rde-2, rde-3, and rde-4

RNAi pathway genes from C. elegans (such as those described herein) and from other organisms (e.g. plant, mammalian, especially human) are useful for the elucidation of the biochemical pathways involved in genetic interference and for developing the uses of RNAi pathway genes described herein.

Several approaches can be used to isolate RNAi pathway genes including two-hybrid screens, complementation of C. elegans mutants by expression libraries of cloned heterologous (e.g., plant, mammalian, human) cDNAs, polymerase chain reactions (PCR) primed with degenerate oligonucleotides, low stringency hybridization screens of heterologous cDNA or genomic libraries with a C. elegans RNAi pathway gene, and database screens for sequences homologous to an RNAi pathway gene. Hybridization is performed under stringent conditions. Alternatively, a labeled fragment can be used to screen a genomic library derived from the organism of interest, again, using appropriately stringent conditions. Such stringent conditions are well known, and will vary predictably depending on the specific organisms from which the library and the labeled sequences are derived.

Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular SSC or SSPE concentration. Then assume that 1% mismatching results in 1° C. decrease in the $T_m$ and reduce the temperature of the final wash accordingly (for example, if sequences with ≧95% identity with the probe are sought, decrease the final wash temperature by 5° C.). Note that this assumption is very approximate, and the actual change in $T_m$ can be between 0.5° and 1.5° C. per 1% mismatch.

As used herein, high stringency conditions include hybridizing at 68° C. in 5×SSC/5× Denhardt solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the desired level of identity between the probe and the target nucleic acid.

For guidance regarding such conditions see, for example, Sambrook et al., 1989, Molecular Cloning, A Laboratory Manual, Cold Springs Harbor Press, N.Y.; and Ausubel et al. (eds.), 1995, Current Protocols in Molecular Biology, (John Wiley & Sons, N.Y.) at Unit 2.10.

Methods of screening for and identifying homologs of C. elegans RNAi genes (e.g., rde-1) are known in the art. For example, complementation of mutants, described in the Examples can be performed using nucleic acid sequences from organisms other than C. elegans. Methods of inhibiting expression of a target gene in a cell using dsRNA are known in the art and are exemplified in U.S. Ser. No. 09/215,257, filed Dec. 18, 1998, which is incorporated herein by reference in its entirety.

Another method of screening is to use an identified RNAi pathway gene sequence to screen a cDNA or genomic library using low stringency hybridizations. Such methods are known in the art.

PCR with degenerate oligonucleotides is another method of identifying homologs of RNAi pathway genes (e.g., human rde-1). Homologs of an RNAi pathway gene identified in other species are compared to identify specific regions with a high degree of homology (as in the sequence comparison shown in FIG. 4). These regions of high homology are selected for designing PCR primers that maximize possible base-pairing with heterologous genes. Construction of such primers involves the use of oligonucleotide mixtures that account for degeneracy in the genetic code, i.e., allow for the possible base changes in an RNAi pathway gene that does not affect the amino acid sequence of the RNAi pathway protein. Such primers may be used to amplify and clone possible RNAi pathway gene fragments from DNA isolated from another organism (e.g., mouse or human). The latter are sequenced and those encoding protein fragments with high degrees of homology to fragments of the RNAi pathway protein are used as nucleic acid probes in subsequent screens of genomic DNA and cDNA libraries (e.g., mouse or human). Full-length genes and cDNAs having substantial homology to the previously identified RNAi pathway gene are identified in these screens.

To produce an RNAi pathway gene product (e.g., RDE-1) a sequence encoding the gene is placed in an expression vector and the gene expressed in an appropriate cell type. The gene product is isolated from such cell lines using methods known to those in the art, and used in the assays and procedures described herein. The gene product can be a complete RNAi pathway protein (e.g., RDE-1) or a fragment of such a protein.

Methods of Expressing RNAi Pathway Proteins

Full-length polypeptides and polypeptides corresponding to one or more domains of a full-length RNAi pathway protein, e.g., the RNA-binding domain of RDE-4, are also within the scope of the invention. Also within the invention are fusion proteins in which a portion (e.g., one or more domains) of an RDE-1 or RDE-4) is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of of an RNAi pathway protein is joined in-frame to a nucleotide sequence encoding the fusion partner. Fusion partners include, but are not limited to, the constant region of an immunoglobulin (IgFc). A fusion protein in which an RNAi pathway polypeptide is fused to IgFc can be more stable and have a longer half-life in the body than the polypeptide on its own.

In general, RNAi pathway proteins (e.g., RDE-1, RDE-4) according to the invention can be produced by transformation (transfection, transduction, or infection) of a host cell with all or part of an RNAi pathway protein-encoding DNA fragment (e.g., one of the cDNAs described herein) in a suitable expression vehicle. Suitable expression vehicles include: plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LAC-SWITCH™ Inducible Expression System (Stratagene; LaJolla, Calif.).

Those skilled in the field of molecular biology will understand that any of a wide variety of expression systems can be used to provide the recombinant protein. The precise host cell used is not critical to the invention. The RNAi pathway protein can be produced in a prokaryotic host (e.g., *E. coli* or *B. subtilis*) or in a eukaryotic host (e.g., *Saccharomyces* or *Pichia*; mammalian cells, e.g., COS, NIH 3T3 CHO, BHK, 293, or HeLa cells; or insect cells).

Proteins and polypeptides can also be produced in plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors*: A Laboratory Manual (P. H. Pouwels et al., 1985, Supp. 1987).

The host cells harboring the expression vehicle can be cultured in conventional nutrient media adapted as need for activation of a chosen gene, repression of a chosen gene, selection of transformants, or amplification of a chosen gene.

One preferred expression system is the mouse 3T3 fibroblast host cell transfected with a pMAMneo expression vector (Clontech, Palo Alto, Calif.). pMAMneo provides an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an RNAi pathway protein would be inserted into the pMAMneo vector in an orientation designed to allow expression. The recombinant RNAi pathway protein would be isolated as described herein. Other preferable host cells that can be used in conjunction with the pMAMneo expression vehicle include COS cells and CHO cells (ATCC Accession Nos. CRL 1650 and CCL 61, respectively).

RNAi pathway polypeptides can be produced as fusion proteins. For example, the expression vector pUR278 (Ruther et al., *EMBO J.* 2:1791, 1983), can be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect cell expression system, *Autographa californica* nuclear polyhidrosis virus (AcNPV), which grows in *Spodoptera frugiperda* cells, is used as a vector to express foreign genes. An RNAi pathway protein coding sequence can be cloned individually into non-essential regions (for example the polyhedrin gene) of the virus and placed under control of an AcNPV promoter, e.g., the polyhedrin promoter. Successful insertion of a gene encoding an RNAi pathway polypeptide or protein will result in inactivation of the polyhedrin gene and production of non-occluded recombinant virus (i.e., virus lacking the proteinaceous coat encoded by the polyhedrin gene). These recombinant viruses are then used to infect *spodoptera frugiperda* cells in which the inserted gene is expressed (see, e.g., Smith et al., *J. Virol.* 46:584, 1983; Smith, U.S. Pat. No. 4,215,051).

In mammalian host cells, a number of viral-based expression systems can be utilized. When an adenovirus is used as an expression vector, the RNAi pathway protein nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an RNAi pathway gene product in infected hosts (see, e.g., Logan, Proc. Natl. Acad. Sci. USA 81:3655, 1984).

Specific initiation signals may be required for efficient translation of inserted nucleic acid sequences. These signals include the ATG initiation codon and adjacent sequences. In cases where an entire native RNAi pathway protein gene or cDNA, including its own initiation codon and adjacent sequences, is inserted into the appropriate expression vector, no additional translational control signals may be needed. In other cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., Methods in Enzymol. 153:516, 1987).

RNAi pathway polypeptides can be expressed directly or as a fusion with a heterologous polypeptide, such as a signal sequence or other polypeptide having a specific cleavage site at the N- and/or C-terminus of the mature protein or polypeptide. Included within the scope of this invention are RNAi pathway polypeptides with a heterologous signal sequence. The heterologous signal sequence selected should be one that is recognized and processed, i.e., cleaved by a signal peptidase, by the host cell. For prokaryotic host cells a prokaryotic signal sequence is selected, for example, from the group of the alkaline phosphatase, penicillinase, 1 pp, or heat-stable enterotoxin II leaders. For yeast secretion a yeast invertase, alpha factor, or acid phosphatase leaders may be selected. In mammalian cells, it is generally desirable to select a mammalian signal sequences.

A host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, 3T3, W138, and in particular, choroid plexus cell lines.

Alternatively, an RNAi pathway protein can be produced by a stably-transfected mammalian cell line. A number of vectors suitable for stable transfection of mammalian cells are available to the public, see, e.g., Pouwels et al. (supra); methods for constructing such cell lines are also publicly available, e.g., in Ausubel et al. (supra. In one example, cDNA encoding an RNAi pathway protein (e.g., RDE-1 or RDE-4) is cloned into an expression vector that includes the dihydrofolate reductase (DHFR) gene. Integration of the plasmid and, therefore, the RNAi pathway protein-encoding gene into the host cell chromosome is selected for by including 0.01-300 µM methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

A number of other selection systems can be used, including but not limited to the herpes simplex virus thymidine kinase, hypoxanthine-guanine phosphoribosyl-transferase, and adenine phosphoribosyltransferase genes can be employed in tk, hgprt, or aprt cells, respectively. In addition, gpt, which confers resistance to mycophenolic acid (Mulligan et al., *Proc. Natl. Acad. Sci. USA,* 78:2072, 1981); neo, which confers resistance to the aminoglycoside G-418 (Colberre-Garapin et al., *J. Mol. Biol.,* 150:1, 1981); and hygro, which confers resistance to hygromycin (Santerre et al., *Gene,* 30:147, 1981), can be used.

Alternatively, any fusion protein can be readily purified by utilizing an antibody specific for the fusion protein being expressed. For example, a system described in Janknecht et al., *Proc. Natl. Acad. Sci. USA,* 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns, and histidine-tagged proteins are selectively eluted with imidazole-containing buffers.

Alternatively, an RNAi pathway protein or a portion thereof, can be fused to an immunoglobulin Fc domain. Such a fusion protein can be readily purified using a protein A column.

Antibodies that Recognize RNAi Pathway Proteins

Techniques for generating both monoclonal and polyclonal antibodies specific for a particular protein are well known. The invention also includes humanized or chimeric antibodies, single chain antibodies, Fab fragments, F(ab')$_2$ fragments, and molecules produced using a Fab expression library.

Antibodies can be raised against a short peptide epitope of an RNAi pathway gene (e.g., rde-1), an epitope linked to a known immunogen to enhance immunogenicity, a long fragment of an RNAi pathway gene, or the intact protein. Such antibodies are useful for e.g., localizing RNAi pathway polypeptides in tissue sections or fractionated cell preparations, determining whether an RNAi pathway gene is expressed (e.g., after transfection with an RNAi pathway gene), and evaluating the expression of an RNAi pathway gene in disorders (e.g., genetic conditions) where the RNAi pathway may be affected.

An isolated RNAi pathway protein (e.g., RDE-1), or a portion or fragment thereof, can be used as an immunogen to generate antibodies that bind to an RNAi pathway protein using standard techniques for polyclonal and monoclonal antibody preparation. The RNAi pathway immunogen can also be a mutant RNAi pathway protein or a fragment of a mutant RNAi pathway protein. A full-length RNAi pathway protein can be used or, alternatively, antigenic peptide fragments of RNAi pathway protein can be used as immunogens. The antigenic peptide of an RNAi pathway protein comprises at least 8 (preferably 10, 15, 20, or 30) amino acid residues. In the case of RDE-1, these residues are drawn from the amino acid sequence shown in SEQ ID NO:3 and encompass an epitope such that an antibody raised against the peptide forms a specific immune complex with RDE-1. Preferred epitopes encompassed by the antigenic peptide are regions of the protein that are located on the surface of the protein, e.g., hydrophilic regions.

An RNAi pathway protein immunogen typically is used to prepare antibodies by immunizing a suitable subject (e.g., rabbit, goat, mouse or other mammal) with the immunogen. An appropriate immunogenic preparation can contain, for example, recombinantly expressed RNAi pathway protein or a chemically synthesized RNAi polypeptide. The preparation can further include an adjuvant, such as Freund's complete or incomplete adjuvant, or similar immunostimulatory agent. Immunization of a suitable subject with an immunogenic RNAi pathway protein preparation induces a polyclonal anti-RNAi pathway protein antibody response.

Polyclonal antibodies that recognize an RNAi pathway protein ("RNAi pathway antibodies") can be prepared as described above by immunizing a suitable subject with an RNAi pathway protein immunogen. The RNAi pathway antibody titer in the immunized subject can be monitored over time by standard techniques, such as with an enzyme-linked immunosorbent assay (ELISA) using immobilized RNAi pathway protein from which the immunogen was derived. If desired, the antibody molecules directed against the RNAi pathway protein can be isolated from the mammal (e.g., from the blood) and further purified by well-known techniques, such as protein A chromatography to obtain the IgG fraction. At an appropriate time after immunization, e.g., when the RNAi pathway antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985), *Monoclonal Antibodies and Cancer Therapy,* Alan R. Liss, Inc., pp. 77-96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an RNAi pathway immunogen as described above, and the culture supernatants of the resulting hybridoma cells are screened to identify a hybridoma producing a monoclonal antibody that binds to the RNAi pathway protein.

Any of the many well known protocols used for fusing lymphocytes and immortalized cell lines can be applied for the purpose of generating a monoclonal antibody against an RNAi pathway protein (see, e.g., *Current Protocols in Immunology*, supra; Galfre et al., 1977, *Nature* 266:55052; R. H. Kenneth, in *Monoclonal Antibodies: A New Dimension In Biological Analyses*, Plenum Publishing Corp., New York, N.Y., 1980; and Lerner, 1981, *Yale J. Biol. Med.,* 54:387-402. Moreover, one in the art will appreciate that there are many variations of such methods which also would be useful. Hybridoma cells producing a monoclonal antibody of the invention are detected by screening the hybridoma culture supernatants for antibodies that bind to the RNAi pathway protein, e.g., using a standard ELISA assay.

Alternative to preparing monoclonal antibody-secreting hybridomas, a monoclonal RNAi pathway antibody can be identified and isolated by screening a recombinant combinatorial immunoglobulin library (e.g., an antibody phage display library) with an RNAi pathway protein to thereby isolate immunoglobulin library members that bind to the RNAi pathway protein. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, *Bio/Technology* 9:1370-1372; Hay et al., 1992, *Hum. Antibod. Hybridomas* 3:81-85; Huse et al., 1989, *Science* 246:1275-1281; Griffiths et al., 1993, *EMBO J.* 12:725-734.

Techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against an RNAi pathway protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., *Science,* 246:1275, 1989) to allow rapid and easy identification of monoclonal Fab fragments with the desired specificity.

Identification of RNAi Pathway Components

RNAi pathway components can be identified in *C. elegans* and other animals (e.g., a mammal) using the methods described in the Examples below. Pathway components can also be identified using methods known in the art and the information provided herein. Such components include those involved in protein:protein and protein:RNA interactions. Specifically, RDE-1 can be used to identify additional proteins and RNA molecules that bind to the RDE-1 protein and so facilitate genetic interference.

The RNAi pathway mutant strains described herein (e.g., rde-1, rde-2, rde-3, rde-4, and rde-5; also mut-2 and mut-7) can be used in genetic screens to identify additional RNAi pathway components. For example, a strain deficient for rde-1 activity can be mutagenized and screened for the recovery of genetic interference. This type of screen can identify allele-specific suppressors in other genes or second site mutations within the rde-1 gene that restore its activity. The resulting strains may define new genes that activate RNAi to overcome or bypass the rde-1 defect. The mutations identified by these methods can be used to identify their corresponding gene sequences.

Two-hybrid screens can also be used to identify proteins that bind to RNAi pathway proteins such as RDE-1. Genes encoding proteins that interact with RDE-1 or human homologs of the *C. elegans* RDE-1, are identified using the two-hybrid method (Fields and Song, 1989, *Nature* 340:245-246; Chien et al., 1991, *Proc. Natl. Acad. Sci. USA* 88:9578-9582; Fields and Stemglanz, 1994, *Trends Genet.* 10:286-292; Bartel and Fields, 1995, *Methods Enzymol.* 254:241-263). DNA encoding the RDE-1 protein is cloned and expressed from plasmids harboring GAL4 or lexA DNA-binding domains and co-transformed into cells harboring lacZ and HIS3 reporter constructs along with libraries of cDNAs that have been cloned into plasmids harboring the GAL4 activation domain. Libraries used for such co-transformation include those made from *C. elegans* or a vertebrate embryonic cell.

Mechanisms of Action of RNAi Pathway Components

Specific cellular functions associated with the RNAi pathway include the specific targeting of a nucleic acid by a dsRNA, uptake of dsRNA, transport of dsRNA, amplification of the dsRNA signal, and genetic interference. The mechanism of interference may involve translation inhibition, or interference with RNA processing. In addition, direct effects on the corresponding gene may contribute to interference. These mechanisms can be identified investigated using the methods described herein and methods known in the art.

Methods of Screening for Molecules that Inhibit the RNAi Pathway

The following assays are designed to identify compounds that are effective inhibitors of the RNAi pathway. Such inhibitors may act by, but are not limited to, binding to an RDE-1 polypeptide (e.g., from *C. elegans*, mouse, or human), binding to intracellular proteins that bind to an RNAi pathway component, compounds that interfere with the interaction between RNAi pathway components including between an RNAi pathway component and a dsRNA, and compounds that modulate the activity or expression of an RNAi pathway gene such as rde-1. An inhibitor of the RNAi pathway can also be used to promote expression of a transgene.

Assays can also be used to identify molecules that bind to RNAi pathway gene regulatory sequences (e.g., promoter sequences), thus modulating gene expression. See, e.g., Platt, 1994, *J. Biol. Chem.* 269:28558-28562, incorporated herein by reference in its entirety.

The compounds which may be screened by the methods described herein include, but are not limited to, peptides and other organic compounds (e.g., peptidomimetics) that bind to an RNAi pathway protein (e.g., that bind to an RDE-1), or inhibit its activity in any way.

Such compounds may include, but are not limited to, peptides; for example, soluble peptides, including but not limited to members of random peptide libraries; (see, e.g., Lam et al., 1991, *Nature* 354:82-94; Houghten et al., 1991, *Nature* 354:84-86), and combinatorial chemistry-derived molecular libraries made of D- and/or L-amino acids, phosphopeptides (including, but not limited to, members of random or partially degenerate, directed phosphopeptide libraries; see e.g., Songyang et al., 1993, *Cell* 72:767-778), and small organic or inorganic molecules.

Organic molecules are screened to identify candidate molecules that affect expression of an RNAi pathway gene (e.g., rde-1), e.g., by interacting with the regulatory region or transcription factors of a gene. Compounds are also screened to identify those that affect the activity of such proteins, (e.g., by inhibiting rde-1 activity) or the activity of a molecule involved in the regulation of, for example, rde-1.

Computer modeling or searching technologies are used to identify compounds, or identify modifications of compounds that modulate the expression or activity of an RNAi pathway protein. For example, compounds likely to interact with the active site of a protein (e.g., RDE-1) are identified. The active site of an RNAi pathway protein can be identified using methods known in the art including, for example, analysis of the amino acid sequence of a molecule, from a study of complexes of an RNAi pathway, with its native ligand (e.g., a dsRNA). Chemical or X-ray crystallographic methods can be used to identify the active site of an RNAi pathway protein by the location of a bound ligand such as a dsRNA.

The three-dimensional structure of the active site is determined. This can be done using known methods, including X-ray crystallography which may be used to determine a complete molecular structure. Solid or liquid phase NMR can be used to determine certain intra-molecular distances. Other methods of structural analysis can be used to determine partial or complete geometrical structures. Geometric structure can be determined with an RNAi pathway protein bound to a natural or artificial ligand which may provide a more accurate active site structure determination.

Computer-based numerical modeling can also be used to predict protein structure (especially of the active site), or be used to complete an incomplete or insufficiently accurate structure. Modeling methods that may be used are, for example, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups are necessary, and can be selected for the model from among the force fields known in physical chemistry. Information on incomplete or less accurate structures determined as above can be incorporated as constraints on the structures computed by these modeling methods.

Having determined the structure of the active site of an RNAi pathway protein (e.g., RDE-1), either experimentally, by modeling, or by a combination of methods, candidate modulating compounds can be identified by searching databases containing compounds along with information on their molecular structure. The compounds identified in such a search are those that have structures that match the active site structure, fit into the active site, or interact with groups defining the active site. The compounds identified by the search are potential RNAi pathway modulating compounds.

These methods may also be used to identify improved modulating compounds from an already known modulating compound or ligand. The structure of the known compound is modified and effects are determined using experimental and computer modeling methods as described above. The altered structure may be compared to the active site structure of an RNAi pathway protein (e.g., an RDE-1) to determine or predict how a particular modification to the ligand or modulating compound will affect its interaction with that protein. Systematic variations in composition, such as by varying side groups, can be evaluated to obtain modified modulating compounds or ligands of preferred specificity or activity.

Other experimental and computer modeling methods useful to identify modulating compounds based on identification of the active sites of an RNAi pathway protein and related transduction and transcription factors will be apparent to those of skill in the art.

Examples of molecular modeling systems are the QUANTA programs, e.g., CHARMm, MCSS/HOOK, and X-LIGAND, (Molecular Simulations, Inc., San Diego, Calif.). QUANTA analyzes the construction, graphic modeling, and analysis of molecular structure. CHARMm analyzes energy minimization and molecular dynamics functions. MCSS/HOOK characterizes the ability of an active site to bind a ligand using energetics calculated via CHARMm. X-LIGAND fits ligand molecules to electron density of protein-ligand complexes. It also allows interactive construction, modification, visualization, and analysis of the behavior of molecules with each other.

Articles reviewing computer modeling of compounds interacting with specific protein can provide additional guidance. For example, see Rotivinen et al., 1988, *Acta Pharmaceutical Fennica* 97:159-166; Ripka, *New Scientist* Jun. 16, 1988 pp.54-57; McKinaly and Rossmann, 1989, *Ann. Rev. Pharmacol. Toxicol.* 29:111-122; Perry and Davies. *OSAR Quantitative Structure-Activity Relationships in Drug Design* pp. 189-193 (Alan R. Liss, Inc., 1989); Lewis and Dean, 1989, *Proc. R. Soc. Lond.* 236:125-140, 141-152; and, regarding a model receptor for nucleic acid components, Askew et al., *Am. J. Chem. Soc.* 111:1082-1090. Computer programs designed to screen and depict chemicals are available from companies such as MSI (supra), Allelix, Inc. (Mississauga, Ontario, Canada), and Hypercube, Inc. (Gainesville, Fla.).

These applications are largely designed for drugs specific to particular proteins; however, they can be adapted to the design of drugs specific to identified regions of DNA or RNA. Chemical libraries that can be used in the protocols described herein include those available, e.g., from ArQule, Inc. (Medford, Mass.) and Oncogene Science, Inc. (Uniondale, N.Y.).

In addition to designing and generating compounds that alter binding, as described above, libraries of known compounds, including natural products, synthetic chemicals, and biologically active materials including peptides, can be screened for compounds that are inhibitors or activators of the RNAi pathway components identified herein.

Compounds identified by methods described above can be used, for example, for elaborating the biological function of RNAi pathway gene products (e.g., an RDE-1), and to treat genetic disorders involving an RNAi pathway protein.

Assays for testing the effectiveness of compounds such as those described herein are further described below.

In vitro Screening Assays for Compounds that Bind to RNAi Pathway Proteins and Genes In vitro systems can be used to identify compounds that interact with (e.g., bind to) RNAi pathway proteins or genes encoding those proteins (e.g., rde-1 and its protein product). Such compounds are useful, for example, for modulating the activity of these entities, elaborating their biochemistry, treating disorders in which a decrease or increase in dsRNA mediated genetic interference is desired. Such compounds may also be useful to treat diseases in animals, especially humans, involving nematodes, e.g., trichinosis, trichuriasis, and toxocariasis. Compounds such as those described herein may also be useful to treat plant diseases caused by nematodes. These compounds can be used in screens for compounds that disrupt normal function, or may themselves disrupt normal function.

Assays to identify compounds that bind to RNAi pathway proteins involve preparation of a reaction mixture of the protein and the test compound under conditions sufficient to allow the two components to interact and bind, thus forming a complex which can be removed and/or detected.

Screening assays can be performed using a number of methods. For example, an RNAi pathway protein from an organism (e.g., RDE-1), peptide, or fusion protein can be immobilized onto a solid phase, reacted with the test compound, and complexes detected by direct or indirect labeling of the test compound. Alternatively, the test compound can be immobilized, reacted with the RNAi pathway molecule, and the complexes detected. Microtiter plates may be used as the solid phase and the immobilized component anchored by covalent or noncovalent interactions. Non-covalent attachment may be achieved by coating the solid phase with a solution containing the molecule and drying. Alternatively, an antibody, for example, one specific for an RNAi pathway protein such as RDE-1 is used to anchor the molecule to the solid surface. Such surfaces may be prepared in advance of use, and stored.

In these screening assays, the non-immobilized component is added to the coated surface containing the immobilized component under conditions sufficient to permit interaction between the two components. The unreacted components are then removed (e.g., by washing) under conditions such that any complexes formed will remain immobilized on the solid phase. The detection of the complexes may be accomplished by a number of methods known to those in the art. For example, the nonimmobilized component of the assay may be prelabeled with a radioactive or enzymatic entity and detected using appropriate means. If the non-immobilized entity was not prelabeled, an indirect method is used. For example, if the non-immobilized entity is an RDE-1, an antibody against the RDE-1 is used to detect the bound molecule, and a secondary, labeled antibody used to detect the entire complex.

Alternatively, a reaction can be conducted in a liquid phase, the reaction products separated from unreacted components, and complexes detected (e.g., using an immobilized antibody specific for an RNAi pathway protein).

Cell-based assays can be used to identify compounds that interact with RNAi pathway proteins. Cell lines that naturally express such proteins or have been genetically engineered to express such proteins (e.g., by transfection or transduction of an rde-1 DNA) can be used. For example, test compounds can be administered to cell cultures and the amount of mRNA derived from an RNAi pathway gene analyzed, e.g., by Northern analysis. An increase in the amount of RNA transcribed from such a gene compared to control cultures that did not contain the test compound indicates that the test compound is an inhibitor of the RNAi pathway. Similarly, the amount of a polypeptide encoded by an RNAi pathway gene, or the activity of such a polypeptide, can be analyzed in the presence and absence of a test compound. An increase in the amount or activity of the polypeptide indicates that the test compound is an inhibitor of the RNAi pathway.

Ectopic Expression of an RNAi Pathway Gene

Ectopic expression (i.e., expression of an RNAi pathway gene in a cell where it is not normally expressed or at a time when it is not normally expressed) of a mutant RNAi pathway gene (i.e., an RNAi pathway gene that suppresses genetic interference) can be used to block or reduce endogenous interference in a host organism. This is useful, e.g., for enhancing transgene expression in those cases where the RNAi pathway is interfering with expression of a transgene. Another method of accomplishing this is to knockout or down regulate an RNAi pathway gene using methods known in the art. These methods are useful in both plants and animals (e.g., in an invertebrate such as a nematode, a mouse, or a human).

Ectopic expression of an RNAi pathway gene, e.g., rde-1 or rde-4 can also be used to activate the RNAi pathway. In some cases, targeting can be used to activate the pathway in specific cell types, e.g., tumor cells. For example, a non-viral RNAi pathway gene construct can be targeted in vivo to specific tissues or organs, e.g., the liver or muscle, in patients. Examples of delivery systems for targeting such constructs include receptor mediated endocytosis, liposome encapsulation (described below), or direct insertion of non-viral expression vectors.

An example of one such method is liposome encapsulation of nucleic acid. Successful in vivo gene transfer has been achieved with the injection of DNA, e.g., as a linear construct or a circular plasmid, encapsulated in liposomes (Ledley, Human Gene Therapy 6:1129-1144 (1995) and Farhood, et al., Ann. NY Acad. Sci. 716:23-35 (1994)). A number of cationic liposome amphiphiles are being developed (Ledley, Human Gene Therapy 6:1129-1144 (1995); Farhood, et al., Ann. NY Acad. Sci., 716:23-35 (1994) that can be used for this purpose.

Targeted gene transfer has been shown to occur using such methods. For example, intratracheal administration of cationic lipid-DNA complexes was shown to effect gene transfer and expression in the epithelial cells lining the bronchus (Brigham, et al., Am. J. Respir. Cell Mol. Biol. 8:209-213 (1993); and Canonico, et al., Am. J. Respir. Cell Mol. Biol. 10:24-29 (1994)). Expression in pulmonary tissues and the endothelium was reported after intravenous injection of the complexes (Brigham, et al., Am. J. Respir. Cell Mol. Biol. 8:209-213 (1993); Zhu, et al., Science, 261:209-211 (1993); Stewart, et al., Human Gene Therapy 3:267-275 (1992); Nabel, et al., Human Gene Therapy 3:649-656 (1992); and Canonico, et al., J. Appl. Physiol. 77:415-419 (1994)). An expression cassette for an RNAi pathway sequence in linear, plasmid or viral DNA forms can be condensed through ionic interactions with the cationic lipid to form a particulate complex for in vivo delivery (Stewart, et al., Human Gene Therapy 3:267-275 (1992)).

Other liposome formulations, for example, proteoliposomes which contain viral envelope receptor proteins, i.e., virosomes, have been found to effectively deliver genes into hepatocytes and kidney cells after direct injection (Nicolau, et al., Proc. Natl. Acad. Sci. USA 80:1068-1072 (1993); Kaneda, et al., Science 243:375-378 (1989); Mannino, et al., Biotechniques 6:682 (1988); and Tomita, et al., Biochem. Biophys. Res. Comm. 186:129-134 (1992)).

Direct injection can also be used to administer an RNAi pathway nucleic acid sequence in a DNA expression vectors, e.g., into the muscle or liver, either as a solution or as a calcium phosphate precipitate (Wolff, et al., Science 247: 1465-1468 (1990); Ascadi, et al., The New Biologist 3:71-81 (1991); and Benvenisty, et al., Proc. Natl. Acad. Sci. USA 83:9551-9555 (1986).

Preparation of RNAi Agents

RNAi pathway components can be used to prepare RNAi agents. Such agents are dsRNAs that have been treated with RNAi pathway components rendering the treated dsRNA capable of activity in the RNAi pathway and can be used as sequence-specific interfering agents useful for targeted genetic interference. Specifically, treating a dsRNA with an RDE-1 and RDE-4 is useful for making an RNAi agent. An RNAi agent can be produced by preincubating a dsRNA in vitro in the presence of RDE-1 and RDE-4.

Another method of preparing an RNAi agent is to activate the RNAi pathway in a target cell (i.e., a cell in which it is desirable to activate the RNAi pathway such as a tumor cell) by transgenesis of an rde-1 coding sequence and an rde-4 coding sequence into the target cell.

RNAi pathway polypeptides can be modified, e.g., to enhance their stability or cellular uptake, by attaching lipophilic or other helper groups to the polypeptide, by the formation of chimeras with proteins or other moieties that are taken up by cells, or by the use of liposomes or other techniques of drug delivery known in the art.

In *C. elegans*, RNAi agents appear to spread from cell to cell, thus, active RNAi agents can diffuse or be actively transported from conditioned media or serum directly into target cells. Alternatively, RNAi agents can be injected into an organism or cell. They may also be incorporated into a cell using liposomes or other such methods known in the art.

Such methods are useful for stimulating the RNAi pathway in *C. elegans* cells, and in heterologous cells including plants and vertebrate cells. Such methods are useful in mammalian, e.g., human cells.

Enhanced Delivery of a Cargo Compound

RNAi pathway components that mediate the transport of dsRNA into cells and tissues can be used to promote the entry of dsRNA into cells and tissues, including dsRNA that is linked to another compound. The method is accomplished by linking dsRNA to a cargo compound (e.g., a drug or DNA molecule), e.g., by a covalent bond. The endogenous RNAi pathway gene expressing dsRNA transport function is activated using methods known in the art. Alternatively, other methods can be used such as transfecting the target cell with the gene that affects transport thus permitting the cell or tissue to take up the dsDNA.

EXAMPLES

The invention is further described in the Examples below which describe methods of identifying mutations in the RNAi pathway and methods of identifying genes encoding components of the RNAi pathway.

Example 1

Strains and Alleles

The Bristol strain N2 was used as standard wild-type strain. The marker mutations and deficiencies used are listed by chromosomes as follows: LGI: dpy-14(e188), unc-13 (e51); LGIII: dpy-17(e164), unc-32(e189); LGV: dpy-11 (e224), unc-42(e270), daf-11(m87), eDf1, mDj3, nDf31, sDf29, sDf35, unc-76(e911). The *C. elegans* strain DP13 was used to generate hybrids for STS linkage-mapping (Williams et al., 1992, *Genetics* 131:609-624).

Sensitivity to RNAi was tested in the following strains. MT3126: mut-2(r459) (obtained from John Collins, Department of Biochemistry & Molecular Biology, University of New Hampshire, Durham, N.H.); dpy-19(n1347), TW410: mut-2(r459) sem-4(n1378), NL917: mut-7(pk204), SS552: mes-2(bn76) rol-1(e91)/mnC1 (obtained from S. Strome, Biology Dept., Indiana University), SS449: mes-3(bn88) dpy-5(e61) (from S. Strome, supra); hDp20, SS268: dpy-11 (e224) mes-4(bn23) unc-76(e911)/nT1, SS360: mes-6 (bn66) dpy-20(e1282)/nT1, CB879: him-1 (e879). A non-Unc mut-6 strain used was derived from RW7096: mut-6 (st702) unc-22(st192::Tc1), due to the loss of Tc1 insertion in unc-22.

Homozygous mutants of mut-6, mes-2, 3, 4, 6 and him-1 showed sensitivity to RNAi by injection of pos-1 dsRNA. The dose of injected RNA was about 0.7 mg/ml. This dose lies within the range where reduced concentration leads to reduced interference effects. The results of the injection of pos-1 dsRNA into these mutants (dead embryos/F1 progeny) were as follows: mut-6: 422/437, mes-2: 781/787, mes-3: 462/474, mes-4: 810/814, mes-6: 900/1,002, him-1: 241/248, N2 (control): 365/393.

To test mutator activity, a mutant that was caused by Tc4 transposon insertion was used; TR1175: unc-22(r765::Tc4). Strains TW410 and TR1175 were gifts from Q. Boese and J. Collins (Department of Biochemistry & Molecular Biology, University of New Hampshire, Durham, N.H.).

Example 2

RNA Interference Assay

Genetic interference using RNAi administered by microinjection was performed as described in Fire et al., 1998, supra and Rocheleau et al., 1997, *Cell* 90:707-716. pos-1 cDNA clone yk61h1, par-2 cDNA clone yk96h7, sqt-3 cDNA clone yk75f2 were used to prepare dsRNA in vitro. These cDNA clones were obtained from the *C. elegans* cDNA project (Y. Kohara, Gene Network Lab, National Institute of Genetics, Mishima 411, Japan).

Genetic interference using RNAi administered by feeding was performed as described in Timmons and Fire, 1998, *Nature* 395:854. pos-1 cDNA was cloned into a plasmid that contains two T7 promoter sequences arranged in head-to-head configuration. The plasmid was transformed into an *E. coli* strain, BL21 (DE3), and the transformed bacteria were seeded on NGM (nematode growth medium) plates containing 60 μg/ml ampicillin and 80 μg/ml IPTG. The bacteria were grown overnight at room temperature to inducepos-1 dsRNA. Seeded plates (BL21(DE3)[dsRNA] plates) stored at 4° C. remained effective for inducing interference for up to two weeks. To test RNAi sensitivity, *C. elegans* larvae were transferred onto BL21 (DE3)[dsRNA] plates and embryonic lethality was assayed in the next generation.

Transgenic lines expressing interfering RNA for unc-22 were engineered using a mixture of three plasmids: pPD [L4218] (unc-22 antisense segment, driven by myo-3 promoter); pPD[L4218] (corresponding unc-22 sense segment, driven by myo-3 promoter); pRF4 (semidominant transformation marker). DNA concentrations in the injected mixture were 100 μg/ml each. Injections were as described (Mello et al., 1991, *EMBO J.* 10:3959; Mello and Fire, 1995, *Methods in Cell Biol.* 48:451-482).

Example 3

Identification of RNAi-Deficient Mutants

A method of screening for mutants defective in the RNAi pathway was devised that would permit the large-scale application of dsRNA to mutagenized populations. Feeding worms *E. coli* which express a dsRNA, or simply soaking worms in dsRNA solution, are both sufficient to induce interference in *C. elegans* (Timmons and Fire, 1998, supra; Tabara et al., 1998, *Science* 282:430-431). To carry out a selection, the feeding method was optimized to deliver interfering RNA for an essential gene, pos-1. *C. elegans* hermaphrodites that ingest bacteria expressing dsRNA corresponding to a segment of pos-1 are themselves unaffected but produce dead embryos with the distinctive pos-1 embryonic lethal phenotype.

To identify strains defective in the RNAi pathway, wild-type animals were mutagenized, backcrossed, and the F2 generation examined for rare individuals that were able to produce complete broods of viable progeny. Chemical mutagenesis was used to generate the mutations as well as spontaneous mutations arising in the mut-6 strain in which Tc1 transposons are activated (Mori et al., 1988, *Genetics* 120:397-407). To facilitate screens for mutations, an egg laying starting strain was used. In the absence of egg laying, the F3 progeny remained trapped within the mother's cuticle. Candidate mutants had internally hatched broods of viable embryos and were thus easily distinguished from the background population of individuals filled primarily with dead embryos (FIG. 1A). Candidates were then re-tested for resistance to injected dsRNA.

The genetic screen used to isolate RNAi pathway mutants was similar to one designed by James R. Preiss for the identification of maternal effect mutants (Kemphues et al., 1988, *Cell* 52:311-320). An Egl strain, lin-2(e1309) was mutagenized with EMS and the F2 generation was cultured on a bacterial lawn expressing pos-1 dsRNA. Mutagenized populations were then screened for rare individuals that were able to produce complete broods of viable progeny forming a distinctive "bag of worms" phenotype. To make sure that the animals were truly resistant to RNAi, candidate strains were next assayed for resistance to RNAi by injection. Independent EMS induced alleles of rde-1 were found in two separate pools of mutagenized animals at a frequency of approximately one allele in 2,000 to 4,000 haploid genomes.

In addition, a search was made for spontaneous mutants using a mut-6 strain in which Tc1 transposons are activated (Mori et al., 1988). 100,000 mut-6, lin-2 animals (Mello et al., 1994) were cultured on bacteria expressing pos-1 dsRNA. After one generation of growth, surviving animals were transferred again to plates with bacteria expressing the dsRNA and screened for resistant mutants. Three resulting strains were genetically mapped. One of these strains (ne300) mapped to LGV and failed to complement rde-1 (ne299). Two strains ne299 and ne300 mapped to LGIII and define the rde-4 complementation group. Because the screen was clonal in nature and involved rounds of enrichment it is possible that both rde-4 strains are related.

Figure 1B:
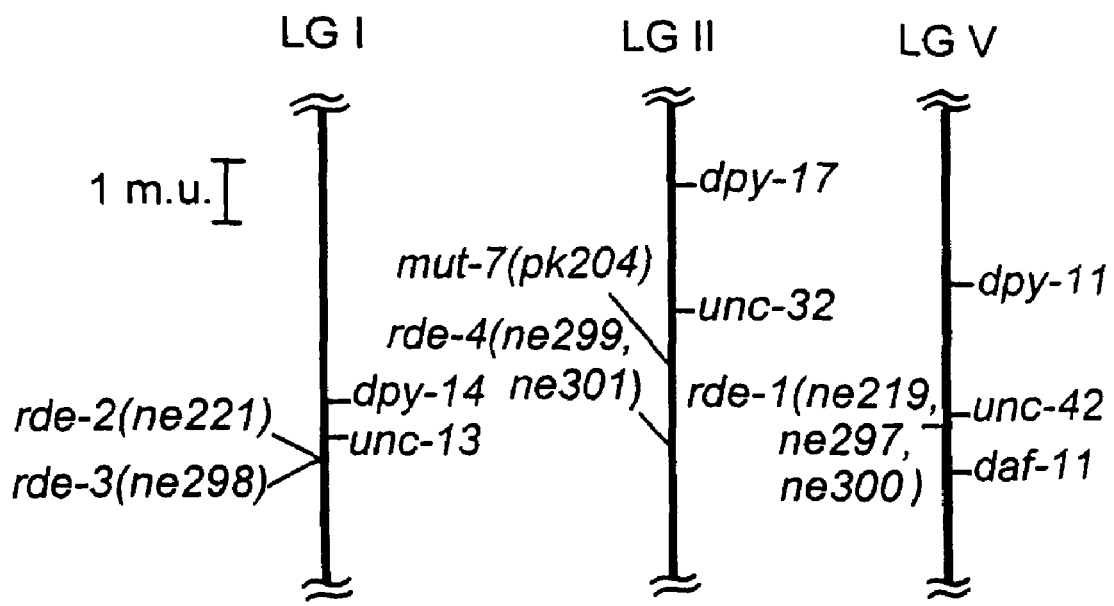
FIG. 1B is an illustration summarizing data from the genetic mapping of rde and mut mutations. The vertical bars represent chromosomes; LGI, LGIII, and LGV. Reference genetic markers are indicated at the right of each chromosome and the relative genetic positions of the rde and mut alleles are indicated at the left.

Seven mutant strains were selected for genetic mapping. These seven mutants defined four complementation groups; rde-1, with three alleles, rde-4, with two alleles, and rde-2, and rde-3, with one allele each (FIG. 1B).

To map the RNAi defective mutations, the RNAi resistant phenotype was assayed either by feeding bacteria expressing pos-1 dsRNA or by injection of a dsRNA mixture of pos-1 and unc-22. The same assays were used for complementation tests. In vivo expression of unc-22 dsRNA was also used for mapping of rde-1. Mapping with visible marker mutations was performed as described in Brenner (1974, *Genetics,* 77:71-94) and mapping with STS marker performed as described in Williams et al. (1992, supra).

ne219, ne297 and ne300 failed to complement each other, defining the rde-1 locus. rde-1 mutations mapped near unc-42 V. Three factor mapping was used to locate rde-1 (ne300) one eighth of the distance from unc-42 in the unc-42/daf-11 interval (3/24 Unc-non-Daf recombinants analyzed). The rde-1(ne300) allele complemented the chromosomal deficiency sDf29 and failed to complement eDf1, mDj3, nDf31 and sDf35. rde-2(ne221) and rde-3(ne298) mapped near unc-13 I. rde-2 complemented rde-3. rde-4 (ne299) and (ne300) mapped near unc-69 III and failed to complement each other. ne299 complemented mut-7 (pk204).

Figure 3:
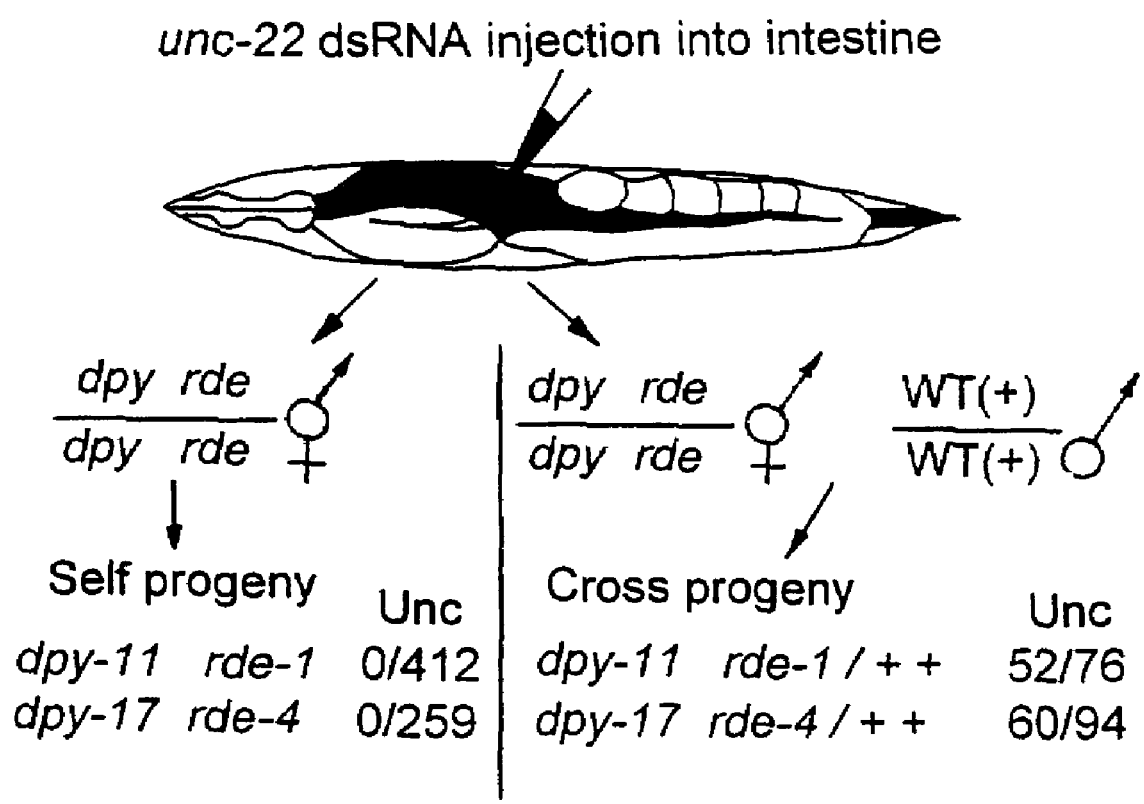
FIG. 3 is a schematic representation of homozygous rde-1 (ne299) and rde-4(ne299) mutant mothers receiving injections of dsRNA targeting the body muscle structural gene unc-22.

The rde-1(+) activity is sufficient maternally or zygotically. To test the maternal sufficiency, animals heterozygous for rde-1(ne219) were injected with dsRNA targeting the zygotic gene, sqt-3, and self progeny were assayed for the Sqt phenotype. 100% of the self progeny including rde-1 homozygous progeny were found to exhibit the Sqt phenotype. Thus, maternally provided rde-1(+) activity is sufficient to mediate interference with a zygotic target gene. Zygotic sufficiency was assayed by injecting homozygous rde-1 mothers with dsRNA targeting the zygotic unc-22 gene (FIG. 3). Injected animals were allowed to produce self-progeny or instead were mated after 12 hours to wild-type males, to produce heterozygous rde/+ cross-progeny. Each class of progeny was scored for the unc-22 twitching phenotype as indicated by the fraction shown if FIG. 3 (Unc progeny/total progeny). The injected animals were then mated with wild-type males. Self progeny from homozygous injected mothers were unaffected, however, 68% of the cross progeny were Unc. This result indicates that zygotically provided rde-1(+) activity is also sufficient. However both maternal and zygotic rde-1(+) activity contribute to zygotic interference as 100% of progeny from wild-type injected mothers exhibit unc-22 interference (606/606). Thus, rde-1 (+) and rde-4(+) activities are not needed for dsRNA uptake, transport or stability.

RNAi sensitivity of several existing *C. elegans* mutants was also examined. Most of these mutant strains were fully sensitive to RNAi. However, RNAi resistance was identified in two strains that had previously been shown to exhibit elevated levels of transposon mobilization (mutator strains): mut-2 (described in Collins et al., 1987, *Nature* 328:726-728) and mut-7 (described in Ketting et al., Cell, in press for release on Oct. 15, 1999). Another mutator strain, mut-6 (st702), was fully sensitive to RNAi. Since mutator strains continually accumulate mutations, the resistance of mut-2 and mut-7 may have been due to the presence of secondary mutations. To test this possibility we examined the genetic linkage between the mutator and RNAi resistance phenotypes of mut-2 and mut-7. We found that independently outcrossed mut-2(r459) mutator strains TW410 and MT3126 both showed resistance to RNAi. We mapped the RNAi resistance phenotype of mut-7(pk204) to the center of linkage group III (FIG. 1B), the position that had been defined for the mutator activity of mut-7(pk204) by Ketting et al. (supra). Together, these observations indicate that the RNAi resistance phenotypes of the mut-2 and mut-7 strains are genetically linked to their mutator activities. Animals heterozygous for the rde and mut alleles were generated by crossing wild-type males with Unc-Rde or Unc-Mut hermaphrodites. The rde and mut mutations appeared to be simple recessive mutations with the exception of mut-2 (r459), which appeared to be weakly dominant (FIG. 2A).

These data demonstrate that some genes are non-essential (e.g., rde-1 and rde-4).

This method can be used to identify additional mutations in RNAi pathway genes.

Example 4

Identification of Properties of RNAi-Deficient Mutants

Effects of rde Mutations in Germline and Somatic Tissues

Microinjection was used to assay the sensitivity of each rde strain to several distinct dsRNA species. The pos-1 and par-2 genes are expressed in the maternal germline and are required for proper embryonic development (Tabara et al., 1999, Development 126:1-11; Boyd et al., 1996, Development 122:3075-3084). All rde-strains tested (as well as mut-2 and mut-7) showed significant resistance to dsRNA targeting of these germline-specific genes (FIG. 2B), as well as to several other germline specific genes tested. The rde-3 data (asterisk in FIG. 2B) includes a 10% non-specific embryonic lethality present in the rde-3 strain.

To examine the effect of these mutations on genetic interference of somatically expressed genes, cells were injected with dsRNA targeting the cuticle collagen gene sqt-3 and the body muscle structural gene unc-22. sqt-3 hypomorphic mutants exhibit a short, dumpy body shape (dpy; van der Keyl et al., 1994, Dev. Dyn. 201:86-94). unc-22 mutations exhibit severe paralysis with a distinctive body twitching phenotype (Moerman et al., 1986, Proc. Natl. Acad. Sci. USA 83:2579-2583). rde-1, rde-3, rde-4 and mut-2 strains showed strong resistance to both sqt-3 and unc-22 dsRNA, while rde-2 and mut-7 strains showed partial resistance. Thus rde-2 and mut-7 appeared to be partially tissue- or gene-specific in that they were required for effective RNAi against germline but not somatically expressed genes. The rde-1, rde-3, rde-4, and mut-2 (+) activities appeared to be required for interference for all genes analyzed. The rde and mut strains differ from one another in sensitivity to sqt-2 dsRNA.

Effect of rde on Transposon Mobilization

The effect of rde mutations on transposon mobilization was examined. Two of the newly identified mutants, rde-2 and rde-3 exhibited a level of transposon activation similar to that of mut-7 (Table 1). In contrast, transposon mobilization was not observed in the presence of rde-1 or rde-4 (Table 1).

TABLE 1

TRANSPOSON MOBILIZATION AND MALE INCIDENCE IN rde AND mut STRAINS

| | Revertants |
|---|---|
| Percentage of Non-Unc | |
| unc-22 (r765::Tc4) | 0 (0/2000) |
| rde-1 (ne219); unc-22 (r765::Tc4) | 0 (0/4000) |
| rde-2 (ne221; unc-22 (r765::Tc4) | 0.96 (8/830) |
| rde-3 (ne298); unc-22 (r765::Tc4) | 1.6 (35/2141) |
| rde-4 (ne299); unc-22 (r765::Tc4) | 0 (0/2885) |

TABLE 1-continued

TRANSPOSON MOBILIZATION AND MALE INCIDENCE IN rde AND mut STRAINS

| | Revertants |
|---|---|
| mut-7 (pk204); unc-22 (r765::Tc4) | 1.0 (40/3895) |
| Percentage of Male Animals | |
| Wild type (n2) | 0.21 (2/934) |
| rde-1 (ne219) | 0.07 (1/1530) |
| rde-2 (ne221) | 3.2 (25/788) |
| rde-3 (ne298) | 7.8 (71/912) |
| rde-4 (ne299) | 0.24 (5/2055) |

X-Chromosome Loss

Mutator strains (including mut-2, mut-7) rde-2 and rde-3) exhibit a second phenotype: a high incidence of males reflecting an increased frequency of X-chromosome loss during meiosis (Collins et al., 1987, supra; Ketting et al., supra). This phenotype was observed in rde-2 and rde-3 strains, but not observed in the rde-1 and rde-4 strains which showed a wild-type incidence of males (Table 1).

A previously described gene-silencing process appears to act on transgenes in the germline of C. elegans. Although the silencing mechanisms are not well understood, they are known to depend on the products of the genes mes-2, 3, 4 and 6 (Kelly and Fire, 1998, Development 125:2451-2456). To examine the possibility that the RNAi and germline transgene-silencing might share common mechanistic features, we first asked if the mes mutants were resistant to RNAi. We found normal levels of RNA interference in each of these strains. We next asked if RNAi deficient strains were defective in transgene-silencing. Three strains were analyzed: mut-7(pk204), rde-1(ne219) and rde-2(ne221).

To analyze transgene silencing in mut-7 worms, homozygous mut-7 lines carrying various GFP reporters transgenes were generated as follows: N2 (Bristol strain) males were mated to mut-7 (pk204) unc-32 (e189) hermaphrodites; cross progeny males were then mated to strains carrying the GFP transgenes. mut-7 unc-32/++ cross progeny from these matings were cloned, and mut-7 unc-32 homozygous animals carrying the transgenes were isolated from their self-progeny. After the GFP reporter transgenes were introduced into different genetic backgrounds, activation of GFP transgene expression in germ cells was assayed at 25□C by fluorescence microscopy. The tested GFP reporter transgenes were each active in some or all somatic tissues, but had become silenced in the germline. The plasmids used and transgene designations are as follows: 1) pBK48 which contains an in-frame insertion of GFP into a ubiquitously expressed gene, let-858 (Kelly, et al., 1997, Genetics 146: 227-238). ccExPD727.1 contains more than 100 copies of pBK48 in a high copy repetitive array that is carried extrachromosomally. 2) pJH3.92 is an in-frame fusion of GFP with the maternal pie-1 gene (M. Dunn and G. Seydoux, Johns Hopkins University, Baltimore, Md.). jhEx1070 carries pJH3.92 in a low copy "complex" extrachromosomal array generated by the procedure of Kelly et al. (1997, supra) pJKL380.4 is a fusion of GFP with the C. elegans nuclear laminin gene, lam-1, which is expressed in all tissues (J. Liu and A. Fire). ccIn4810 carries pJKL380.4 in a complex array that has been integrated into the X chromosome by gamma irradiation using standard techniques.

The mut-7 strain was analyzed most extensively and was found to exhibit desilencing of three different germline transgenes tested (Table 2). The rde-2 strain exhibited a similar level of desilencing for a single transgene. In contrast, no transgene desilencing was observed in rde-1 mutants (Table 2). Thus, mut-7 and rde-2 which differ from rde-1 in having transposon mobilization and a high incidence of X-chromosome loss also differ from rde-1 in their ability to partially reactivate silent germline transgenes.

TABLE 2

REACTIVATION OF SILENCED TRANSGENES IN THE GERMLINE OF mut-7(pk204)

| Genotype | Transgene Array | Percentage Desilencing of Germline |
|---|---|---|
| +/+ | ccEx7271 | 8.3 (4/48) |
| mut-7/+ | ccEx7271 | 14.5 (7/48) |
| mut-7/mut-7 | ccEx7271 | 91.0 (71/78) |
| +/+ | jhEx1070 | 3.9 (2/51) |
| mut-7/mut-7 | jhEx1070 | 86.5 (32/37) |
| +/+ | ccIn4810 | 4.3 (2/46) |
| mut-7/mut-7 | ccIn4810 | 73.3 (33/45) |
| rde-1/rde-1 | ccEx7271 | 0 (0/34) |

Example 5

Requirement for rde-1(+) and rde-4(+) Activities in Target Tissue

The rde-1 and rde-4 mutants differ from other RNAi deficient strains identified herein in that they do not cause transposon mobilization nor do they cause chromosome loss. The role of these genes in upstream events such as dsRNA uptake, transport or stability was examined. Such events could be required for interference induced by exogenous trigger RNAs but might be dispensable for natural functions of RNAi. To evaluate these upstream events, rde-1 and rde-4 homozygotes were exposed to dsRNA. The next generation was scored for interference. dsRNA targeting the unc-22 gene was injected into the intestinal cells of homozygous rde-1 and rde-4 hermaphrodites and the injected animals were then mated to wild-type males (FIG. 3). The self-progeny for both strains exhibited no interference with the targeted gene. However, there was potent interference in the rde-1/+ and rde-4/+ cross progeny (FIG. 3). These observations indicated that rde-1 and rde-4 mutants have intact mechanisms for transporting the interference effect from the site of injection (the intestine) into the embryos of the injected animal and then into the tissues of the resulting progeny. The stability of the resulting interference also appeared to be normal in rde-1 and rde-4 as the homozygous injected mothers continued to produce affected cross progeny for several days after the time of injection.

To examine whether rde-1 and rde-4 mutants could block interference caused by dsRNA expressed directly in the target tissue, the muscle-specific promoter from the myo-3 gene (Dibb et al., 1989, *J. Mol. Biol.* 205:605-613) was used to drive the expression of both strands of the muscle structural gene unc-22 in the body wall muscles (Moerman et al., 1986, supra; Fire et al., 1991, *Development* 113:503-514). A mixture of three plasmids was injected: [myo-3 promoter::unc-22 antisense], [myo-3::unc-22 sense], and a marker plasmid (pRF4[rol-6(su1006gf)] [Mello et al., 1991]). Frequencies of Unc transgenic animals were followed in F1 and F2 generations. The $^a$Unc phenotype was weak. Wild-type animals bearing this transgene exhibit a strong twitching phenotype consistent with unc-22 interference. The twitching phenotype was strongly suppressed by both rde-1 and rde-4 mutants (Table 3). The mut-7 and rde-2 mutants which are both sensitive to unc-22(RNAi) by microinjection were also sensitive to promoter driven unc-22 interference in the muscle (Table 3). Taken together these findings suggest that rde-1(+) and rde-4(+) activities are not necessary for uptake or stability of the interfering RNA and may function directly in the target tissue.

TABLE 3

SENSITIVITY OF rde AND mut STRAINS TO TRANSGENE-DRIVEN INTERFERING RNA

| | Unc Animals in Transgenic F1 | Unc F2 Lines in Inherited Lines |
|---|---|---|
| Wild type (N2) | 26/59 | 10/11 |
| rde-1 (ne219) | 0/25 | 0/3 |
| rde-2 (ne221) | 35/72 | 14/14 |
| rde-3 (ne298) | 1$^a$/38 | 1$^a$/9 |
| rde-4 (ne299) | 0/51 | 0/4 |
| mut-7 (pk204) | 9/13 | 3/3 |

Example 6

Molecular Identification of the rde-1 Gene

The rde-1 gene was cloned using standard genetic mapping to define a physical genetic interval likely to contain the gene using YACs and cosmids that rescue rde-1 mutants. These were used to identify a cloned rde-1 cDNA sequence and a cloned rde-4 sequence. These methods can also be used to identify the genes for rde-2, rde-3, and rde-5 using the mutant strains provided herein.

To clone an rde-1 gene, yeast artificial chromosome clones (YACs) containing *C. elegans* DNA from this interval were used to rescue the rde-1 mutant phenotype. To facilitate this analysis candidate rescuing YACs were co-injected with plasmids designed to express unc-22(RNAi). YAC and cosmid clones that mapped near the rde-1 locus were obtained from A. Coulson. rde-1(ne299) was rescued by YAC clones: Y97C12 and Y50B5. The two overlapping YAC clones provided rde-1 rescuing activity as indicated by unc-22 genetic interference with characteristic body paralysis and twitching in the F1 and F2 transgenic animals. In contrast a non-overlapping YAC clone failed to rescue resulting in 100% non-twitching transgenic strains (FIG. 4A).

The rescuing activity was further localized to two overlapping cosmid clones, cosmid $C_{27}H_6$ and T10A5, and finally to a single 4.5 kb genomic PCR fragment predicted to contain a single gene, designated K08H10.7 (SEQ ID NO:1; FIGS. 5A-5C) The K08H 10.7 PCR product gave strong rescue when amplified from wild-type genomic DNA. This rescue was greatly diminished using a PCR fragment amplified from any of the three rde-1 alleles and was abolished by a 4 bp insertion at a unique NheI site in the rde-1 coding region. A wild-type PCR product from an adjacent gene $C_{27}H_{6.4}$, also failed to rescue.

Figure 4A:
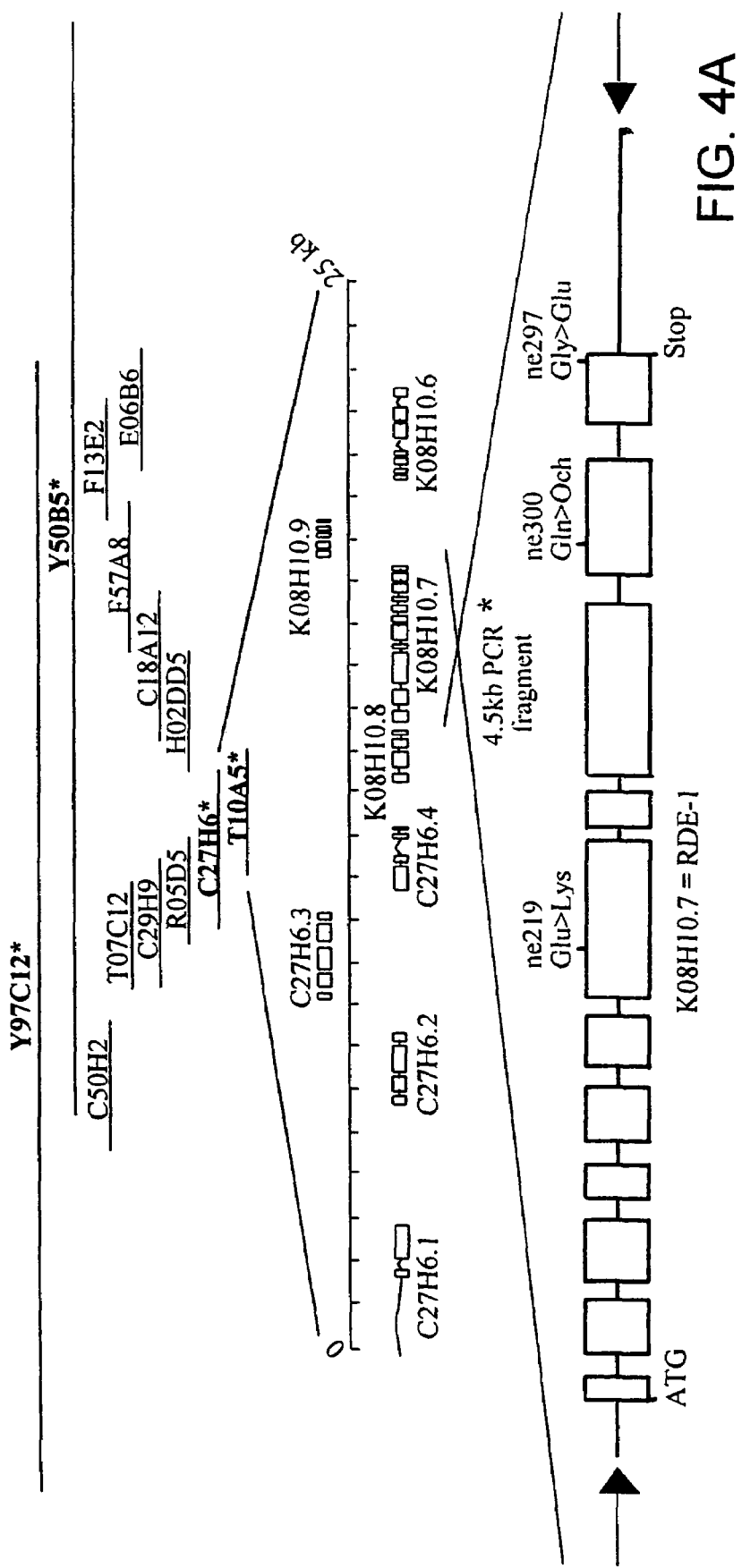
FIG. 4A is a schematic representation of the physical map of the rde-1 region. *C. elegans* YAC and cosmid DNA clones that were positive for rescue are indicated by an asterisk. A representation of the expanded interval showing a minimal, 25 kb, rescuing interval defined by the overlap between cosmids T10A5 and C27H6 is shown beneath the YAC and cosmid map. Predicted genes within this sequenced interval are illustrated above and below the hatch marked line. A single, rescuing, 4.5 kb PCR fragment containing the KO8H10.7 predicted gene is shown enlarged. Exon and intron (box/line) boundaries are shown as well as the positions of rde-1 point mutation in the predicted coding sequences.

The K08H10.7 gene from each of the rde-1 mutant strains was sequenced, and distinct point mutations were identified that are predicted to alter coding sequences in K08H10.7 (FIG. 4A). Based on these findings rde-1 can be identified as the K08H10.7 gene.

Figure 4B-1:
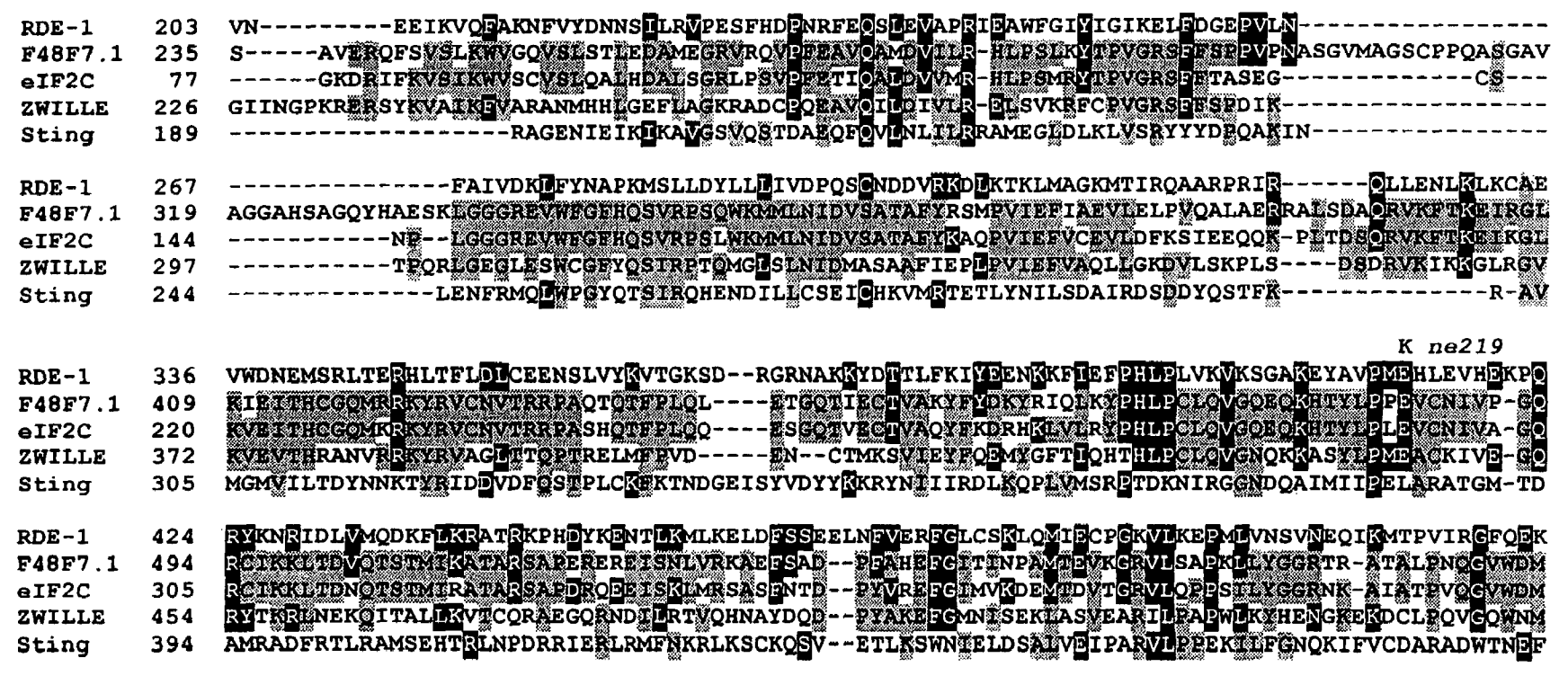
Figure 4B-3:
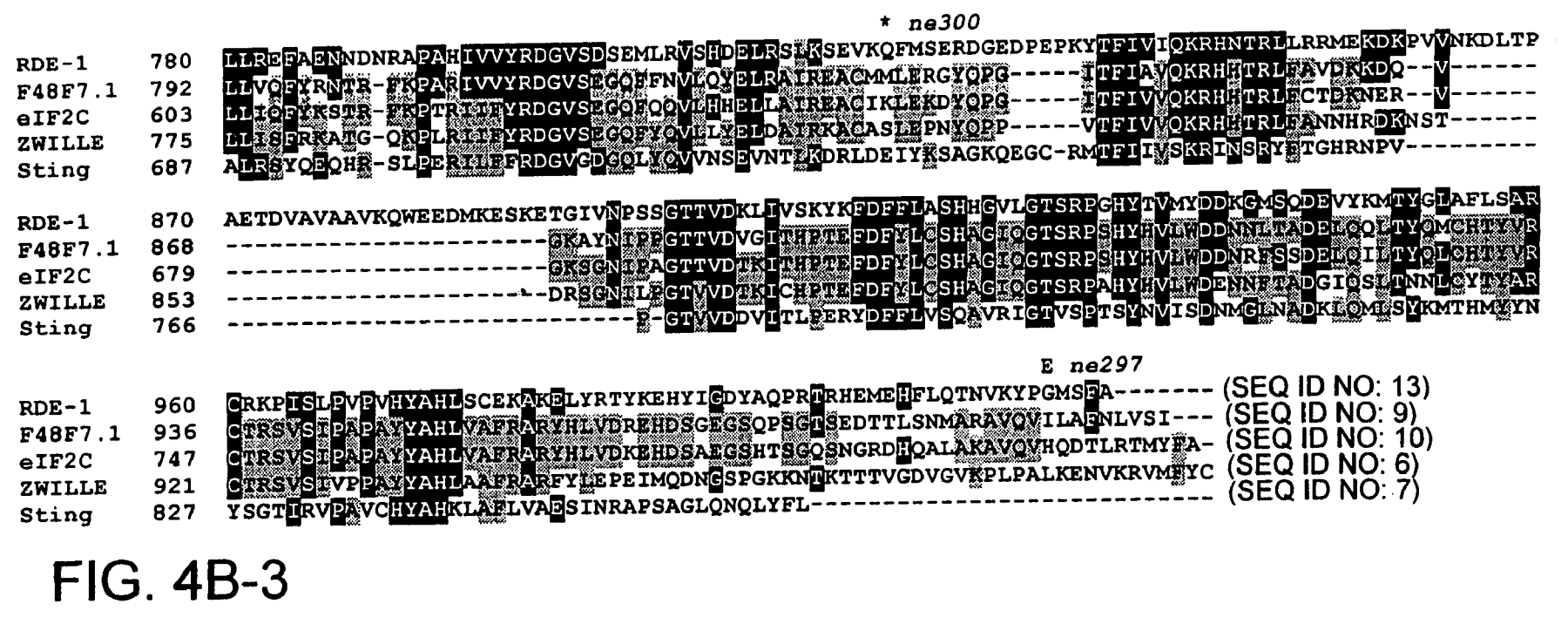

A full-length cDNA sequence was determined for rde-1 using the cDNA clones, yk296b10 and yk595h5. cDNA clones for rde-1 were obtained from Y. Kohara (Gene Network Lab, National Institute of Genetics, Mishima 411, Japan). The cDNA sequence of coding region and 3'UTR was determined on yk296b 10 except that the sequence of 5'UTR was determined on yk595h5. The GenBank accession number for rde-1 cDNA is AF180730 (SEQ ID NO:2). The rde-1 cDNA sequence was used to generate a predicted translation product (SEQ ID NO:3), referred to as RDE-1, consisting of 1020 amino acids. The RDE-1 sequence was used to query Genbank and identify numerous related genes in *C. elegans* as well as other animals and plants. This gene family includes at least 23 predicted *C. elegans* genes, several of which appear to be members of conserved subfamilies. Within subfamilies, conservation extends throughout the protein and all family members have a carboxy-terminal region that is highly conserved (FIG. 4B). Besides the genes shown in FIG. 4B, other related genes include ARGONAUTE 1 (*Arabidopsis*), SPCC736.11 (*S. pombe*), and Piwi (*Drosophila*). A portion of the N terminal region of RDE-1 showed no significant similarity to any of the identified related genes. There are no defined functional motifs within this gene family, but members including RDE-1 are predicted to be cytoplasmic or nuclear by PSORT analysis (Nakai and Horton, 1999, *Trends Biochem. Sci.* 24:34-36). Furthermore, one family member named eIF2C has been identified as a component of a cytoplasmic protein fraction isolated from rabbit reticulocyte lysates. The RDE-1 protein is most similar to the rabbit eIF2C. However, two other *C. elegans* family members are far more similar to eIF2C than is RDE-1 (FIG. 4B). RDE-1 may provide sequence-specific inhibition of translation initiation in response to dsRNA.

The rde-1 mutations appear likely to reduce or eliminate rde-1(+) activity. Two rde-1 alleles ne299 and ne297 are predicted to cause amino acid substitutions within the RDE-1 protein and were identified at a frequency similar to that expected for simple loss-of-function mutations. The rde-1(ne299) lesion alters a conserved glutamate to a lysine (FIG. 4B). The rde-1(ne297) lesion changes a non-conserved glycine, located four residues from the end of the protein, to a glutamate (FIG. 4B). The third allele, ne300, contains the strongest molecular lesion and is predicted to cause a premature stop codon prior to the most highly conserved region within the protein (Q>Ochre in FIG. 4B). Consistent with the idea that rde-1(ne300) is a strong loss of function mutation, we found that when placed in trans to a chromosomal deficiency the resulting deficiency trans-heterozyotes were RNAi deficient but showed no additional phenotypes. These observations suggest that rde-1 alleles are simple loss-of-function mutations affecting a gene required for RNAi but that is otherwise non-essential.

Because of its upstream role RNA interference (see Examples 8-10 below), the RDE-1 protein and fragments thereof can be used to prepare dsRNA that is useful as an RNAi agent.

Example 7

Maternal Establishment and Paternal Transmission of RNAi

Figure 7A:
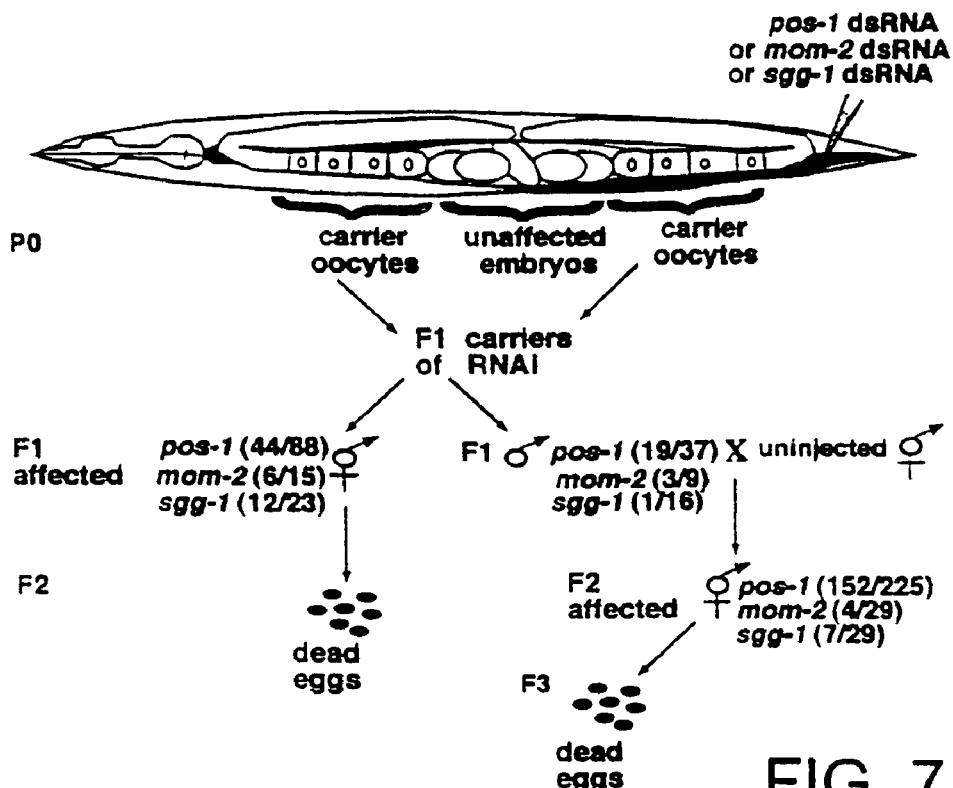
FIG. 7A is an illustration of the protocol for injection of a wild-type hermaphrodite with dsRNA.
Figure 7B:
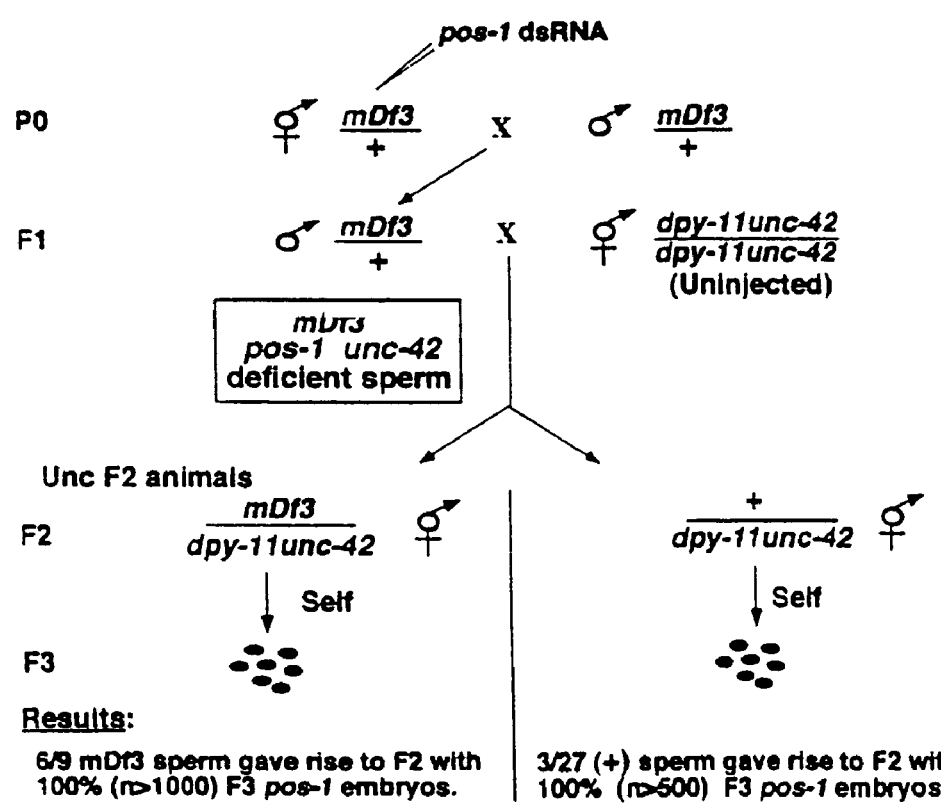
FIG. 7B is an illustration of a genetic scheme demonstrating extragenic inheritance of RNAi. The fraction shown represents the number of RNAi affected F2 hermaphrodites over the total number of cross progeny scored for each genotype class. Phenotypically uncoordinated (Unc).

To examine whether the interference effect induced by RNAi exhibited linkage to the target gene (e.g., was involved in a reversible alteration of the gene or associated chromatin), a strain was constructed such that the F1 males that carry the RNAi effect also bear a chromosomal deletion that removes the target gene (FIG. 7B). In the case of linkage to the target gene, the RNAi effect would be transmitted as a dominant factor.

In experiments testing the linkage of the interference effect to the target gene, three different species of dsRNA (pos-1 dsRNA, mom-2 dsRNA, or sgg-1 dsRNA) were delivered into *C. elegans* in independent experiments. The dsRNA was delivered by injection through a needle inserted into the intestine. In general, dsRNA was synthesized in vitro using T3 and T7 polymerases. Template DNA was removed from the RNA samples by DNase treatment (30 minutes at 37° C.). Equal amounts of sense and antisense RNAs were then mixed and annealed to obtain dsRNA. dsRNA at a concentration of 1-5 mg/ml was injected into the intestine of animals. In control experiments, mixtures of linearized template DNA plasmids used for synthesizing RNA failed to induce interference in P0, F1, or F2 animals when injected into the intestine of hermaphrodites at a concentration of 0.2 mg/ml. FIG. 7A illustrates this experiment. The gonad of the parent (P0) hermaphrodite has symmetrical anterior and posterior U-shaped arms as shown in FIG. 7A. Several fertilized eggs are shown in FIG. 7A, centrally located in the uterus. The rectangular mature oocytes are cued up in the gonad arms most proximal to the uterus. The embryos present in P0 at the time of injection gave rise to unaffected F1 progeny. Oocytes in the proximal arms of the injected P0 gonad inherit the RNAi effect but also carry a functional maternal mRNA (F1 carriers of RNAi).

After a clearance period during which carrier and unaffected F1 progeny are produced, the injected P0 begins to exclusively produce dead F1 embryos with the phenotype corresponding to the inactivation of the gene targeted by the injected RNA (Tabara et al. 1999, Development 126:1; C. Rocheleau, 1997, Cell 90:707). Potential F1 and F2 carriers of the interference effect were identified within the brood of the injected animal. In the case of hermaphrodites, carriers were defined as "affected" if the animals produced at least 20% dead embryos with phenotypes corresponding to maternal loss of function for the targeted locus. In the case of males, carriers were defined as animals whose cross progeny included at least one affected F2 hermaphrodite. The total number of carriers identified in each generation for each of three dsRNAs injected is shown in FIG. 7A as a fraction of the total number of animals assayed.

To examine the extragenic inheritance of RNAi, experiments were carried out investigating whether sperm that inherit the deletion and therefore have no copies of the target locus could carry the interference effect into the F2 generation. F1 males that carried both pos-1 (RNAi) and a chromosomal deficiency for the pos-1 locus were generated. The chromosome carrying the deficiency for pos-1 also carried a deficiency for phenotypically uncoordinated (unc). F2 progeny of the carrier male includes two genotypes: phenotypically wild-type animals that inherit the (+) chromosome, and phenotypically uncoordinated (Unc) progeny that inherit the mDf3 chromosome. In these experiments, the deficiency bearing sperm were just as capable as wild-type sperm of transferring interference to the F2 hermaphrodite progeny (FIG. 7B). Thus, the target locus was not needed for inheritance of the interference effect.

Surprisingly, although males were sensitive to RNAi and could inherit and transmit RNAi acquired from their mothers, direct injections into males failed to cause transmission of RNAi to the F1 for several genes tested. In an example of this type of protocol, wild type males were injected with targeting dsRNA: body muscle structural gene unc-22, cuticle collagen gene sqt-3, maternal genes pos-1 and sgg-1. Males of the pes-10::gfp strain (Seydoux, G. and Dunn, Mass., 1997, Development 124:2191-2201 were injected with gfp dsRNA. Injected males were affected by unc-22 and gfp dsRNA to the same extent as injected hermaphrodites. No RNAi interference was detected in F1 progeny or injected males (40 to 200 F1 animals scored for each RNA tested. Therefore, the initial transmission of RNAi to F1 progeny may involve a mechanism active only in hermaphrodites while subsequent transmission to the F2 progeny appears to involve a distinct mechanism, active in both hermaphrodites and males. The hermaphrodite-specific step may indicate the existence of a maternal germline process that amplifies the RNAi agent. These data show that extracts from the maternal germline tissues of *C. elegans* may be used in conjunction with RDE-1 and RDE-4 activity to create and to then amplify RNAi agents.

In addition, the germline factors that amplify the RNAi agents can be identified by mutations that result in an RNAi deficient mutant phenotype. Such factors can be used as additional components of an in vitro system for the efficient amplification of RNAi agents.

Example 8

Figure 8A:
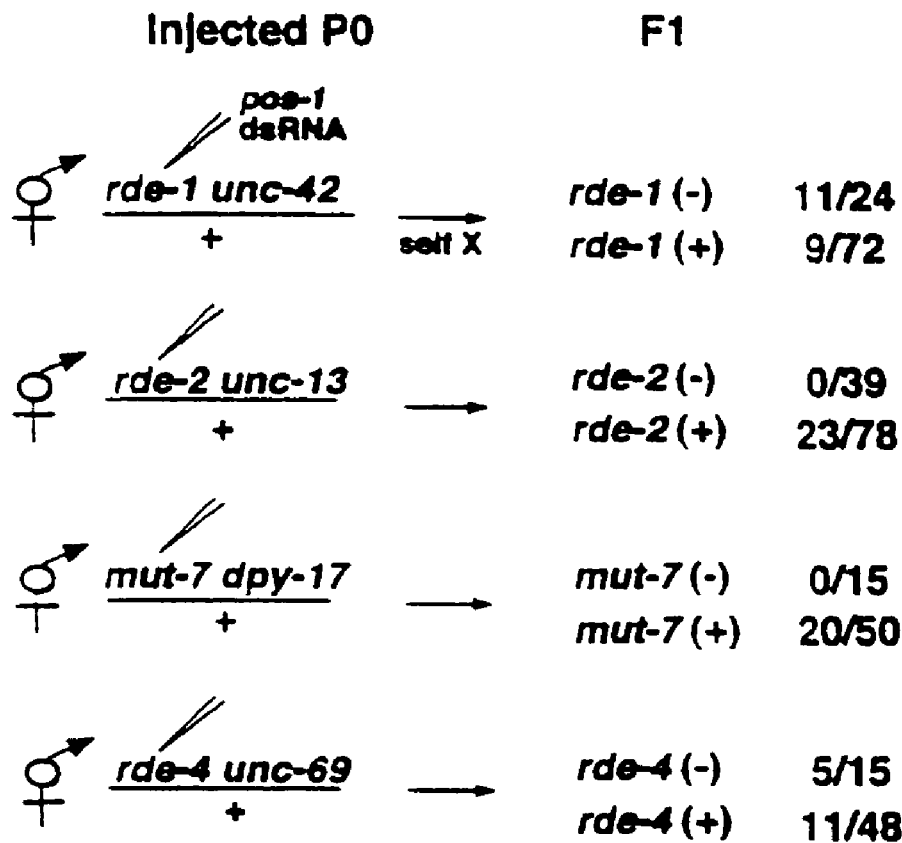
FIGS. 8A-8B are illustrations of a genetic scheme to determine if the wild-type activities of rde-1, rde-2, rde-4, and mut-7 are sufficient in the injected animal for interference among the F1 self progeny (A) illustrates crosses of heterozygous hermaphrodites; (B) illustrates crosses using homzygous F1 progeny from heterozygous mothers. The fraction shown represents the number of RNAi affected animals over the total number of cross progeny scored for each genotype class.
Figure 8B:
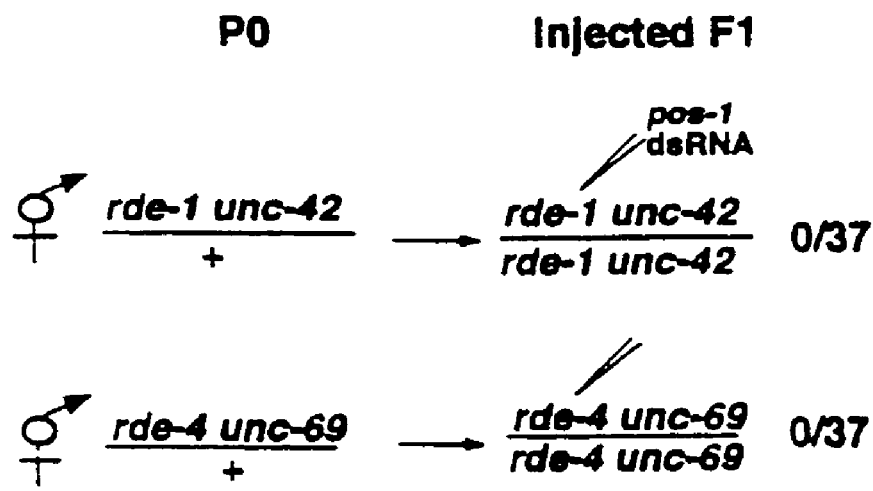

Sufficiency of Wild-Type Activities of rde-1, rde-2, mut-7, and rde-4 in Injected Animals for Interference Among F1 Self Progeny To investigate whether the activities of rde-1, rde-2, rde-4, and mut-7, respectively, are sufficient in injected hermaphrodites for interference in the F1 and F2 generations, crosses were designed such that wild-type activities of these genes would be present in the injected animal but absent in the F1 or F2 generations. To examine inheritance in the F1 generation, (hermaphrodite) mothers heterozygous for each mutant (P0) were injected, allowed to produce self-progeny (F1) and the homozygous mutant progeny in the F1 generation were examined for genetic interference (FIG. 8A). To do this, the heterozygous hermaphrodites from each genotype class, rde-1, unc-42/+; rde-2, unc-13/+; mut-7, dpy-17/+; and rde-4, unc-69/+ (the following alleles were used in this study: rde-1(ne300) unc-42, rde-1(ne219), rde-2 (ne221), rde-4(ne299), and mut-7(pk2040) were injected with pos-1 dsRNA. In each case, two types of F1 self progeny, distinguished by the presence of the linked marker mutations, were scored for interference (FIG. 8A). In these experiments the rde-1 and rde-4 mutant F1 progeny exhibited robust interference, comparable to wild-type, while the rde-2 and mut-7 F1 progeny failed to do so. In control experiments, homozygous F1 progeny from heterozygous (uninjected) mothers were directly injected with pos-1 dsRNA (FIG. 8B). Injection of dsRNA directly into the rde-1 and rde-4 mutant progeny of uninjected heterozygous mothers failed to result in interference. Thus, injection of dsRNA into heterozygous hermaphrodites resulted in an inherited interference effect that triggered gene silencing in otherwise RNAi resistant rde-1 and rde-4 mutant F1 progeny while rde-2 and mut-7 mutant F1 progeny remained resistant.

In this experiment, the expression of rde-1(+) and rde-4 (+) in the injected animal was sufficient for interference in later generations.

These data suggest that treatment of a dsRNA with functional rde-1 and rde-4 gene products can produce an agent that activates the remainder of the RNAi pathway.

Example 9

Requirements for rde-1, rde-2, rde-4, and mut-7 in F1 and F2 Interference

To examine the genetic requirements for RNAi genes in the F2 generation, F1 male progeny were generated that carry the interference effect as well as one mutant copy of each respective locus; rde-1, rde-2, and mut-7 (FIG. 9A). Each of these males was then backcrossed with uninjected hermaphrodites homozygous for each corresponding mutant (FIG. 9A). The resulting cross progeny (F1) included 50% heterozygotes and 50% homozygotes that were distinguished by the presence of the linked marker mutations. The heterozygous siblings served as controls and in each case exhibited interference at a frequency similar to that seen in wild-type animals (FIG. 9A). In these crosses, rde-2 and mut-7 homozygous F2 progeny failed to exhibit interference, indicating that the activities of these two genes are required for interference in the F2 generation. In contrast, we found that homozygous rde-1 F2 animals exhibited wild-type levels of F2 interference (FIG. 9A). Control rde-1 homozygotes generated through identical crosses were completely resistant to pos-1 RNAi when challenged de novo with dsRNA in the F2 generation. In these experiments, 35 rde-1 homozygous animals generated through crosses shown in FIG. 9A were tested by feeding bacteria expressing pos-1 dsRNA, and 21 similar animals were tested by direct injections of pos-1 dsRNA. All animals tested were resistant to pos-1 (RNAi). Thus, rde-1 activity in the preceding generations was sufficient to allow interference to occur in rde-1 mutant F2 animals while the wild-type activities of rde-2 and mut-7 were required directly in the F2 animals for interference.

In this experiment, the expression of rde-1(+) and rde-4 (+) in the injected animal was sufficient for interference in later generations. The wild-type activities of the rde-2 and mut-7 genes were required for interference in all generations asayed. Thus, rde-2 and mut-7 might be required only downstream or might also function along with rde-1 and rde-4.

These data lend additional support to the concept that an appropriately treated dsRNA could be used as an RNAi agent.

Example 10

Sufficiency of rde-1 Activity to Initiate RNA Interference in Injected Animals That Lack the Wild-type Activities of rde-2, mut-7, or rde-4

To ask if rde-2 and mut-7 activities function along with or downstream of rde-1, genetic cross experiments were designed in which the activities of these genes were present sequentially (FIG. 9B). For example, rde-1(+); rde-2(−) animals were injected with pos-1 dsRNA and then crossed to generate F1 hermaphrodites homozygous for rde-1(−); rde-2(+). In these experiments rde-1(+) activity in the injected animals was sufficient for F1 interference even when the injected animals were homozygous for rde-2 or mut-7 mutations (FIG. 10B). In contrast, rde-1(+) activity in the injected animals was not sufficient when the injected animals were homozygous for rde-4 mutant (FIG. 10B). Thus, rde-1 can act independently of rde-2 and mut-7 in the injected animal, but rde-1 and rde-4 must function together. These findings are consistent with the model that rde-1 and rde-4 function in the formation of the inherited interfering agent (i.e., an RNAi agent) while rde-2 and mut-7 function at a later step necessary for interference.

In summary, the above Examples provide genetic evidence for the formation and transmission of extragenic interfering agents in the *C. elegans* germline. Two *C. elegans* genes, rde-1, and rde-4, appear to be necessary for the formation of these extragenic agents but not for interference mediated by them. In contrast, the activities of two other genes, rde-2 and mut-7, are required only downstream for interference.

These examples provide evidence that the rde-1 and rde-4 gene products or their homologs (e.g., from a mammal) can be used to prepare agents effective in activating the RNAi pathway.

Example 11 rde-4 Sequences

An rde-4 gene was cloned using methods similar to those described in Example 6. The nucleic acid sequence (SEQ ID NO:4) and predicted amino acid sequence (SEQ ID NO:5) are illustrated in FIG. 10.

Figure 11:
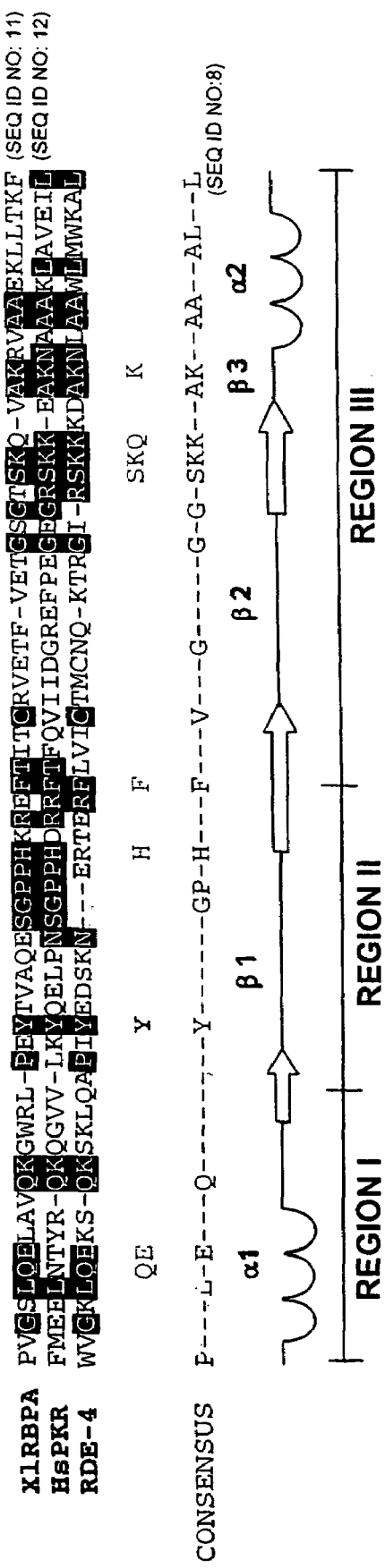
FIG. 11 is a depiction of regions of homology between the predicted RDE-4 amino acid sequence (SEQ ID NO:14), X1RBPA (SEQ ID NO:11), HsPKR (SEQ ID NO:12), and a consensus sequence (SEQ ID NO:8). A predicted secondary structure for RDE-4 is also shown illustrating predicted regions of α helix and β pleated sheet.

Analysis of the rde-4 nucleic acid sequence shows that it encodes a protein (RDE-4) with similarities to dsRNA binding proteins. Examples of the homology to X1RBPA (SEQ ID NO:11; Swissprot: locus_TRBP_XENLA, accession Q91836; Eckmann and Jantsch, 1997, J. Cell Biol. 138:239-253) and HSPKR (SEQ ID NO:12; AAF13156.1; Xu and Williams, 1998, J. Interferon Cytokine Res. 18:609-616), and a consensus sequence (SEQ ID NO:8) are shown in FIG. 11. Three regions have been identified within the predicted RDE-4 protein corresponding to conserved regions found in all members of this dsRNA binding domain family. These regions appear to be important for proper folding of the dsRNA binding domain. Conserved amino acid residues, important for interactions with the backbone of the dsRNA helix, are found in all members of the protein family including RDE-4 (see consensus residues in FIG. 11). This motif is thought to provide for general non-sequence-specific interactions with dsRNA. The RDE-4 protein contains conserved protein folds that are thought to be important for the assembly of the dsRNA binding domain in this family of proteins. Conserved amino acid residues in RDE-4 are identical to those that form contacts with the dsRNA in the crystal structure of the X1RBP dsRNA complex. These findings strongly suggest that RDE-4 is likely to have dsRNA binding activity.

Because RDE-4 contains a motif that is likely to bind in a general fashion to any dsRNA and because RDE-4 appears to function upstream in the generation of RNAi agents, the RDE-4 protein or fragments thereof can be used to convert any dsRNA into an RNAi agent. In addition to the dsRNA binding domain, RDE-4 contains other functional domains that may mediate the formation of RNAi agents. These domains may provide for interaction between RDE-4 and RDE-1 or for binding to enzymes such as nucleases that convert the dsRNA into the RNAi agent. Because of its RNA binding function in RNA interference, the RDE-4 protein and fragments thereof can be used to prepare dsRNA that is useful in preparing an RNAi agent.

Example 12

Identification of Regions of RDE-1 and RDE-4 that are Required for Creating an RNAi Agent In vivo and in vitro assays are used to identify regions in RDE-1 and RDE-4 that are important for the generation of RNAi agents. In the in vivo assay, rde-1 and rde-4 are introduced into the corresponding *C. elegans* mutant strains via transgenes (Tabara et al., Cell 99:123 (1999); and Example 13). Important functional domains in RDE-1 and RDE-4 are defined by systematically altering the proteins followed by reintroduction into mutant animals to test for rescue of the RNAi deficient phenotype. A series of nested deletions are analyzed for rescue activity for both rde-1 and rde-4. Specific point mutations are used to analyze the importance of specific amino acids. Chimera's are produced between RDE proteins and related proteins and genes. For example, coding sequences from RDE-1 homologs from the worm or from human are tested for their ability to rescue rde-1 mutants. Replacing the RDE-4 dsRNA binding motif with a distinct RNA binding motif, e.g., one that recognizes a specific viral dsRNA sequence or a ssRNA sequence will alter the specificity of the RNAi response perhaps causing sequence-specific or ssRNA-induced gene targeting. In one form of the in vitro assay, whole protein extracts from rde-1 or rde-4 deficient worm strains are used.

Recombinant RDE-1 or RDE-4 is then added back to reconstitute the extract. Altered RDE-1 and RDE-4 proteins (described above, including deletions, point mutants and chimeras) are made in vitro and then tested for their ability to function when added back to these extracts. RNAi activity is analyzed by injecting the reconstituted extracts directly into animals or by assaying for the destruction of an added in vitro synthesized target mRNA.

Example 13

Rescue of rde-4 Animals

Rescue of animals (e.g., *C. elegans*) that are mutant for an RNAi pathway is a useful method for identifying sequences from RNAi pathway genes that encode functional polypeptides, e.g., polypeptides that can eliminate the mutant phenotype.

Figure 12:
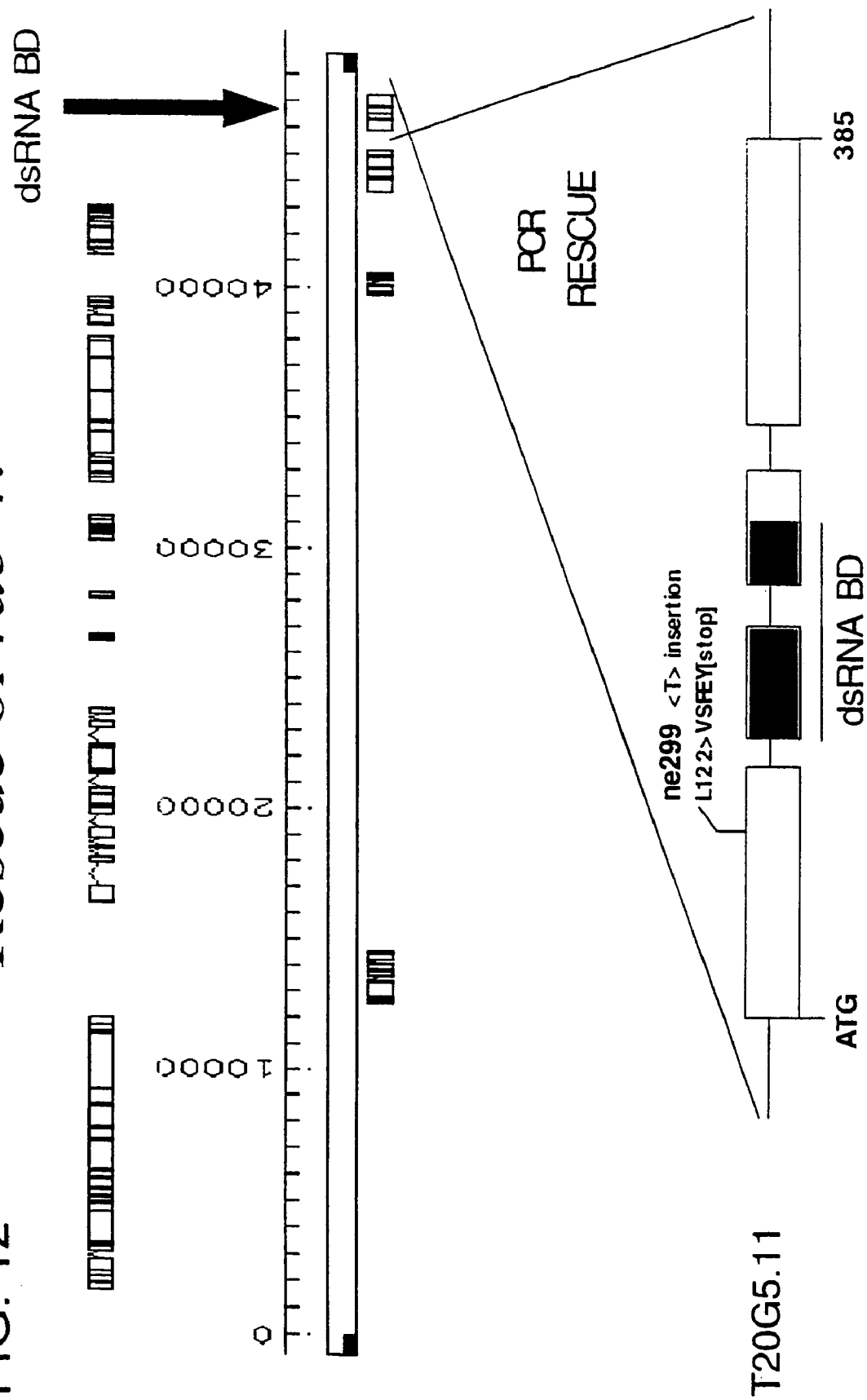
FIG. 12 illustrates a scheme for rescue of an rde-4.

An example of such a method for identifying rde-4 mutant animals is as follows. PCR using primers located 1 kb upstream and 500 nucleotides downstream of the open reading frame (T20G5.11; illustrated in FIG. 12) are used to amplify the rde-4 gene from *C. elegans* genomic DNA. The resulting PCR product is then injected along with reporter constructs described in Tabara et al. (Cell 99:123 (1999); incorporated herein in its entirety by reference), and the progeny of the injected animal are assayed for rescue of the RNAi deficient phenotype. The PCR product can also be cloned into a plasmid vector for site directed mutational analysis of RDE-4 (see Example 12). Co-injection of such a wild type RDE-4 plasmid and altered derivatives can be used to identify functional domains of rde-4. Similar methods can be used to identify functional domains of rde-1 and other RNAi pathway components.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially pure polypeptide encoded by a nucleic acid molecule which hybridizes under high stringency conditions of hybridization at 68° C. in 5×SSC/5× Denhardt solution/1.0% SDS, followed by washing in 0.1×SSC/0.1% SDS at 68° C. to a complement of the nucleic acid molecule set forth as SEQ ID NO:2, wherein the polypeptide mediates RNA interference (RNAi).

2. A substantially pure polypeptide fragment comprising amino acids 203 to 1020 of SEQ ID NO:3.

3. A substantially pure protein encoded by the nucleic acid molecule set forth as SEQ ID NO:2.

4. A substantially pure protein comprising the amino acid sequence of SEQ ID NO:3.

5. The substantially pure polypeptide of claim 1 wherein the polypetide is encoded by a nucleic acid molecule which can complement an rde-1 mutation.

6. A fusion protein comprising the polypeptide of any one of the preceding claims and a heterologous polypeptide.

7. The fusion protein of claim 6, wherein the heterologous polypeptide is selected from the group consisting of an immunoglobulin Fc (IgFc) polypeptide, a lacZ polypeptide, a glutathione S-transferase (GST) polypeptide, a six histidine tag polypeptide and a signal sequence polypeptide.

* * * * *

UNITED STATES PATENT AND TRADEMARK OFFICE
CERTIFICATE OF CORRECTION

| | |
|---|---|
| PATENT NO. | : 7,282,564 B2 |
| APPLICATION NO. | : 10/645746 |
| DATED | : October 16, 2007 |
| INVENTOR(S) | : Craig C. Mello et al. |

It is certified that error appears in the above-identified patent and that said Letters Patent is hereby corrected as shown below:

Column 1, Lines 16 through 18 replace
"Funding for the work described herein was provided by the federal government (GM58800 and GM37706), which has certain rights in the invention."

With

--Funding for the work described herein was made with government support under grant numbers GM58800 and GM37706, awarded by the National Institutes of Health.--

Signed and Sealed this

Eighth Day of April, 2008

JON W. DUDAS
*Director of the United States Patent and Trademark Office*